US009265789B2

(12) United States Patent
James et al.

(10) Patent No.: US 9,265,789 B2
(45) Date of Patent: Feb. 23, 2016

(54) TARGETING CLPTM1L BY RNA INTERFERENCE FOR TREATMENT AND PREVENTION OF CANCER

(71) Applicants: Michael Anthony James, Big Bend, WI (US); Haris G. Vikis, Milwaukee, WI (US); Ming You, Elm Grove, WI (US)

(72) Inventors: Michael Anthony James, Big Bend, WI (US); Haris G. Vikis, Milwaukee, WI (US); Ming You, Elm Grove, WI (US)

(73) Assignee: The Medical College of Wisconsin, Inc., Milwaukee, MI (US)

( * ) Notice: Subject to any disclaimer, the term of this patent is extended or adjusted under 35 U.S.C. 154(b) by 0 days.

(21) Appl. No.: 14/200,840

(22) Filed: Mar. 7, 2014

(65) Prior Publication Data

US 2014/0271818 A1    Sep. 18, 2014

Related U.S. Application Data

(60) Provisional application No. 61/777,711, filed on Mar. 12, 2013.

(51) Int. Cl.
| | |
|---|---|
| *C12N 15/11* | (2006.01) |
| *A61K 31/713* | (2006.01) |
| *A61K 31/7105* | (2006.01) |
| *C12N 15/113* | (2010.01) |

(52) U.S. Cl.
CPC ............ *A61K 31/713* (2013.01); *A61K 31/7105* (2013.01); *C12N 15/1138* (2013.01); *C12N 2310/14* (2013.01); *C12N 2310/531* (2013.01); *C12N 2330/50* (2013.01)

(58) Field of Classification Search
CPC .......................... C12N 2310/113; C12N 15/11
See application file for complete search history.

(56) References Cited

U.S. PATENT DOCUMENTS

| | | | | |
|---|---|---|---|---|
| 6,573,099 | B2 * | 6/2003 | Graham ........................ | 435/455 |
| 2003/0198975 | A1 * | 10/2003 | Azimzai et al. .................... | 435/6 |
| 2005/0255487 | A1 * | 11/2005 | Khvorova et al. ................ | 435/6 |
| 2007/0003575 | A1 * | 1/2007 | Bentwich ............. | C12N 15/111 |
| | | | | 424/204.1 |

FOREIGN PATENT DOCUMENTS

WO    WO 03/058021 A2 *  7/2003

OTHER PUBLICATIONS

Yoshiura et al. Genomics 54, 231-240, 1998.*
Google English translation of WO 03/058021, pp. 1-16, excluding sequence listing, translation retrieved on Apr. 2, 2015 from http://www.google.com/patents/WO2003058021A2?cl=en.*
Tuschl, The siRNA user guide, 2001 pp. 1-5.*
Paddison et al. Methods Mol. Biol. 2004, 265:85-100.*

Behrends, et al., Network Organization of the Human Autophagy System, Nature, 2010, 466(7302):68-76.
Carnero, The PKB/AKT Pathway in Cancer, Current Pharmaceutical Design, 2010, 16:34-44.
Cawthon, Telomere Measurement by Quantitative PCR, Nucleic Acids Research, 2002, 30(10):e47, pp. 1-6.
Chaparro, et al., Alterations in Thigh Subcutaneous Adipose Tissue Gene Expression in Protease Inhibitor-Based Highly Active Antiretroviral Therapy, Metabolism, 2005, 54(5):561-567.
Chen, et al., Prevalence of Telomerase Activity in Human Cancer, Journal of the Formosan Medical Association, 2011, 110(5):275-289.
Chen, et al., Multiple Variants of TERT and CLPTM1L Constitute Risk Factors for Lung Adenocarcinoma, Genetics and Molecular Research, 2012, 11(1):370-378.
Davis, et al., Evidence of RNAi in Humans from Systemically Administered siRNA Via Targeted Nanoparticles, Nature, 2010, 464:1067-1070.
Du et al., Calreticulin Promotes Cell Motility and Enhances Resistance to Anoikis Through STAT3-CTTN-Akt Pathway in Esophageal Squamous Cell Carcinoma, Oncogene, 2009, 28:3714-3722.
DuPage, et al., Conditional Mouse Lung Cancer Models Using Adenoviral or Lentiviral Delivery of Cre Recombinase, Nat. Protoc., 2009, 4(7):1064-1072.
Durcan, et al., Inhalable siRNA: Potential as a Therapeutic Agent in the Lungs, Molecular Pharmaceutics, 2008, 5 (4):559-566.
Fehringer, et al., Association of the 15q25 and 5p15 Lung Cancer Susceptibility Regions with Gene Expression in Lung Tumor Tissue, Cancer Epidemiology, Biomarkers & Prevention, 2012, 21(7):1097-1104.
Grundberg, et al., Mapping cis- and trans-regulatory Effects Across Multiple Tissues in Twins, Nature Genetics, 2012, 44(10):1084-1089.
Herzog, et al., Homozygous Codeletion and Differential Decreased Expression of p15(INK4b), p16(INK4a)-x and p16(INK4a)-B in Mouse Lung Tumor Cells, Oncogene, 1996, 13:1885-1891.
James, et al., Functional Characterization of CLPTM1L as a Lung Cancer Risk Candidate Gene in the 5p15.33 Locus, PLoS One, 2012, 7(6):e36116, pp. 1-9.
James, et al., CRR9/CLPTM1L Regulates Cell Survival Signaling and is Required for Ras Transformation and Lung Tumorigenesis, Cancer Research, Published OnlineFirst Dec. 23, 2013, DOI: 10.1158/0008-5472.CAN-13-1617.
Jensen, et al., Functional Selection of shRNA Loops from Randomized Retroviral Libraries, PLoS One, 2012, 7(8): e43095, pp. 1-7.

(Continued)

*Primary Examiner* — Brian Whiteman
(74) *Attorney, Agent, or Firm* — Quarles & Brady LLP

(57) ABSTRACT

Provided herein are compositions for reducing CLPTM1L expression in a cell as well as methods for using such compositions to treat or prevent cancer in a subject. In particular, compositions comprising RNAi-inducing constructs targeted to CLPTM1L and methods of administering such compositions to a subject to treat or prevent a disease or condition associated with CLPTM1L over-expression (e.g., lung cancer) are provided herein.

26 Claims, 17 Drawing Sheets

(56) References Cited

OTHER PUBLICATIONS

Jiang, et al., The Suppression of Lung Tumorigenesis by Aerosol-Delivered Folate-Chitosan-Graft-Polyethylenimine/Akt1 shRNA Complexes Through the Akt Signaling Pathway, Biomaterials, 2009, 30(29):5844-5852.

Koci, et al., Detachment-Mediated Resistance to TRAIL-induced Apoptosis is Associated with Stimulation of the PI3K/Akt Pathway in Fetal and Adenocarcinoma Epithelial Colon Cells, Cytokine, 2011, 55:34-39.

Konstantinova, et al., Inhibition of Human Immunodeficiency Virus Type 1 by RNA Interference Using Long-Hairpin RNA, Gene Therapy, 2006, 13:1403-1413.

Landi et al., A Genome-Wide Association Study of Lung Cancer Identifies a Region of Chromosome 5p15 Associated with Risk for Adenocarcinoma, The American Journal of Human Genetics, 2009, 85:679-691.

Lei, et al., Bcl-XL Small Interfering RNA Sensitizes Cisplatin-Resistant Human Lung Adenocarcinoma Cells, Acta Biochimica et Biophysica Sinica, 2007, 39(5):344-350.

Li, et al., Defining the Optimal Parameters for Hairpin-Based Knockdown Constructs, RNA, 2007, 13:1765-1774.

Lim, et al., Reduction in the Requirement of Oncogenic Ras Signaling to Activation of PI3K/AKT Pathway During Tumor Maintenance, Cancer Cell, 2005, 8:381-392.

Liu, et al., Design of Extended Short Hairpin RNAs for HIV-1 Inhibition, Nucleic Acids Research, 2007, 35 (17):5683-5693.

Liu, et al., Cumulative Effect of Multiple Loci on Genetic Susceptibility to Familial Lung Cancer, Cancer Epidemiology, Biomarkers & Prevention, 2010, 19(2):517-524.

Liu, et al., Atypical Protein Kinase CI (PKCI) Promotes Metastasis of Esophageal Squamous Cell Carcinoma by Enhancing Resistance to Anoikis via PKCI-SKP2-AKT Pathway, Molecular Cancer Research, 2011, 9(4):390-402.

Mayo, et al., The PTEN, Mdm2, p53 Tumor Suppressor-Oncoprotein Network, Trends in Biochemical Sciences, 2002, 27(9):462-467.

Mayo, et al., PTEN Protects p53 from Mdm2 and Sensitizes Cancer Cells to Chemotherapy, The Journal of Biological Chemistry, 2002, 277(7):5484-5489.

McDoniels-Silvers, et al., Inactivation of Both Rb and p53 Pathways in Mouse Lung Epithelial Cell Lines, Experimental Lung Research, 2001, 27(3):297-318.

McKay, et al., Lung Cancer Susceptibility Locus at 5p15.33, Nat. Genet., 2008, 40(12):1404-1406.

Meylan, et al., Requirement for NF-KB Signaling in a Mouse Model of Lung Adenocarcinoma, Nature, 2009, 462 (7269):104-107.

Mirabello, et al., The Association of Telomere Length and Genetic Variation in Telomere Biology Genes, Human Mutation, 2010, 31:1050-1058.

Ni, et al., CLPTM1L Is Overexpressed in Lung Cancer and Associated with Apoptosis, PLoS One, 2012, 7(12): E52598, pp. 1-8.

Pande, et al., Novel Genetic Variants in the Chromosome 5p15.33 Region Associate with Lung Cancer Risk, Carcinogenesis, 2011, 32(10):1493-1499.

Pooley, et al., No Association Between TERT-CLPTM1L Single Nucleotide Polymorphism rs401681 and Mean Telomere Length or Cancer Risk, Cancer Epidemiology, Biomarkers & Prevention, 2010, 19(7):1862-1865.

Rafnar, et al., Sequence Variants at the TERT-CLPTM1L Locus Associate with Many Cancer Types, Nature Genetics, 2009, 41(2):221-227.

Rosen, et al., Activated ras Prevents Downregulation of Bcl-XL Triggered by Detachment from the Extracellular Matrix: A Mechanism of ras-induced Resistance to Anoikis in Intestinal Epithelial Cells, The Journal of Cell Biology, 2000, 149(2):447-455.

Rubinson, et al., A Lentivirus-Based System to Functionally Silence Genes in Primary Mammalian Cells, Stem Cells and Transgenic Mice by RNA Interference, Nature Genetics, 2003, 33:401-406.

Scherf, et al., Epigenetic Screen Identifies Genotype-Specific Promoter DNA Methylation and Oncogenic Potential of CHRNB4, Oncogene, 2012, pp. 1-10.

Therasse, et al., New Guidelines to Evaluate the Response to Treatment in Solid Tumors, Journal of the National Cancer Institute, 2000, 92(3):205-216.

Timofeeva, et al., Influence of Common Genetic Variation on Lung Cancer Risk: Meta-Analysis of 14 900 Cases and 29 485 Controls, Human Molecular Genetics, 2012, 21(22):4980-4995.

Yamamoto, et al., A Novel Gene, CRR9, Which Was Up-Regulated in CDDP-Resistant Ovarian Tumor Cell Line, Was Associated with Apoptosis, Biochemical and Biophysical Research Communications, 2001, 280(4):1148-1154.

Yang, et al., Targeting Lentiviral Vectors to Specific Cell Types In Vivo, PNAS, 2006, 103(31):11479-11484.

Zienolddiny, et al., The TERT-CLPTM1L Lung Cancer Susceptibility Variant Associates with Higher DNA Adduct Formation in the Lung, Carcinogenesis, 2009, 30(8):1368-1371.

\* cited by examiner

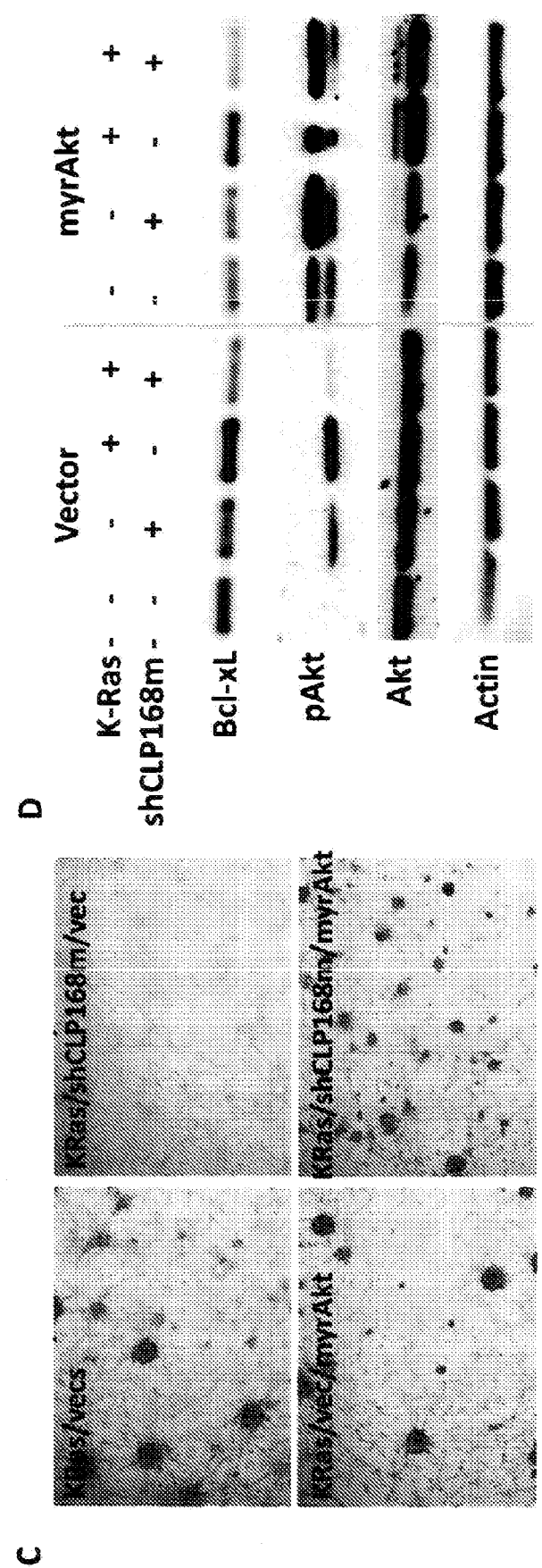
FIG. 4, continued

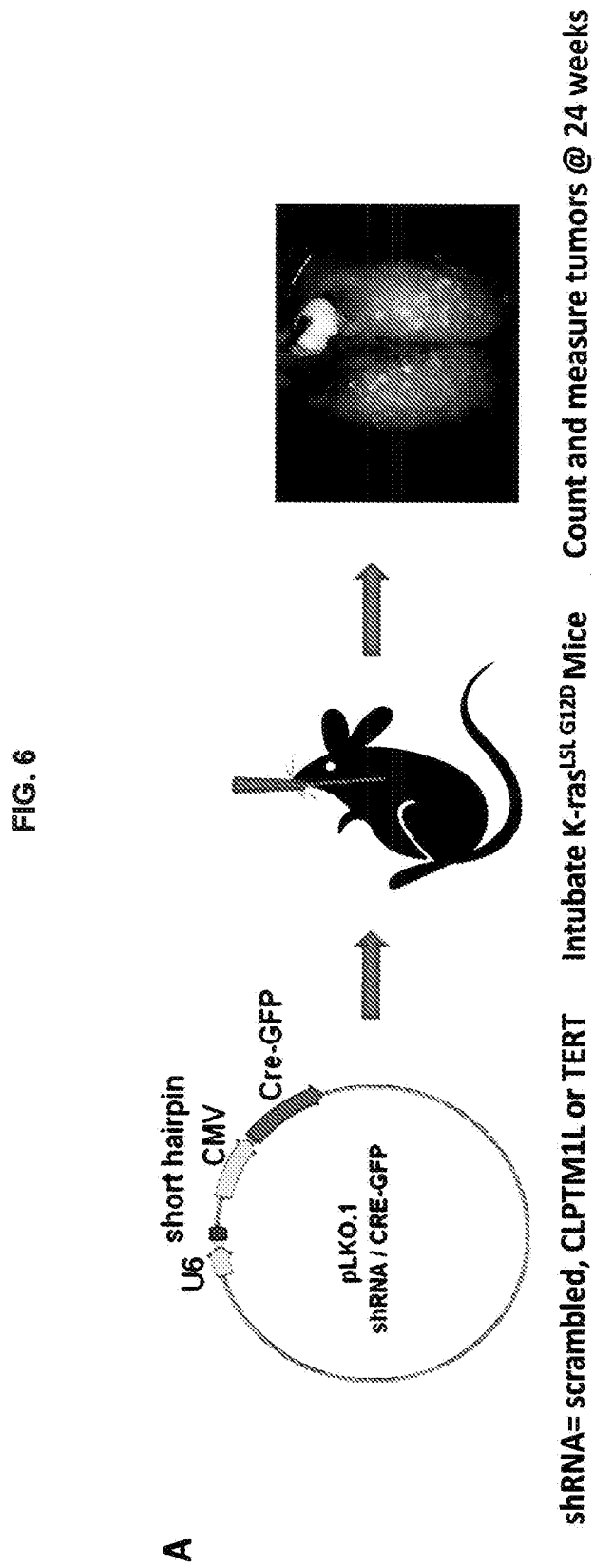

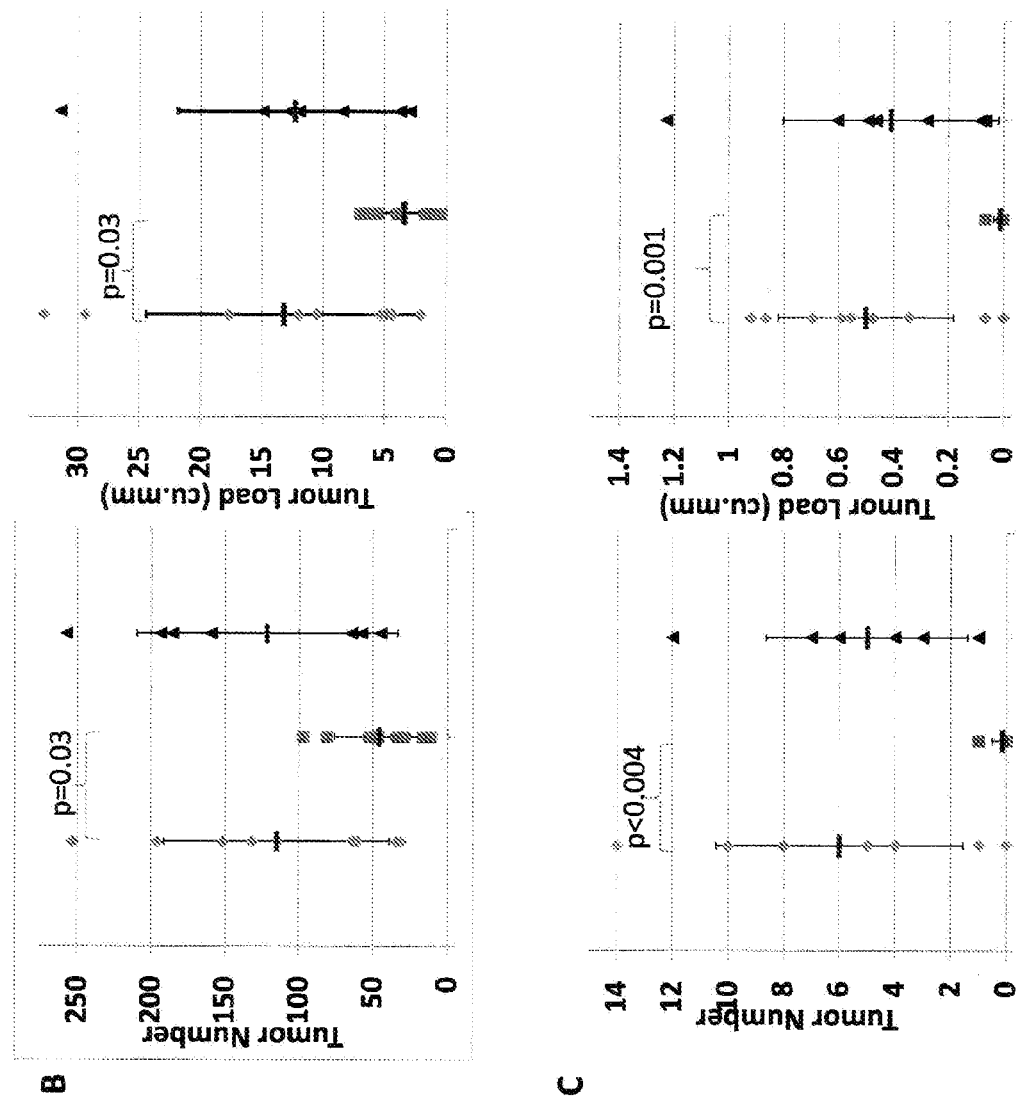
FIG. 6, continued

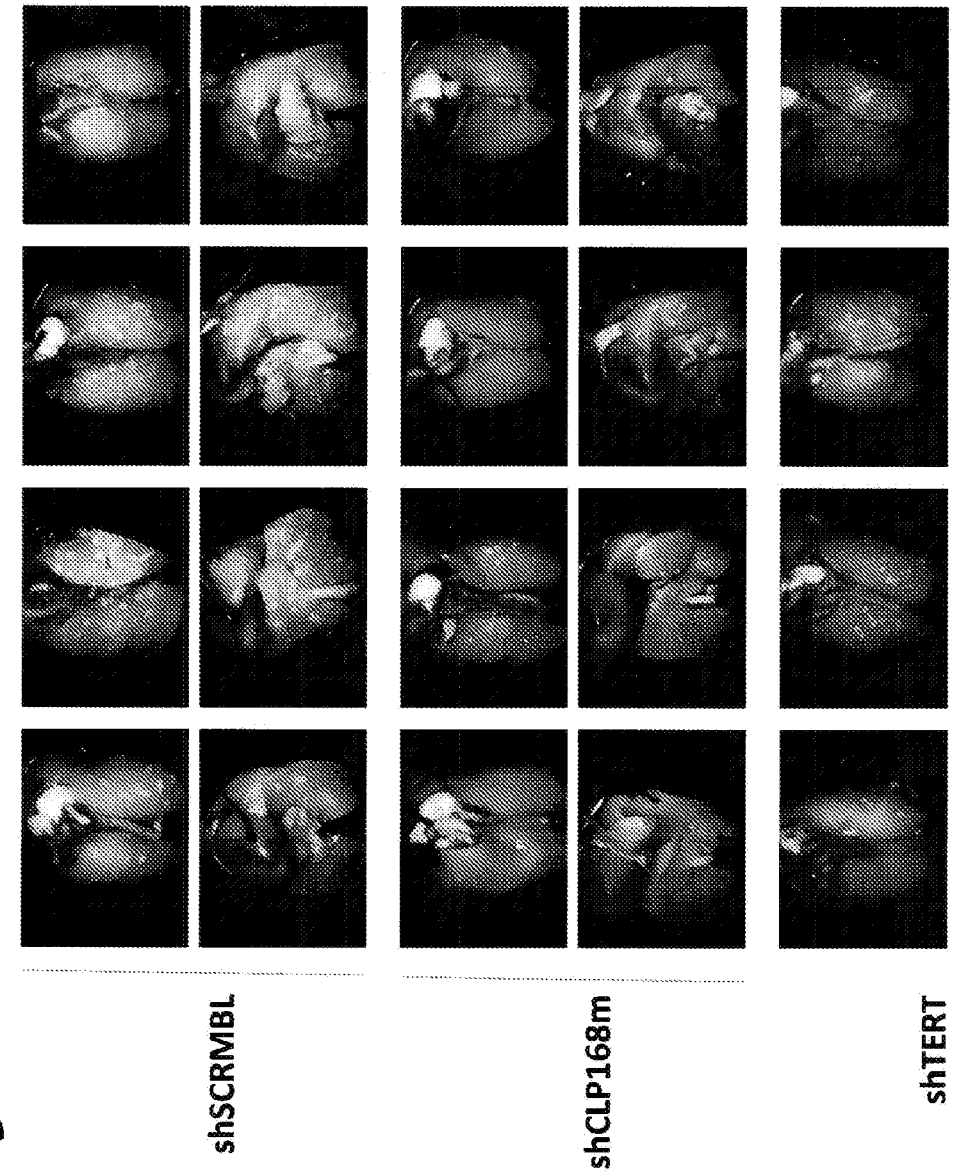
FIG. 6, continued

FIG. 12

SEQ ID NO:2 (CLPTM1L, 538 AA, UniProt ID: Q96KA5.11)
MWSGRSSFTSLVVGVFVVYVVHTCWVMYGIVYTRPCSGDANCIQPYLARRPKLQLSVYTTTRSHLGAENNIDLVL
NVEDFDVESKFERTVNVSVPKKTRNNGTLYAYIFLHHAGVLPWHDGKQVHLVSPLTTYMVPKPEEINLLTGESDTQ
QIEAEKKPTSALDEPVSHWRPRLALNVMADNFVFDGSSLPADVHRYMKMIQLGKTVHYLPILFIDQLSNRVKDLMVI
NRSTTELPLTVSYDKVSLGRLRFWIHMQDAVYSLQQFGFSEKDADEVKGIFVDTNLYFLALTFFVAAFHLLFDFLAF
KNDISFWKKKKSMIGMSTKAVLWRCFSTVVIFLFLLDEQTSLLVLVPAGVGAAIELWKVKKALKMTIFWRGLMPEFQ
FGTYSESERKTEEYDTQAMKYLSYLLYPLCVGGAVYSLLNIKYKSWYSWLINSFVNGVYAFGFLFMLPQLFVNYKL
KSVAHLPWKAFTYKAFNTFIDDVFAFIITMPTSHRLACFRDDVVFLVYLYQRWLYPVDKRRVNEFGESYEEKATRA
PHTD

FIG. 13

SEQ ID NO:3, partial coding sequence, 1759 nt (Genbank ID BC016399.1)

ctctgaccac ctacatggtc cccaagccag aagaaatcaa cctgctcacc ggggagtctg
atacacagca gatcgaggcg gagaagaagc cgacgagtgc cctgatgag ccagtgtccc
actggcgacc gcggctggcg ctgaacgtga tggcggacaa cttgtctt gacggtcct
ccctgcctgc cgatgtgcat cggtacatga agatgatcca gctggggaaa accgtgcatt
actgcccat cctgttcatc gaccagtca gcaaccgcgt gaaggacctg atggtcataa
accgctccac caccgagctg ccctcaccg tgtcctacga caaggtctca ctgggcggc
tgcgcttctg gatccacatg caggacgccg tgtactccct gcagcagtc gggtttcag
agaaagatgc tgatgaggtg aaaggaattt tgtagatac caacttatac ttcctgcgc
tgaccttctt tgtcgcagcg ttccatcttc tctttgatt cctgcctt aaaaatgaca
tcagttctg gaagaagaag aagagcatga tcggcatgtc caccaagctg tggaaagtga
agaaggcatt gaagatgact atttttgga gaggcctgat gcccgaattt cagtttggca
cttacagcga atcgagagg aaaaccgagg agtacgatac tcaggccatg aagtacttgt
catacctgct gtaccctctc tgtgtcgggg gtgctgtcta ttcactcctg aatatcaaat
ataagagctg gtactcctgg ttaatcaaca gcttcgtcaa cgggtctat gccttggtt
tcctcttcat gctgccccag ctctttgta actacaagtt gaagtcagtg gcacatcgc
cctgaaggc cttcacctac aaggcttca acaccttcat tgatgacgtc tttgcctca
tcatcaccat gcccacgtct caccgctgg cctgcttccg ggacgacgtg gtgttctgg
tctacctgta ccagcggtgg cttatcctg tggataaacg cagagtgaac gagtttgggg
agtcctacga ggagaaggcc acgcgggcgc ccacacgga ctgaaggccg cccgggctgc
cgccagccaa gtgcaacttg aattgtcaat gagtattt ggaagcatt ggaagaattc
ctagacattg cgtttctgt gttgccaaaa tccctcgga cattctcag acatctccca
agttccatc acgtcagatt tggagctggt agcgcttacg atgccccccac gtgtgaacat
ctgtcttggt cacagagctg ggtgtcgccg gtcaccttga gctgtggtgg ctccccggcac
acgagtgtcc gggttcggc catgtcctca cgcgggcagg ggtgggagcc ctcacaggca
aggggctgt tggatttcca ttcaggtgg ttttctaagt gctccttatg tgaatttcaa
acacgtatgg aattcattcc gcatgactc tggatcaaa ggctcttcc tcttttgttt
gagagttggt tgttttaaag cttaatgtat gttctattt taaaatatt ttttctgct
gtggcattt tctgacctg gtataatgaa agtatttcag atatttgagt ttaaccctt
tccagaaagt aatacatgat atggatttat ttatgcatta aaagagcaaa tttaaagagc
aaaaaaaaa aaaaaaaa

US 9,265,789 B2

TARGETING CLPTM1L BY RNA INTERFERENCE FOR TREATMENT AND PREVENTION OF CANCER

CROSS-REFERENCE TO RELATED APPLICATIONS

This application claims the benefit of U.S. Provisional Application No. 61/777,711, filed on Mar. 12, 2013, which is incorporated by reference herein in its entirety.

STATEMENT REGARDING FEDERALLY SPONSORED RESEARCH

This invention was made with government support under Grant No. U19 CA128147 awarded by the National Institutes of Health. The government has certain rights in the invention.

FIELD OF THE INVENTION

The present invention generally relates to compositions for reducing CLPTM1L expression in a cell and methods for using such compositions to treat or prevent a cancer or other condition associated with CLPTM1L over-expression. In particular, the present invention relates to compositions comprising a RNAi-inducing construct targeted to CLPTM1L and to methods of administering such compositions to a subject to treat or prevent a disease or condition associated with CLPTM1L over-expression (e.g., lung cancer). Both compositions and methods are provided herein.

BACKGROUND

Cancer is a disease that begins with mutation of oncogenes and tumor suppressor genes. Mutation of these critical genes allows for a cancer cell to evolve and ultimately results in pathogenic replication (a loss of normal regulatory control leading to excessive cell proliferation) of various given types of cells found in the human body. Tumor formation, tumor survival, and cancer metastasis require anchorage-independent growth and protection from genotoxin-induced apoptosis and anoikis. Transformed cells acquire protection from these programmed cells death processes through regulation of survival signaling.

There remains a need in the art for methods for treating or preventing cancer and, in particular, for methods which slow or curb tumor growth and prevent metastasis.

BRIEF SUMMARY OF THE INVENTION

In one aspect, the present invention provides an isolated polynucleotide. In one embodiment, the polynucleotide can comprise or consist of 19-29 contiguous nucleotides of SEQ ID NO:1. The polynucleotide can comprise or consist of a nucleotide sequence selected from the group consisting of SEQ ID NO:4, SEQ ID NO:5, SEQ ID NO:9, and SEQ ID NO:15.

In a second aspect, the present invention provides an RNAi-inducing construct. The RNAi-inducing construct can comprise or consist of a nucleotide sequence selected from the group consisting of SEQ ID NO:4, SEQ ID NO:5, SEQ ID NO:9, and SEQ ID NO:15. The construct can comprise a shRNA. The shRNA can comprise an inverted repeat of the nucleotide sequence and a loop region. The nucleotide sequence can be SEQ ID NO:4. The loop region can comprise between 3 and 24 nucleotides in length.

In another aspect, the present invention provides a vector comprising an RNAi-inducing construct comprising or consisting of a nucleotide sequence selected from the group consisting of SEQ ID NO:4, SEQ ID NO:5, SEQ ID NO:9, and SEQ ID NO:15. The construct can comprise a shRNA. The shRNA can comprise an inverted repeat of the nucleotide sequence and a loop region. The nucleotide sequence of the construct can be SEQ ID NO:4. The vector can be an adenoviral vector. The vector can be a retroviral vector. The retroviral vector can be a lentiviral vector. The lentiviral vector can be packaged into an infectious particle.

In a further aspect, the present invention provides a composition comprising an RNAi-inducing construct and a delivery agent. The RNAi-inducing construct can comprise or consist of a nucleotide sequence selected from the group consisting of SEQ ID NO:4, SEQ ID NO:5, SEQ ID NO:9, and SEQ ID NO:15. The delivery agent can be selected from the group consisting of a liposome, a cationic or non-cationic polymer, a lipid, a peptide molecular transporter, and a surfactant. The composition can further comprise a pharmaceutically acceptable diluent, excipient, or carrier. The composition can comprise a plurality of RNAi-inducing constructs whose presence within a cell results in production of a plurality of different siRNAs or shRNAs targeting at least a portion of SEQ ID NO:1.

In another aspect, the present invention provides a method of suppressing expression of a nucleic acid sequence encoding CLPTM1L in a subject. The method can comprise administering a composition of the invention to a subject. Administering can comprise introducing the composition into the subject intranasally, intravenously, or by inhalation. The composition can be administered as an aerosol. Introducing the composition into the subject intranasally, intravenously, or by inhalation can suppress expression of a nucleic acid sequence encoding CLPTM1L in cells of the subject's respiratory system.

In another aspect, the present invention provides a method of treating or preventing a disease or condition associated with over-expression or inappropriate expression of a nucleic acid sequence encoding CLPTM1L. The method can comprises administering the composition of the invention to a cell, tissue, or organ of a subject at risk of, diagnosed as having, or exhibiting a symptom of the disease or condition. Then disease or condition can be a cancer or a pre-cancerous lesion. The cancer or pre-cancerous lesion can exhibit resistance to a chemotherapeutic agent. The chemotherapeutic agent can be cisplatin. The cancer or pre-cancerous lesion can be selected from the group consisting of lung cancer, pancreatic cancer, prostate cancer, skin cancer, bladder cancer, kidney cancer, ovarian cancer, colon cancer, colorectal cancer, breast cancer, cervical cancer, brain cancer, esophageal cancer, stomach cancer, lymphoma, chronic leukemia, and acute leukemia. The composition can be administered as an aerosol. Administering can comprise introducing the composition into the subject by inhalation, by intubation, by intratumoral injection, or intranasally, intravenously, intraocularly, intraperitoneally, topically, orally, rectally, or vaginally. Introducing the composition into the subject intranasally, intravenously, or by inhalation can suppress expression of a nucleic acid sequence encoding CLPTM1L in a cell or a tissue of the subject's respiratory system, whereby the disease or condition is treated or prevented.

These and other features, aspects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

FIG. 6 depicts an evaluation of 5p genes as potential lung tumorigenesis modifiers in a shRNA/K-Ras$^{LSL-G12D/+}$ mouse model. (A) Diagram of K-Ras$^{+/LSLG12D}$ mouse model of lung tumorigenesis allowing concurrent modulation of candidate gene expression. (B) High dose group: Tumor number (left panel) and tumor load (right panel) for mice infected with virus encoding shRNA for random scrambled sequence, CLPTM1L and TERT. Black bars represent the mean. Error bars represent one standard deviation from the mean. (C) Low dose group: as in FIG. 1B. (D) Representative gross appearance of lungs from scrambled shRNA, CLPTM1L shRNA and TERT shRNA high dose groups.

FIG. 12 presents SEQ ID NO:2 (CLPTM1L, 538 AA, UniProt ID: Q96KA5.11).

FIG. 13 presents SEQ ID NO:3, primary mRNA, partial coding sequence (Genbank ID BC016399.1).

DETAILED DESCRIPTION OF THE INVENTION

Figure 1:
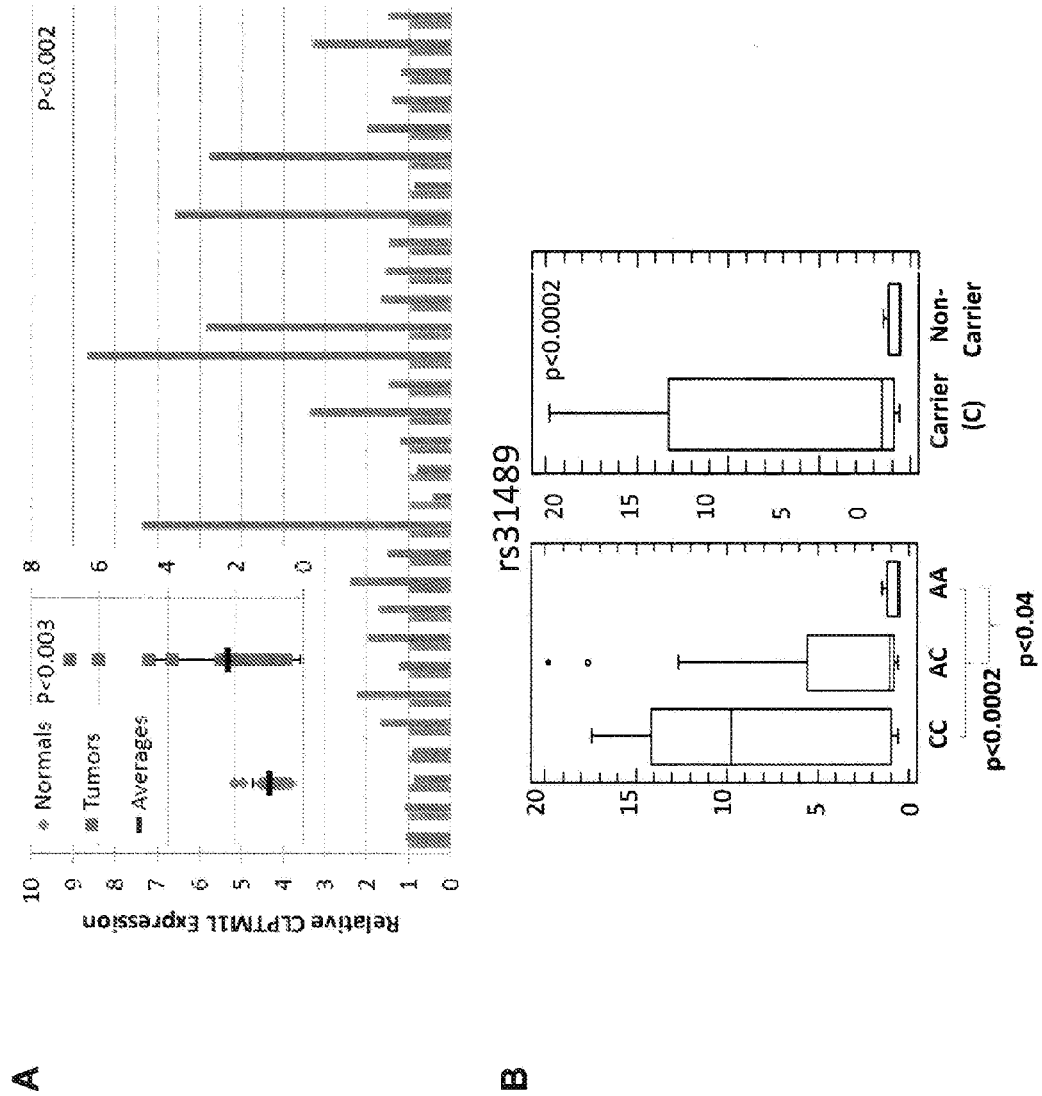
FIG. 1 presents graphs demonstrating CLPTM1L overexpression in lung adenocarcinomas and regulation of CLPTM1L in normal lung tissue by lung cancer risk variants. (A) CLPTM1L transcript accumulation in human lung adenocarcinoma tissue, expressed as relative to each paired normal adjacent tissue. P-value obtained by paired Student's T-Test. Inset: CLPTM1L transcript accumulation in human lung adenocarcinomas and adjacent normal lung tissues, expressed as relative to the average value for normal tissues. Error bars represent one standard deviation (SD) from the mean. (B) Box plots of eQTL analysis of the association of expression of CLPTM1L transcript in normal lung tissues as measured by RT-qPCR and genotype of the lung cancer associated SNP rs31489.

The present invention is based at least in part on the Inventors' discovery that depletion of CLPTM1L in mouse fibroblasts inhibited morphologic transformation and anchorage-independent growth, two processes required for oncogene-driven tumor formation. In particular, depletion of CLPTM1L in the lungs of mice using RNA interference robustly and significantly inhibited lung tumorigenesis driven by the K-Ras oncogene. The Inventors further discovered that depletion of CLPTM1L using RNA interference promoted anoikis. Tumor cells must avoid anoikis, a programmed cell death mechanism associated with detachment of tumor cells from an extracellular substrate, to invade surrounding tissue and for metastasis.

Cisplatin Resistance Related Protein-9 (CRR9), otherwise known as Cleft-Lip and Palate Transmembrane Protein-Like Protein 1 (CLPTM1L), is located at chromosome 5p15.33 as defined by multiple Genome Wide Association (GWA) studies. The CLPTM1L gene lies within a locus on chromosome 5 that is frequently gained in copy number early in lung cancer and that is associated by genotype with lung cancer susceptibility. For example, genetic variants near and within the CLPMT1L gene are associated with lung cancer, cervical cancer, ovarian cancer, pancreatic cancer, bladder cancer, glioma, prostate cancer, basal cell carcinoma, and melanoma. Although the mechanism of action remains to be fully elucidated, it is believed that CLPTM1L is involved in triggering Bcl-xL survival protein accumulation. Indeed, the Inventors' evidence demonstrates that CLPTM1L protects chemotherapeutically treated tumor cells from genotoxin-induced apoptosis. In addition, the Inventors have demonstrated that CLPTM1L is required for anchorage independent growth and for Ras-driven lung tumorigenesis.

The human CLPTM1L gene (GenBank ID AK027306; SEQ ID NO:1) encodes a 538 amino acid polypeptide (NCBI Gene ID: 81037; UniProt ID: Q96KA5.11; SEQ ID NO:2). Gene products of human CLPTM1L include a primary mRNA (Genbank ID BC016399.1; SEQ ID NO:3) and two additional predicted transcript splice variants (Ensembl transcript IDs: ENST00000320927 and ENST00000507807). These predicted splice variants encode proteins of 502 and 369 amino acids, respectively. Splice variant prediction methods are available at useast.ensembl.org/info/docs/genebuild/genome_annotation.html on the World Wide Web.

Compositions of the Invention

In one aspect, the present invention is directed to compositions comprising a construct that induces RNA interference (RNAi) for reducing or silencing expression a target gene. As used herein, the term "RNAi" refers to an evolutionarily conserved and sequence-specific gene silencing mechanism. Briefly, RNAi can be induced by double-stranded RNA that is processed by the RNase III-like enzyme Dicer into small interfering RNAs (siRNAs) of about 21 bp. The siRNA is incorporated into a RNA-induced silencing complex (RISC) in the cytoplasm and directs RISC to degrade an mRNA that is perfectly complementary to one strand of the siRNA. Accordingly, the term "RNAi-inducing construct" as used herein refers to RNA molecules and vectors whose presence within a cell triggers RNA interference and leads to reduced expression of a transcript to which the RNAi-inducing construct is targeted. The term specifically includes short interfering RNAs (siRNAs), short hairpin RNAs (shRNAs), and RNAi-inducing vectors. Generally, shRNAs comprise sense and antisense sequences which form the "stems" of the hairpin and a loop region of unpaired nucleotides that connects the two stems. As used herein, the term "RNAi-inducing vector" encompasses a vector whose presence within a cell results in transcription of one or more RNAs that self-hybridize or hybridize to each other to form an shRNA or siRNA. Generally, RNAi-inducing vectors comprise a nucleic acid operably linked to a promoter such that the vector produces one or more RNA molecules that hybridize or self-hybridize to form an siRNA or shRNA when the vector is present within a cell. When transcription of the nucleic acid operably linked to a promoter produces a siRNA or shRNA that triggers RNA interference and leads to reduced expression of a target gene of interest, the RNAi-inducing vector is considered to be targeted to transcripts of the target gene.

Figure 8:
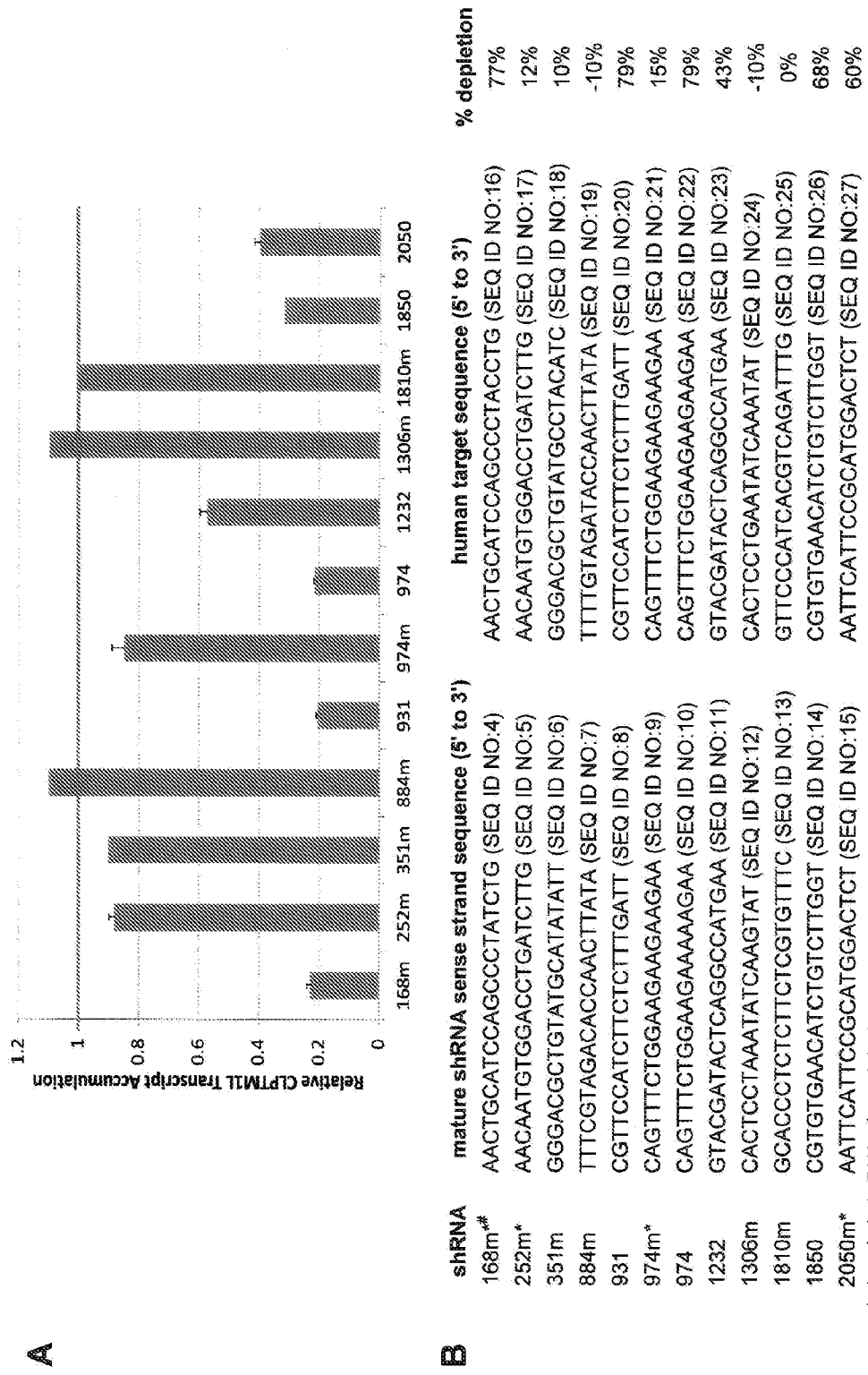
FIG. 8 presents relative CLPTM1L transcript accumulation data for several short-hairpin RNA (shRNA) constructs in a bar graph (A) and table (B). shRNA 168m (shCLP168m) has been validated in human and mouse tumor cells. The blue line (A) represents transcript level in vector controls. #=$^{#}$ validated in human and mouse tumor cells; *=modified construct design.

In some cases, RNAi-inducing constructs are siRNAs or shRNAs. For example, an RNAi-inducing construct can be a siRNA or shRNA designed to specifically target CLPTM1L transcripts. Short hairpin RNAs useful for RNAi-inducing constructs of the present invention can comprise stems of 19-29 contiguous nucleotides, and preferably 19-23 contiguous nucleotides, derived from a target sequence. In an exemplary embodiment, shRNAs useful for RNAi-inducing constructs of the present invention comprise 21-nucleotide stems derived from the target sequence. To specifically target CLPTM1L transcripts, sequence for a siRNA or shRNA provided herein can be obtained from the CLPTM1L open reading frame or the CLPTM1L 5' or 3' untranslated region (UTR). For example, Table 1 lists 21-nucleotide candidate sequences for designing CLPTM1L-targeting shRNAs. In one preferred form of the present invention, the RNAi-inducing construct comprises one of the sequences set forth in Table 1, each of which has been evaluated for efficacy (FIG. 8). Some of the constructs of Table 1 (indicated with asterisk) comprise designed sequences having modifications relative to the human target sequence.

It will be appreciated that RNAi-inducing constructs can comprise a 19-29 nucleotide stem region comprising target sequence and a loop region. Evidence suggests that the loop region sequence does not confer specificity to the shRNA but does affect processing and efficacy of shRNAs (Jensen et al., *PLoS One* 7:e43095, 2012). The loop region is preferably between 3 and 23 nucleotides in length. There is evidence that, at least in the context of a 9-nucleotide loop region, shRNA efficacy does not increase as stem length increases (Li et al., *RNA* 13:1765-74, 2007). In some cases, the loop sequence can comprise one or more restriction endonuclease sites to facilitate, for example, cloning of an RNAi-inducing construct into an expression vector. See, for review, Invitrogen, "Using siRNA for gene silencing is a rapidly evolving tool in molecular biology: siRNA Design Guidelines," available at Invitrogen.com/site/us/en/home/References/Ambion-Tech-Support/rnai-sirna/general-articles/-sirna-design-guidelines.html on the World Wide Web.

TABLE 1

Short Hairpin RNAs Targeting CLPTM1L Transcripts

| shRNA | mature shRNA sense strand sequence (5' to 3') | human target sequence (5' to 3') |
|---|---|---|
| 168m*# | AACTGCATCCAGCCCTATCTG (SEQ ID NO: 4) | AACTGCATCCAGCCCTACCTG (SEQ ID NO: 16) |
| 252m* | AACAATGTGGACCTGATCTTG (SEQ ID NO: 5) | AACAATGTGGACCTGATCTTG (SEQ ID NO: 17) |
| 351m | GGGACGCTGTATGCATATATT (SEQ ID NO: 6) | GGGACGCTGTATGCCTACATC (SEQ ID NO: 18) |
| 884m | TTTCGTAGACACCAACTTATA (SEQ ID NO: 7) | TTTTGTAGATACCAACTTATA (SEQ ID NO: 19) |
| 931 | CGTTCCATCTTCTCTTTGATT (SEQ ID NO: 8) | CGTTCCATCTTCTCTTTGATT (SEQ ID NO: 20) |
| 974m* | CAGTTTCTGGAAGAAGAAGAA (SEQ ID NO: 9) | CAGTTTCTGGAAGAAGAAGAA (SEQ ID NO: 21) |
| 974 | CAGTTTCTGGAAGAAAAAGAA (SEQ ID NO: 10) | CAGTTTCTGGAAGAAGAAGAA (SEQ ID NO: 22) |
| 1232 | GTACGATACTCAGGCCATGAA (SEQ ID NO: 11) | GTACGATACTCAGGCCATGAA (SEQ ID NO: 23) |
| 1306m | CACTCCTAAATATCAAGTAT (SEQ ID NO: 12) | CACTCCTGAATATCAAATAT (SEQ ID NO: 24) |
| 1810m | GCACCCTCTCTTCTCGTGTTTC (SEQ ID NO: 13) | GTTCCCATCACGTCAGATTTG (SEQ ID NO: 25) |
| 1850 | CGTGTGAACATCTGTCTTGGT (SEQ ID NO: 14) | CGTGTGAACATCTGTCTTGGT (SEQ ID NO: 26) |
| 2050m* | AATTCATTCCGCATGGACTCT (SEQ ID NO: 15) | AATTCATTCCGCATGGACTCT (SEQ ID NO: 27) |

*short-hairpin RNA of novel design
validated in human and mouse tumor cells

An RNAi-inducing construct as described herein can target transcripts of additional genes. In some cases, an RNAi-inducing construct can target a gene having an established association between over-expression and cancer risk or diagnosis of a cancer or pre-neoplastic lesion. The present invention is not intended to be limited to target transcripts that are over-expressed in tumor cells. Indeed, non-overexpressed genes can be viable targets for the methods provided herein. For example, a functional mutation in a gene can be associated with cancer but is not associated with up-regulated or down-regulated gene expression.

It will be appreciated that in vivo expression of RNAi-inducing constructs appropriate for inclusion in compositions described herein can be accomplished by introducing the constructs into a vector such as, for example, a DNA plasmid or viral vector, and introducing the vector into cells of the subject. For example, in a clinical trial (government ID NCT01505153), a plasmid-based shRNA conjugated to a lipid vesicle was administered to human subjects by intratumoral injection. Phase II of this clinical trial involved intradermal injections of a whole cell vaccine derived from autologous tumor cells transfected with a shRNA specifically targeting Furin gene products. Any appropriate vector that achieves the intended purpose or is deemed appropriate by those of skill in the art can be used. For example, it will be desirable in some cases to select a vector that can deliver the RNAi-inducing construct to one or more cells in the subject's lungs. In some cases, a gene therapy vector can be used for the delivery of the RNAi-inducing construct to a subject's cells.

In some cases, it may be advantageous to simultaneously introduce or "multiplex" multiple RNAi-inducing constructs to a target cell, tissue, or organ. For example, multiple gene-specific siRNA sequences can be delivered within a single construct. See, for example, Shin et al., *RNA* 15:898-910, 2009. A multiplex siRNA/shRNA strategy can be advantageous for treating or preventing a disease or condition associated with relatively rapid emergence of point mutations or other minor sequence variations sufficient to overcome the sequence-specificity of RNAi. It will be generally understood by those practicing in the art that multiplexed siRNAs retain comparable efficacy to that exhibited by their individual counterparts. Other mechanisms for treating or preventing a disease or condition associated with RNAi "escape" by virtue of sequence mutations include, without limitation, developing new RNAi-inducing constructs to target specific escape variants, and using tandem siRNA transcripts in an extended hairpin RNA from which several functional siRNAs can be produced (Liu et al., *Nuc. Acids Res.* 35(17):5683-93, 2007), and using long hairpin RNAs from which siRNAs targeting multiple sequences can be obtained (Konstantinova et al., *Gene Therapy* 13:1403-13, 2006).

It will be appreciated that it may be desirable to achieve prolonged in vivo expression of siRNAs or shRNAs from RNAi-inducing vectors delivered according to the present invention. For example, methods for treating or preventing a disease or condition may be most efficacious if RNAi-inducing vectors produce siRNAs or shRNAs over long periods of time (e.g., more than a few days, more than a few weeks, more than a few months, at least a year or longer). In such cases, it may be preferable to use a retroviral vector (e.g., a lentiviral vector) to achieve transcription of stably integrated nucleotide sequences that self-hybridize or hybridize to each other to form an shRNA or siRNA that inhibits expression of at least one targeted transcript in the cell. For example, lentiviral expression vectors contain the genetic elements required for packaging, transduction, stable integration of the viral expression construct into genomic DNA, and expression of the siRNA or shRNA. Lentiviral vectors appropriate for use according to the present invention are known in the art. See, for example, Rubinson et al., *Nature Genetics* 33:401-406 (2003). In a clinical trial (government ID NCT01301443), a lentiviral vector intended to confer stable expression of angiostatin and endostatin was delivered to human subjects by single, subretinal injections at increasing doses as a treatment for age-related macular degeneration.

Selection of an appropriate retroviral vector can depend on the target cell, tissue, or organ of interest. For example, HIV-based lentiviral vectors efficiently infect stem cells and primary cells (e.g., HUVEC, bone marrow, adipose), while FIV-based lentiviral vectors are known to efficiently infect well-known mouse cell lines (e.g., P19, NB41, NIH3T3, P38) and various human cell lines. Pseudotyped lentiviral vectors are capable of infecting a variety of other cell types including, for example, neuronal, dendritic, endothelial, retinal, ovarian, pancreatic, hepatic, aortic smooth muscle cells, airway epithelia, skin fibroblasts, and macrophages. Lentiviral vectors also have been used to direct in vivo delivery and expression of transgenes in muscle, brain, airway epithelium, liver, pancreas, retina, and skin.

In some cases, a retroviral vector (e.g., lentiviral vector) can be introduced into a cell as a "naked" or unpackaged plasmid for transient expression of siRNAs or shRNAs from RNAi-inducing vectors delivered according to the present invention. Transient expression also can be achieved using an adenoviral vector.

In other cases, it may be advantageous to package a vector in a pseudoviral particle to achieve more efficient transduction and stable expression of an RNAi-inducing construct as provided herein in a cell, tissue, or organ. For example, a lentiviral vector can be packaged into a lentiviral particle (e.g., a lentivirus capable of infecting cells) using a lentiviral expression system. Lentiviral expression systems comprise the lentiviral vector, a packaging plasmid comprising the necessary components for transcription and for packaging of an RNA copy of the expression construct into recombinant pseudoviral particles, and a pseudoviral particle producer cell line (e.g., 293T cells, HEK 293 cells). For example, HIV-based and FIV-based lentivector expression systems are known and available in the art. In an exemplary embodiment, a pLKO.1-based lentiviral expression vector encoding a short hairpin RNA targeted to CLPTM1L can be used with a packaging plasmid such as, for example, pCMV-dR8.2 dvpr, pMD2,G, or any other viable combination of packaging plasmids to package a lentiviral vector into infectious lentiviral particles. In some cases, a lentivirus expression vector can be targeted to a specific tissue type by incorporating, for example, a fusogenic polypeptide on the viral surface. See, for example, Yang et al., *Proc Natl Acad Sci USA* 103:11479-84, 2006 (demonstrating specific transduction of CD20-presenting cells using a fusion-competent protein that incorporates into the viral envelope). In other cases, a viral vector can be "pseudotyped" with one or more glycoproteins on the viral surface to modify or expand the range of cell types that the virus can transducer.

Compositions provided herein can include one or more agents to facilitate delivery of RNAi-inducing constructs to a target cell, tissue, or organ or into the bloodstream of a subject to increase bioavailability; and to promote intracellular uptake. For example, a composition provided herein can comprise an RNAi-inducing construct and a delivery agent capable of facilitating delivery of the RNAi-inducing construct to a cell, tissue, organ, or system (e.g., circulatory system) of a subject (e.g., human). As used herein, "delivery" encompasses transporting an RNAi-inducing construct (e.g., shRNA) into the body, to a target cell, tissue, organ, or system (e.g., circulatory system) in the body, and into a cell via cellular uptake of the construct. In some cases, a delivery agent acts as a vehicle or carrier for the RNAi-inducing construct. Accordingly, a delivery agent appropriate for a composition provided herein can be a liposome, a cationic or non-cationic polymer, a lipid, a peptide molecular transporter (e.g., HIV tat peptide), or a surfactant. In an exemplary embodiment, a liposome, a cationic or non-cationic polymer, a lipid, a peptide molecular transporter (e.g., HIV tat peptide), or a surfactant is used as a delivery agent to deliver a siRNA or shRNA described herein. In what is believed to be the first clinical trial of inducing RNAi in a human by administering siRNA, 21-mer siRNA were administered by intravenous injection of siRNAs bound to cyclodextrin-based polymer nanoparticles (Davis, *Nature* 464(7291):1067-1070, 2010). In some cases, a viral vector is used to delivery an RNAi-inducing construct provided herein. Viral vectors, at least in part, provide their own stability and delivery mechanisms.

Compositions provided herein can comprise at least one pharmaceutically acceptable diluent, excipient, or carrier. As used herein, "pharmaceutically acceptable carrier" refers to any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. In some cases, diluents and carriers appropriate for an inhaled composition as provided herein can include, without limitation, saline, gelatin, glycerin, dimethyl sulfoxide (DMSO), ethanol, and polyethylene glycol. Carrier gases appropriate for an inhaled composition as provided herein can include, without limitation, air, helium, oxygen, and xenon, or a mixture thereof. In some cases, aerosol or nanodroplet generating technologies such as a jet nebulizer, vibrating mesh nebulizer, ultrasonic wave nebulizer, human powered nebulizer, atomizer, dry powder inhaler, or mist inhaler can be used to obtain a composition for inhalation. Aerosols can be passed through "scrubbers" to remove diluents before delivery.

In some cases, it may be advantageous to control expression of an RNAi-inducing construct. Off-target side effects or off-target expression can be limited or avoided through spatial or temporal control of shRNA or siRNA expression (i.e., conditional expression). For example, conditional expression of a shRNA or siRNA can be achieved by driving expression of an RNAi-inducing construct with a drug-responsive promoter (e.g., a doxycycline-responsive promoter, an ecdysone-responsive promoter). In some cases, a viral vector described herein can be modified to include a drug-responsive promoter for conditional expression.

Methods of Using Compositions of the Invention

In one aspect, the present invention is directed to methods of treating or preventing a disease or condition in a subject by inhibiting expression of CLPTM1L in a subject. For example, the present invention provides methods comprising administering a composition comprising an RNAi-inducing construct targeted to CLPTM1L to a subject. As used herein, the term "subject" refers to an individual having, suspected of having, or susceptible to having a disease or condition associated with over-expression of CLPTM1L or for which there is a genetic association with CLPTM1L (e.g., a disease or condition associated with a gain in CLPTM1L locus copy number or a genotype for susceptibility to the disease or disorder). Subjects can include mammals such as, for example, humans, non-human primates, and wild or domesticated animals.

As used herein, the terms "treating," "treat," and "treatment" refer to the management and care of a patient for the purpose of combating the disease, condition, or disorder. The terms embrace both preventative, i.e., prophylactic, and palliative treatments. In some cases, the term "treated" refers to any beneficial effect on progression of a disease or condition. Beneficial effects can include reversing, alleviating, inhibiting the progress of, preventing, or reducing the likelihood of the disease or condition to which the term applies or one or more symptoms or manifestations of such a disease or condition. Where the disease or condition is a cancer or cancer-associated condition, treating can refer to the management and care of a patient for the purpose of combating cancer, and can include reversing, alleviating, inhibiting the progress of, preventing, or reducing the likelihood of, or lessening the severity of any aspect of the cancer or cancer-associated condition (e.g., metastasis, tumor growth). As used herein, the terms "preventing" and "prevent" refer not only to a complete prevention of a certain disease or condition, but also to partially or substantially attenuating, reducing the risk of, or delaying the development or recurrence of the disease or condition to which the term applies.

In some cases the methods provided herein are directed to treating or preventing a cancer in a subject by administering a composition provided herein. In other cases, the present invention provides a method of inhibiting, retarding, or preventing growth of a tumor or tumor cells in a subject. In an exemplary embodiment, the method comprises administering a composition comprising an RNAi-inducing construct targeted to CLPTM1L to a subject.

The methods provided herein are appropriate for treating or preventing any type of disease or condition associated with over-expression of CLPTM1L or any disease or condition for which there is a genetic association with CLPTM1L (e.g., a disease or condition associated with a gain in CLPTM1L locus copy number or a genotype for susceptibility to the disease or disorder). In an exemplary embodiment, a method provided herein is for the treatment or prevention of a cancer, tumor, or pre-neoplastic lesion (e.g., pre-cancerous lesion). Examples of cancers appropriate for methods of treating or preventing as provided herein include, without limitation, lung cancer, pancreatic cancer, prostate cancer, skin cancer, bladder cancer, kidney cancer, ovarian cancer, colon cancer, colorectal cancer, breast cancer, cervical cancer, brain cancer, esophageal cancer, and stomach cancer. Other diseases or conditions appropriate for methods of treating or preventing as provided herein include, without limitation, lymphoma and chronic and acute leukemia.

In some cases, a method provided herein can be practiced to treat or prevent a disease or condition in a subject, where the disease or condition exhibits chemotherapeutic drug resistance. For example, a subject can be diagnosed or identified as having a disease or condition such as cancer that exhibits resistance to a chemotherapeutic agent such as cisplatin. CLPTM1L has been found to be highly expressed in cisplatin resistant ovarian tumor cell lines. Moreover, CLPTM1L appears to be anti-apoptotic under genotoxic conditions. Examples of cancers for which treatment involves administering cisplatin include lung cancer, colorectal cancer, NSCLC, bronchioloaviolar cell lung cancer, bone cancer, pancreatic cancer, skin cancer, cancer of the head or neck, cutaneous melanoma, intraocular melanoma, uterine cancer, ovarian cancer, rectal cancer, anal region cancer, stomach cancer, gastric cancer, colon cancer, breast cancer, uterine cancer, fallopian tube carcinoma, endometrial carcinoma, cervical carcinoma, Hodgkin's Disease, esophagus cancer, small intestine cancer, endocrine system cancer, thyroid gland cancer, parathyroid gland cancer, adrenal gland cancer, soft tissue sarcoma, prostate cancer, bladder cancer, kidney cancer, renal cell carcinoma, renal pelvis carcinoma, mesothelioma, hepatocellular cancer, biliary cancer, chronic leukemia, acute leukemia, lymphocytic lymphoma, CNS neoplasm, spinal axis cancer, brain stem glioma, glioblastoma multiforme, astrocytoma, schwannoma, ependymoma, medulloblastoma, meningioma, squamous cell carcinoma and pituitary adenoma tumors or tumor metastases.

In some cases, a method provided herein can be practiced to treat or prevent a cancer associated with a mutation, translocation, amplification, or deletion of at least a portion of at least one of the following: K-Ras, H-Ras, N-Ras, RASSFI, PI3KCA, PTEN, EGFR, FGFR1, PDGFRA, BRAF, AKL, ROS1, BCL-x, BIM, BAD, BAX, AKT, and mTOR. In an exemplary embodiment, a method provided herein can be practiced to treat or prevent a cancer for which at least one of these genes suspected of being or demonstrated to be regulated by CLPTM1L.

In some cases, a method provided herein can be practiced to treat or prevent a cancer previously or currently being subjected to radiation therapy (i.e., therapy involving high-energy radiation) or to chemotherapy using a chemotherapeutic agent such as, for example, an alkylating agent, a cross-linking agent, an anti-metabolite, an antibiotic, a topoisomerase inhibitor, or a mitotic inhibitor. The method also can be practiced to treat or prevent a cancer if use of such a therapeutic agent is anticipated. For example, a method provided herein can be appropriate to treat or prevent a cancer for which depletion of CLPTM1L sensitizes the cancer cells to DNA damage-induced apoptosis. As used herein, the terms "sensitize" and "sensitized" refers to cells made more responsive to an agent, a treatment, an environment, a stimulus, or a condition. For example, a "sensitized" cell can exhibit an increase in the magnitude of said response or an increase in any type of response. In an exemplary embodiment, cancer cells exhibit increased apoptosis when sensitized to DNA damage by the depletion of CLPTM1L according to a method provided herein.

In some cases, a method provided herein can be practiced to treat or prevent a cancer suspected of being or demonstrated to be refractory to one or more chemotherapeutics such as, for example, an alkylating agent, a cross-linking agent, an anti-metabolite, an antibiotic, a topoisomerase inhibitor, or a mitotic inhibitor. For example, a method provided herein can be appropriate to treat or prevent a cancer for which depletion of CLPTM1L sensitizes the cancer cells to cytotoxic treatment with a cross-linking agent and a topoisomerase inhibitor.

Methods of treating or preventing cancer as provided herein can be practiced at any appropriate time. In some cases, a composition comprising an RNAi-inducing construct targeted to CLPTM1L as provided herein is administered to a subject following diagnosis of a cancer or a pre-neoplastic lesion (e.g., pre-cancerous lesion) in a biological sample from the subject or, in other cases, following identification of copy number gain or expression of CLPTM1L above a threshold that is empirically determined to constitute cancer risk. Determination of such a threshold includes analysis of current and future data correlating CLPTM1L expression in normal tissue with incidence of a cancer. With respect to lung tissue, a threshold that is empirically determined to constitute cancer risk can be at least 2-fold greater average expression for one or more test lung tissue samples relative to the average expression in a healthy sample taken from surrounding tissue. In some cases, treatment may be indicated if it is determined that expression of CLPTM1L is higher in a test sample (e.g., tissue suspected of comprising cancer cells) compared to tissue surrounding the sampled tissue. In other cases, a composition comprising an RNAi-inducing construct targeted to CLPTM1L is administered to a subject upon identification of one or more risk factors for the development of cancer or following identification of a genotype associated with a cancer in a biological sample from the subject. To prevent or slow tumor formation, a composition comprising an RNAi-inducing construct targeted to CLPTM1L as provided herein is administered to a subject prior to or in the absence of a cancer or pre-neoplastic lesion. In such cases, the composition is administered as a preventative agent.

Treatment or prevention according to a method provided herein can occur before, during, or after the subject is treated by surgery, radiation, and/or chemotherapy. In some cases, treatment according to a method provided herein prior to chemo- or radiotherapy may improve the outcome of the conventional therapy. In an exemplary embodiment, a composition comprising an RNAi-inducing construct targeted to CLPTM1L is administered concurrently with one or more other treatments or preventative measures such as radiotherapy, chemotherapy, or surgery.

A composition comprising an RNAi-inducing construct targeted to CLPTM1L as provided herein can be administered to a subject by any method that achieves the intended purpose or is deemed appropriate by those of skill in the art. For example, the composition is administered by one or more of the following modes of administration: inhalation (e.g., using an aerosol, nebulizer, atomizer, or inhaler), intravenous, intubation, intratumoral injection, intraocular, intraperitoneal, topical (e.g., in a cream, ointment, or drop formulation), oral, rectal, or vaginal. The mode of administration can be determined based on the physical location of a tumor or tumors in the subject's body. In exemplary embodiments, a composition as described herein is administered by inhalation or intravenous injection. For example, a composition comprising an RNAi-inducing construct targeted to CLPTM1L as provided herein can be administered to a subject having a diagnosis of lung cancer, where the composition is inhaled or injected intravenously to reach the target cells.

Compositions can be administered to a subject in need thereof in dosage unit form where each discrete dosage unit contains a predetermined quantity of an active ingredient or compound that was calculated to elicit a desirable therapeutic effect when administered with, in some cases, a pharmaceutically acceptable carrier. For dosage determinations, it can be advantageous to assess toxicity and therapeutic efficacy of a compound in cell cultures or in experimental animals. For example, the $LD_{50}$ (i.e., the dose lethal to 50% of the population) and $ED_{50}$ (i.e., the dose therapeutically effective in 50% of the population) can be determined. From these calculations, dosage ranges for use in humans can be formulated. Dosage ranges can vary depending on factors such as mode of administration. A therapeutically effective amount of a pharmaceutical composition can range from about 0.001 to 30 mg/kg body weight (e.g., about 0.01 to 25 mg/kg body weight; about 0.1 to 20 mg/kg body weight; about 1 to 10 mg/kg body weight).

In some cases, an appropriate dose of a pharmaceutical composition as provided herein can be from about 1000 functional viral particles up to the maximum tolerated dose regardless of the mode of administration. An appropriate dose for small inhibitory RNA with carrier can be from 0.005 mg/kg up to a maximum tolerated dose. In some cases, an appropriate dose of a pharmaceutical composition as provided herein can be determined according to body surface area of a subject, calculated using the subject's height and weight, to whom the composition will be administered. In such cases, a dose can be provided as a particular amount of the composition per $m^2$ (e.g., $mg/m^2$). In some cases, an appropriate dose can be between approximately 10 $mg/m^2$ and approximately 40 $mg/m^2$ of an RNAi-inducing construct. When converted to milligrams (mg) per kilogram (kg) of a subject's body weight, a dose of 15 $mg/m^2$ is the same as about 0.4 mg/kg. See Freireich et al., *Cancer Chemotherapy Rep.* 50(4):219-244 (1966). Additional information about dosage calculation can be found in Center for Drug Evaluation and Research, Center for Biologics Evaluation and Research (2002), *Estimating the safe starting dose in clinical trials for therapeutics in adult healthy volunteers*, U.S. Food and Drug Administration Rockville, Md., USA.

It will be understood that mass of an RNAi-inducing construct as provided herein can refer to mass of the construct plus the delivery agent or pharmaceutically acceptable carrier, if applicable. Where "naked" siRNAs or shRNAs are administered without a carrier, grams of the siRNA or shRNA can be divided by the molecular weight of the siRNA or shRNA molecule to determine moles of the molecule. In some cases, dosages and dosage ranges appropriate for a composition provided herein can be determined using pharmacokinetic (i.e., drug metabolism and clearance) data.

Clinicians, physicians, and other health care professionals can administer a composition to a subject in need thereof according to a method provided herein by a physician or other health professional. In some cases, a single administration of the composition may be sufficient. In other cases, more than one administration of the composition is performed at various intervals (e.g., once per week, twice per week, daily, monthly) or according to any other appropriate treatment regimen. The duration of treatment can be a single dose or periodic multiple doses for as long as administration of a composition provided herein is tolerated by the subject.

Any appropriate method can be practiced to determine, detect, or monitor a subject's response to treatment according to a method provided herein. As used herein, "determining a subject's response to treatment" refers to the assessment of the results of a therapy in a subject in response to administration of a composition provided herein or to treatment according to a method provided herein. For example, a subject's condition can be monitored continuously or evaluated at appropriate time intervals (e.g., at regular or irregular time points) to detect and/or monitor any changes in disease progression (e.g., change in tumor size) as an indicator of the subject's response to a composition comprising an RNAi-inducing construct targeted to CLPTM1L. In some cases, tumors can be measured to detect or monitor any change in, for example, tumor size or tumor growth rate (e.g., tumor expansion or shrinkage, inhibited or accelerated tumor growth rate). For example, detection methods such as computed tomography (CT), magnetic resonance imaging (MRI) scanning, and x-ray (e.g., chest x-ray) can be used. In some cases, ultrasound examinations can be used to detect and measure tumor regression or to detect progression of lesions. In other cases, evaluation of a tumor or pre-neoplastic lesion can involve cytology or histology of, for example, biopsy samples. For solid tumors, evaluation of a subject's response to treatment as provided herein can include assessing RECIST ("Response Evaluation Criteria in Solid Tumors"). RECIST criteria can be used to evaluate a subject's response to the therapy used to treat their disease or condition. See, for review, Therasse et al., *J. Natl. Cancer Inst.* 92:205-16, 2000.

In some cases, biomarkers (e.g., mRNA, protein) can be used to detect or monitor the efficacy of a treatment or prevention method described herein. In an exemplary embodiment, use of a biomarker can comprises a) administering a composition provided herein; b) determining the levels of a biomarker according to the present invention in one or more biological samples taken from the subject at different time points (before, during and/or after administration); and c) comparing the determinations made for the biological samples obtained during a particular phase of treatment and comparing them to controls or to levels determined for the subject's samples obtained at different phases of treatment. For bone and blood tumors, evaluation using biomarkers can include detecting or monitoring expression levels for one or more tumor markers and assessing hematologic indicators including, for example, mean platelet volume, platelet counts, leukocyte counts, and hemoglobin level. Other indicators or "efficacy markers" of a positive outcome following administration of a composition comprising an RNAi-inducing construct targeted to CLPTM1L according to a method provided herein can include (1) reduced CLPTM1L transcript and/or protein levels in tumors or target tissues and (2) reduced phosphorylated Akt or Bcl-xL protein levels in tumors or target tissues. These efficacy markers can be determined by biopsy, aspirate, or lavage followed by, in an exemplary embodiment, an appropriate diagnostic test such as PCR, Western blotting, immunohistochemistry using specific antibodies. A positive result for any of the outcome criteria or evaluation methods described herein is indicative of the method's efficacy for treating or preventing the subject's disease or condition.

Indicators of a positive response to administration of a composition comprising a RNAi-inducing construct targeted to CLPTM1L according to a method provided herein can include, for example, a significant decrease in CLPTM1L transcript and/or CLPTM1L protein levels in tumors or target tissues relative to pre-treatment levels or to untreated samples (e.g., expression reduced to approximately 60%-80% of expression in a control sample). In some cases, an indicator of a positive response to administration of a composition comprising a RNAi-inducing construct targeted to CLPTM1L can be significantly reduced levels of phosphorylated Akt and/or Bcl-xL proteins in tumors or target tissues relative to pre-treatment levels or to untreated samples or a significant increase in apoptosis in tumors or target tissues relative to pre-treatment levels or to untreated samples. According to RECIST criteria, a partial response to treatment can be indicated by at least a 30% decrease in the sum of the longest diameter of a target lesions, taking as reference the baseline sum longest diameter, and a complete or substantially complete response to treatment can be indicated by the complete or nearly complete disappearance of all target lesions relative to measurements obtained for the subject prior to treatment (i.e., baseline measurement) or relative to a control or a comparative decrease in disease progression. In some cases, response to treatment is evaluated relative to one or more subjects who were not administered a composition described herein. Other parameters for evaluating a subject's response to treatment according to a method provided herein include detecting a comparative decrease in metastatic growth; detecting any improvement in RECIST criteria for solid tumors; documenting short-term or long-term survival; documenting disease-free survival; detecting increased or decreased expression of tumor markers; detecting hematologic changes for blood and bone cancers; detecting or monitoring positive or negative responses to radiotherapy and/or chemotherapy; and detecting an increase or decrease in recurrence of the treated disease or condition. In some cases, a subject treated according to a method provided herein may exhibit signs of stable disease, where there is neither sufficient shrinkage to qualify for partial response nor sufficient increase to qualify for progressive disease, taking as reference the smallest sum longest diameter since the treatment started (Therasse et al., supra).

The determination of the response of a subject to a specific therapy can be determined using any assessment criterion used in oncology and known by persons skilled in the art. Assessment parameters useful for describing progression of a disease include: disease-free progression which, as used herein, describes the ratio of subjects in complete remission who have not had disease relapse during the time period under study; objective response, which, as used in the present invention, describes the ratio of subjects treated in whom a complete or partial response is observed; tumor control, which, as used in the present invention, relates to the ratio of people treated in whom a complete response, partial response, minor response or stable disease 6 months is observed; progression-free survival which, as used herein, is defined as the time from the beginning of the treatment until the first measurement of cancer growth. In a preferred embodiment, the response of a subject is determined by means of a parameter selected from time to progression and survival. In an exemplary embodiment, a subject's response to a treatment or preventative method provided herein should be statistically significant. The determination of whether a response is statistically significant can be carried out using statistical evaluation tools such as confidence intervals, determination of the p value, Student's t-test, Mann-Whitney test, etc. Preferred confidence intervals are at least 50%, at least 60%, at least 70%, at least 80%, at least 90%, at least 95%. Preferably, p values are 0.2, 0.1, or 0.05.

EXAMPLES

Example 1

Modulating CLPTM1L Expression

Materials and Methods
Cell Culture, Knockdown and Overexpression:
Spon8 cells were cultured in RPMI1640 plus 2% FBS (Invitrogen, Carlsbad, Calif.). Cells were transduced with lentiviral short-hairpin RNA (shRNA) vectors based on the pLKO.1 vector and designed to specifically target human CLPTM1L transcript (Sigma, St. Louis). Empty vector or vector knocking down CLPTM1L transcript were first packaged in 293T cells (Orbigen, San Diego, Calif.) by transfection with helper plasmids using Lipofectamine LTX (Invitrogen, Carlsbad, Calif.) and then transduced into Spon 8 cells with 8 µg/ml Polybrene (Sigma, St. Louis, Mo.). Media was replaced 24 hours after transduction, and cells were split 1:4 48 hours after transduction. At 72 hours post transduction, cells harboring lentiviral constructs were selected with 1 g/mL puromycin for 2-4 days, until mock infected cells were dead. Surviving cells were pooled. 3T3 cells were transfected using Lipofectamine LTX with pBABE:empty vector or pBABE:H-RasV12, pLKO.1:vector or pLKO.1:shCLP-2. Authenticated NIH3T3 cells were obtained from ATCC within the past 6 months. Spon8 cells were developed at Ohio State University in 1996 and are characterized in McDoniels-Silvers et al., *Exp Lung Res.* 27:297-318 (2001) and Herzog et al., *Oncogene* 13:1885-91 (1996). These cells are periodically authenticated based on the molecular profile described in therein.

RT-Quantitative Real-Time PCR:
Patient matched tumor and tumor-adjacent normal RNA samples were obtained from the Tissue Procurement Core at Washington University in St. Louis under protocol approved by the Institutional Review Board at Washington University in St. Louis School of Medicine, Human Research Protection Office. Written consent was obtained from all patients participating in this tissue bank. RNA was isolated from cell lines using Tri-zol reagent and protocols (Invitrogen, Carlsbad, Calif.). Quantitative real-time PCR (qPCR) was conducted using the method as described previously (Chaparro, Wen et al. 2005). Briefly, one microgram of total RNA per sample was converted to cDNA using the SuperScript First-Strand Synthesis system for RT-PCR (Invitrogen, Carlsbad, Calif.). Quantitative RT-PCR assay was done using the SYBR Green PCR Master Mix (Applied Biosystems, Foster City, Calif.). One microliter (µL) of cDNA was added to a 25 µL total volume reaction mixture containing water, SYBR Green PCR Master Mix, and primers. Each real-time assay was done in duplicate on a BioRad MyIQ machine. Data were collected and analyzed with Stratagene Mx3000 software. The β-actin gene (Actb) was used as an internal control to compute the relative expression level ($\Delta$CT) for each sample. Primer set efficiency and linearity was calculated, and normalization was performed in accordance with MIQE guidelines. The fold change of gene expression in tumor tissues as compared to the paired normal tissues was calculated as 2d, where d=ΔCT normal–ΔCT tumor. P-values were determined using a two-tailed Student's T-Test.

Western Blotting:

The indicated cell lines were treated with cisplatin at the indicated concentrations on 6-well plates for 72 hours. Cells were lysed with 100 µl of 1× NP40 lysis buffer containing proteinase inhibitors, sheared 10 times with a 28 gauge needle, spun at 16,000×g for 30 minutes, normalized by protein concentration as determined by the Bradford method, and the supernatant boiled for 5 minutes. 20 µl of normalized lysate was resolved by SDS-PAGE and immunoblotting analyzed with indicated antibodies. The following antibodies were used: rabbit anti-CLPTM1L (Novus Biologicals, Littleton, Colo.), mouse anti-Actin (Santa Cruz Biotechnology, Santa Cruz, Calif.), mouse anti-Bcl2 clone 124 (Dako, Carpinteria, Calif.), rabbit anti-Bax #2774 (Cell Signaling, Boston, Mass.), mouse anti-p53 (Ab-1) (Oncogene, San Diego, Calif.), Bcl-xL-rabbit Bcl2L1 (AbCam, Cambridge, Mass.), rabbit anti-H-Ras (Novus Biologicals, Littleton, Colo.), mouse anti-K-Ras(BD Transduction Labs, Franklin, N.J.), anti-Akt(Cell Signaling, Boston, Mass.), antipAKT (Thr308)(Cell Signaling, Boston, Mass.), rabbit anti-PIK3C3 (Cell Signaling, Boston, Mass.), rabbit anti-BAD(AbCam, Cambridge, Mass.). Quantitation of Western analyses of three independent cultures was done using Image J software available online from the National Institutes of Heath at rsbweb.nih.gov on the World Wide Web.

Co-Immunoprecipitation:

Antibodies for bait proteins (PIK3C3, CLPTM1L and Actin, described above) were immobilized covalently using amino-link columns from Pierce Co-Immunoprecipitation Kit, (Peirce, Thermo Scientific, Rockford, Ill.) according to manufacturer's protocol. Lysates were obtained, cleared on agarose resin and immunoprecipttated according to the protocol. Western blotting for PI3K or CLPTM1L was performed on IP eluates as described above. Immobilized Actin antibody was used as irrelevant bait. IP column flow through with no bait antibody was run as an input control.

Viability Assay:

Cells stably expressing shRNA vectors as described above were seeded onto 12-well tissue culture dishes at equal densities of approximately 50% in triplicate. After attachment overnight followed by 48 hours of treatment with the indicated concentrations of cisplatin (Sigma, St. Louis, Mo.) dissolved in media. DMSO concentrations in culture media were kept consistent and were at or below 0.08%. Cell viability was measured by Cell Titer 96 Aqueous One Solution Cell Proliferation Assay (MTS) in triplicate. P-values were determined by one-tailed Student's T-Test.

The shRNA/K-RasLSL-$^{G12D/+}$ Mouse Model of Lung Tumoriqenesis:

Mouse experiments were conducted as described by DuPage et al., *Nat. Protoc.* 4:1064 (2009), with the following modifications. pLKO.1 empty shRNA vector was obtained from Open Biosystems (Foster City, Calif.). Short hairpin inserts were designed to specifically target transcripts. Oligos were ordered from IDT (Coralville, Iowa). Complimentary oligos were heated to 95° C., cooled to room temperature overnight and ligated into digested pLKO.1. Validated constructs used in mouse experiments had the following short-hairpin sequences:

shTERT1 F:
(SEQ ID NO: 28)
5'-CCGGAAGTCTGCCGTTGCCCAAGAGCTCGAGCTCTTGGGCAACGGCA
GACTTTTTTT-3' shTERT1 R:
(SEQ ID NO: 29)
5'-AATTAAAAAAACTGCATCCAGCCCTATCTGCTCGAGCAGATAGGGCT
GGATGCAGTT-3' shCLP2 F:
(SEQ ID NO: 30)
5'-CCGGAACTGCATCCAGCCCTATCTGCTCGAGCAGATAGGGCTGGATG
CAGTT TTTTT-3' shCLP2-R:
(SEQ ID NO: 31)
5'-AATTAAAAAAACTGCATCCAGCCCTATCTGCTCGAGCAGATAGGGCT
GGATGCAGTT-3'

Vectors were modified by replacing the PGK promoter and puromycin resistance orf with the CMV promoter driving expression of CRE-GFP. CMV promoter was sub-cloned from pLenti CMV GFP Puro plasmid #17448 (Addgene) and CRE-GFP was sub-cloned from pCAG:CRE-GFP plasmid #13776 (Addgene). Virus was packaged in 293T cells and functionally titered by infecting 3TZ cells (LSL-LacZ), which express LacZ upon Cre recombinase activation. Mice were anesthetized with 200 µL Avertin (40 µg/ml). $10^{-4}$ or $10^{-3}$ active virus particles in 50 µl of phosphate buffered saline was delivered via intratracheal intubation using a 22-gauge IV catheter under general anesthesia to 10 transgenic mice per group (LSL-K-RasG12D (Mouse Models of Human Cancers Consortium (MMHCC) Strain 01XJ6, Jackson Laboratory #008179 (B6), #008180 (129)). After 24 weeks, mice were anesthetized and euthanized by cervical dislocation. The thoracic cavity was surgically opened to expose the lungs. The trachea was cannulated with a 22G catheter and lungs were inflated with Tellyesniczky's solution (70% ethanol, 2% formaldehyde, and 5% acetic acid) at 25 cm of pressure by gravity. Lungs were fixed overnight and the solution was exchanged to 70% ethanol the next day. Lungs were photographed, lobes were separated and cleaned. Tumors were counted and measured with digital calipers. A cutoff for visible tumors of 0.2 mm diameter was used. Tumor volume was determined by the following formula: $A=4/3\pi r^3$. P-values were determined using a two-tailed Student's T-Test.

Kinetic Growth Assays:

Cells were harvested by trypsinization, counted on a Countess automated cell counter (Invitrogen, Carlsbad, Calif.) and plated at 1000 cells per well on 96 tissue culture plates in 8 replicates. Photomicrographs were taken every hour using an Incucyte live cell imager (Essen Biosciences, Ann Arbor, Mich.) and confluence of the cultures was measured using Incucyte software (Essen Biosciences, Ann Arbor, Mich.) over 96 hours in culture.

Transformation Assays:

NIH3T3 cells acquired within the last 6 months from ATCC were cultured in DMEM 10% FBS to 80% confluence before co-transfecting with the indicated expression and shRNA vectors using Lipofectamine LTX (Invitrogen, Carlsbad, Calif.). Cells were split, allowed to attach and placed on puromycin selection for 3 days or until mock transfected cells were dead. Cells were plated at the indicated densities and fed as needed. For whole plate staining, cells were fixed in cold methanol and stained with crystal violet. For anchorage independent growth, cell were suspended in 0.4% agarose in complete growth media and plate over 0.8% bottom agar at 10,000 cells per well (H-Ras) or 20,000 cells per well (K-Ras) of a six-well tissue culture dish in triplicate. Cells were fed twice a week over 4 weeks in culture, and colonies were stained using cell staining reagent and protocol from Millipore's Cell Transformation Detection Assay. Images of wells were captured and analyzed by Image J software to count colonies. P-values were determined using a two-tailed Student's T-Test.

Anoikis Assay:

$2 \times 10^5$ cells were plated on either conventional treated 6-well tissue culture plates (TPP, Trasadingen, Switzerland) or on poly-hema coated, non-adherent 6-well tissue culture plates (Sciencell, Carlsbad, Calif.) with 1 µM CellPlayer green fluorescent caspase3 substrate (Essen Bioscience, Ann Arbor, Mich.) and analyzed on an Incucyte FLR live cell imager (Essen Bioscience, Ann Arbor, Mich.) over 44 hours in culture for caspase positive cells.

Telomere Length PCR:

Quantitative PCR analysis of telomere length was carried out as described previously (Cawthon, *Nuc. Acids. Res.* 30(10):e47, 2002). Briefly, quantitative real time PCR was performed using 1 µl of SYBR Green Master Mix (Applied Biosystems) in 25 µl total volume reaction mixture containing water, master mix and primers. Real-time assays were done in triplicate on a BioRad MyIQ™ instrument for real-time PCR detection. Data were collected and analyzed using Stratagene MX3000 software. Standard curves were created for both the single copy reference gene (36B4) and telomere DNA using a range of concentrations of a single patient DNA sample to demonstrate linearity between single copy gene signal and telomere signal. For each patient, single gene and telomere PCR was carried out in triplicate. Telomere to single gene ratio (T/S) was plotted against the age of the patient. Telomere length generally decreases with age. The higher the T/S adjusted for the age related regression, the longer the telomeres.

Results

Efficacy of CLPTM1L shRNAs in Human Cells:

Efficacy of the shRNA constructs described herein when assayed in human cells was determined by evaluating knockdown of total transcript levels using primers with homology to all three human CLPTM1L transcripts (Table 1). Efficacy in mouse cells was evaluated using primers specific to the single known mouse transcript. For select constructs, knockdown of levels of the full-length 538 amino acid human protein and the 539 amino acid mouse protein (Ensembl transcript ID: ENST00000320895 for human and ENSMUST00000022102 for mouse) was also measured as detectable on Western blots. Constructs 168, 252m and 351m are homologous to human CLPTM1L transcripts encoding the full-length 538 amino acid polypeptide and the 502 amino acid polypeptide. These constructs did not, however, have homology to the human transcript encoding the 369 amino acid polypeptide and, in theory, should not target this smallest transcript for degradation. All other constructs were designed to have homology to all three transcript variants. It is theoretically possible to design constructs that would target only the full length transcript or the largest two transcripts, but any construct targeting a smaller transcript would also have homology and therefore theoretically also target the larger transcripts described herein.

High Expression of CLPTM1L in Tumor Adjacent Normal Lung Tissue Correlates with Disease Associated Genotype:

With the knowledge that CLPTM1L is commonly overexpressed in lung adenocarcinoma (James et al., *PLoS One* 7:e36116, 2012), and that genetic polymorphisms within CLPTM1L are associated with risk of developing lung cancer (Chen et al., *Genet Mol Res.* 11:370-8, 2012; Pande et al., *Carcinogenesis* 32:1493-9, 2011; McKay et al., *Nat Genet.* 40:1404-6, 2008; Landi et al., *Am. J. Human Genetics* 85:679-91, 2009), we investigated whether expression in tumor adjacent normal lung tissue correlated with the disease associated polymorphisms within the gene. In 30 lung adenocarcinoma patients, expression of CLPTM1L was an average of 2.8 fold greater in tumor tissue than in matched normal lung tissue (p<0.002) (FIG. 1A). Of these patients, 19 (63%) overexpressed CLPTM1L in lung adenocarcinoma tissue compared to adjacent normal lung tissue by 1.5 fold or greater, with a range of 1.5 to 8.7 fold. To investigate whether lung cancer risk SNPs at the 5p15.33 locus are associated with basal expression of CLPTM1L in normal lung tissues, we genotyped the rs31489 variant and evaluated accumulation of CLPTM1L transcript in tumor adjacent normal lung tissues of 32 adenocarcinoma patients. This variant is one of the most significant risk variants in multiples studies (Pande et al., supra; Liu et al., *Cancer Epidemiol. Biomarkers Prev.* 19:517-24, 2012), and is in LD with rs402710 and rs401681 lung cancer variants. High expression of CLPTM1L in tumor adjacent normal tissues of 32 lung adenocarcinoma patients correlated with the risk genotype at rs31489 (C) (p=0.0002) (FIG. 1B).

Figure 9:
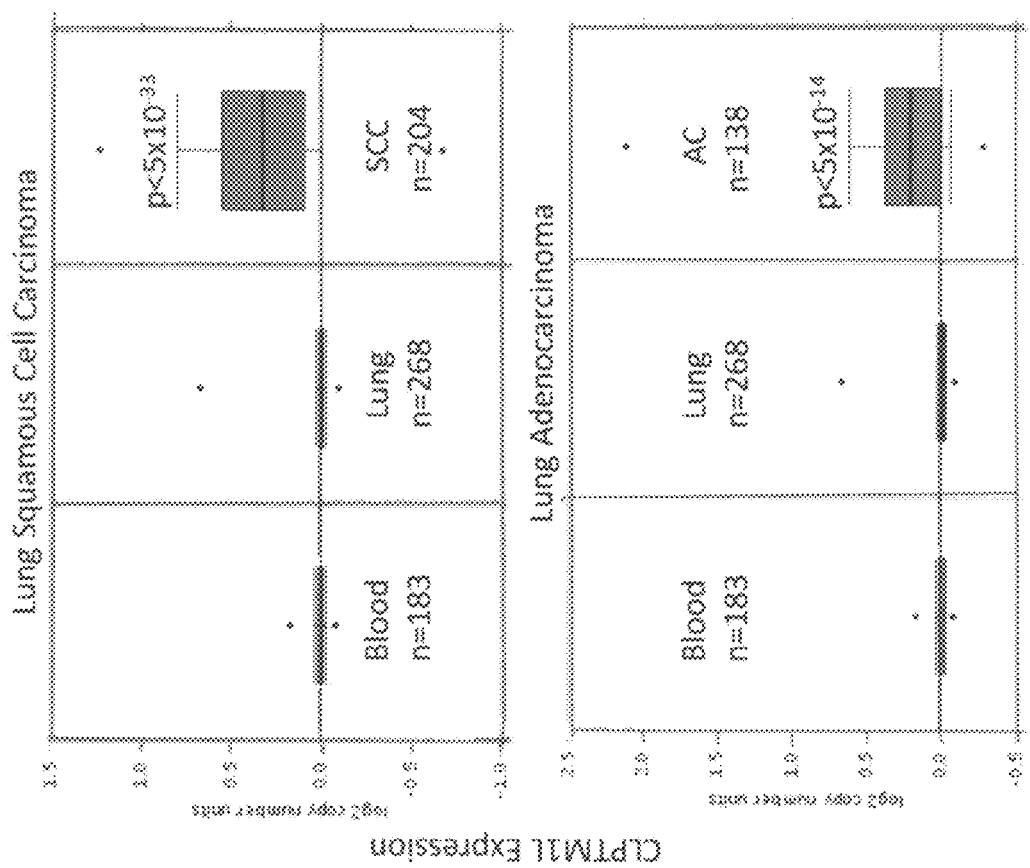
FIG. 9 presents a graph demonstrating relative CLPTM1L expression data from publicly available TCGA sources. The cancer microarray database and integrated data-mining platform Oncomine™ (Compendia Bioscience, Ann Arbor, Mich.) was used for data analysis and visualization.
Figure 10:
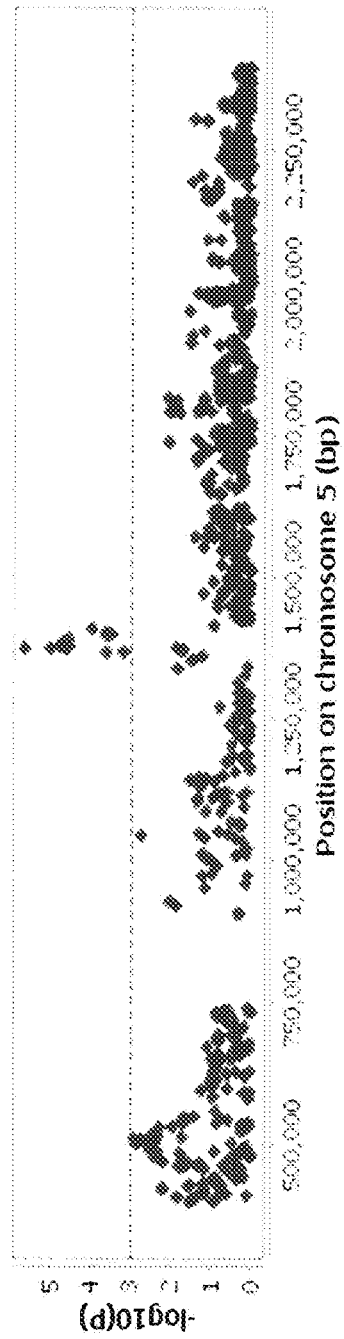
FIG. 10 presents expression quantitative trait loci (eQTL) for CLPTM1L in adipose tissue collected from 856 healthy female twins of the MuTHER resource (available at muther.ac.uk on the World Wide Web). (A) Plot of significance of CLPTM1L associated variants. (B) Table of significant variants, with variants in the most significant 5p lung cancer LD block highlighted. Data analysis was performed using the Genevar database, available at sanger.ac.uk/resources/software/genevar on the World Wide Web.
Figure 11:
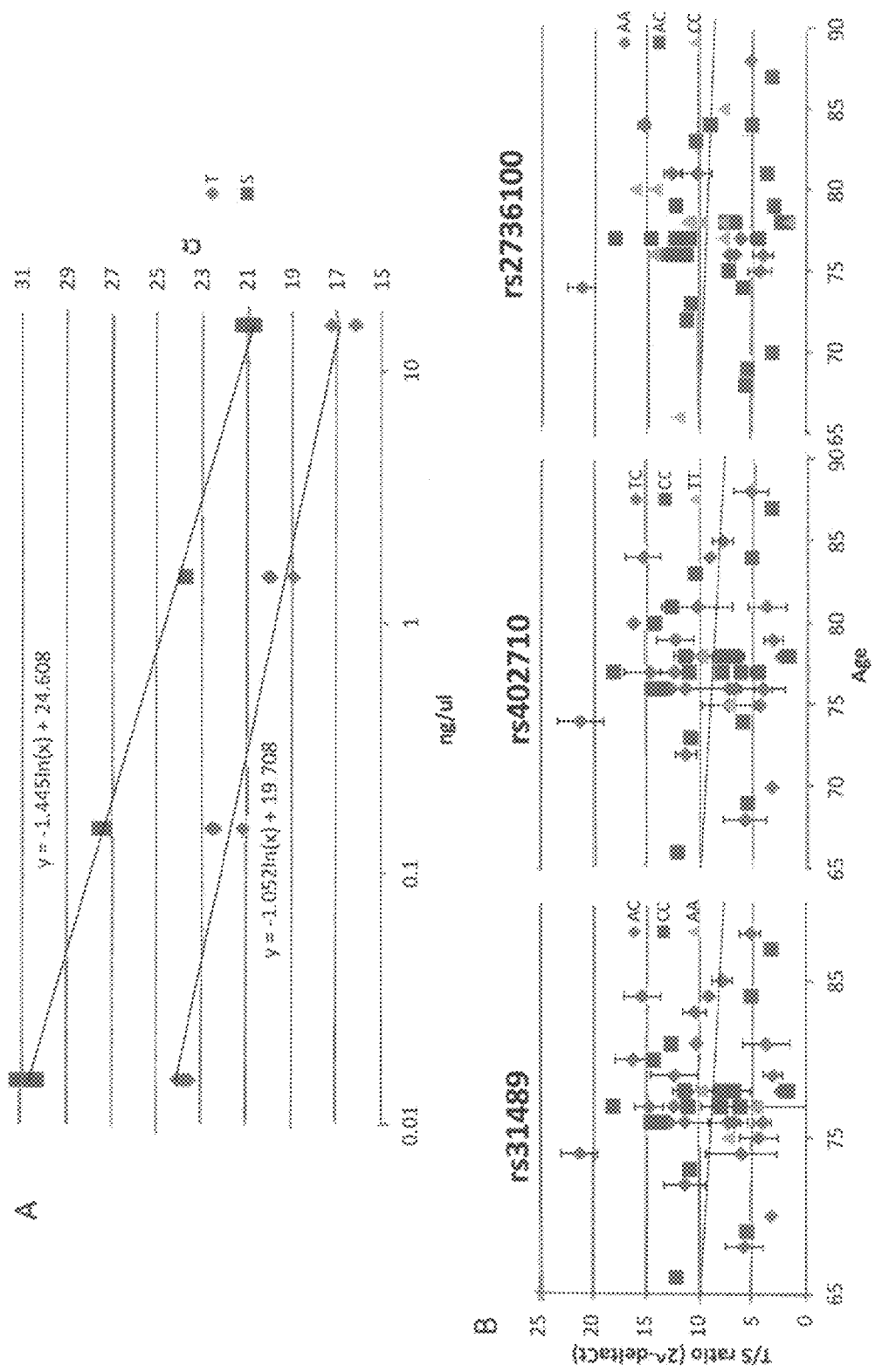
FIG. 11 presents telomere signals and single copy gene signals. (A) Standard curves of 36B4 single copy gene signal (S) to telomere signal (T) to verify that telomere signal can be normalized to 36B4 signal. (B) Telomere length as measured by telomere signal to single gene signal (T/S) plotted against age of the patient. Data was categorized based on the genotype of the indicated lung cancer associated SNP to show any relationship of genotype to telomere length.

These results are in agreement with a 2012 study by Grundberg et al. (*Nat Genet.* 44:1084-1089, 2012) showing cis-regulation of CLPTM1L in adipose tissue of 856 healthy female twins, with disease SNPs correlating exactly with CLPTM1L-regulating SNPs (FIG. 9). Publicly available data analyzed and visualized using Oncomine™ (Compendia Bioscience in Ann Arbor, Mich.) similarly shows highly significant up-regulation of expression of CLPMT1L in lung squamous cell carcinoma ($p<5 \times 10^{-33}$) and lung adenocarcinoma ($p<5 \times 10^{-14}$) compared to normal lung tissue (FIG. 9), as well as in many other cancer types (data not shown).

Figure 2:
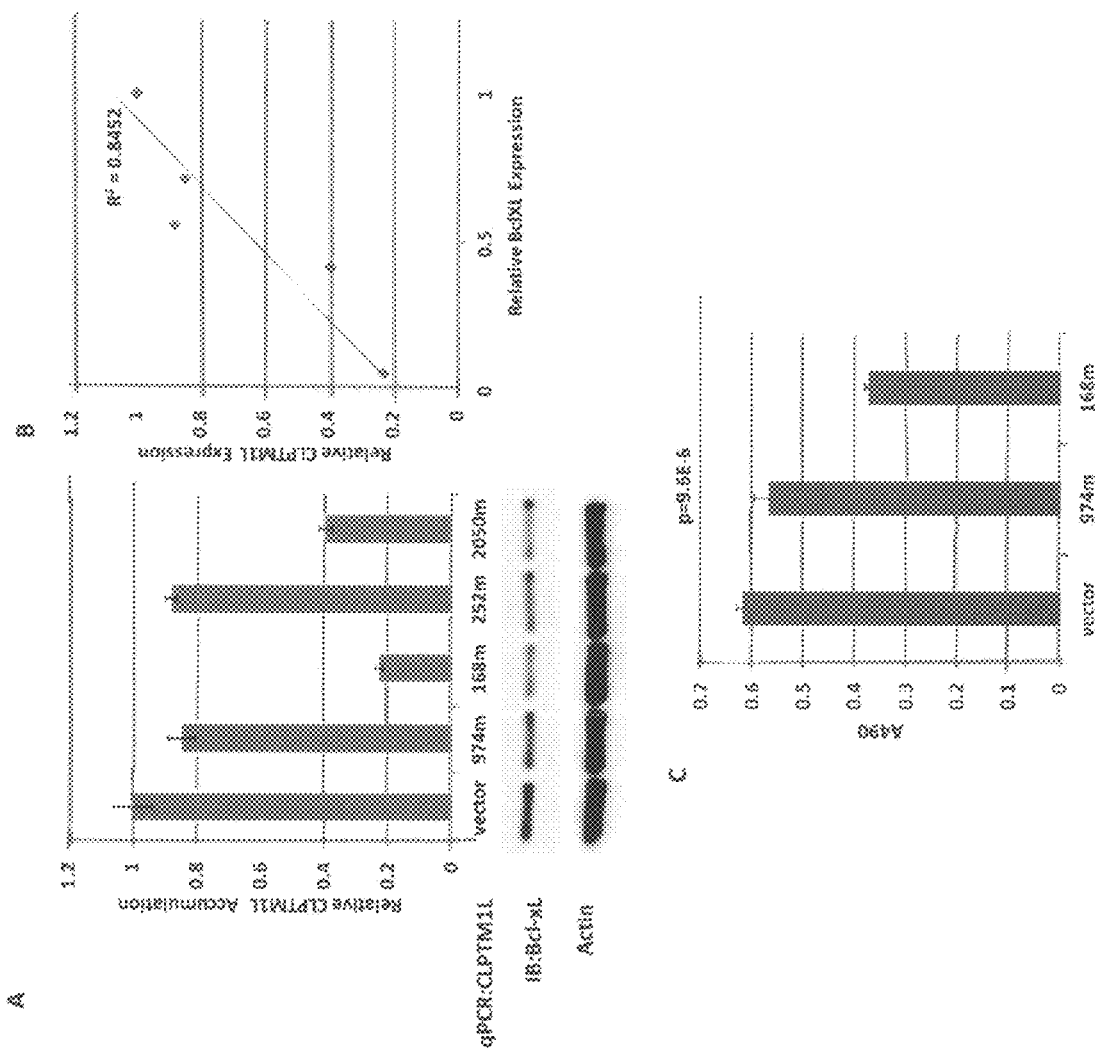
FIG. 2 presents graphs and an image demonstrating that CLPTM1L regulates Bcl-xL accumulation and protects mouse lung tumor cells from genotoxic apoptosis. (A) Relative accumulation of CLPTM1L transcript in Spon8 cells with shRNA vectors targeting CLPTM1L as measured by quantitative real-time PCR normalized to beta-Actin, Bcl-xL protein accumulation as measured by western blot. (B) Scatter plot of CLPTM1L accumulation versus Bcl-xL accumulation demonstrating the correlation between CLPTM1L and Bcl-xL accumulation. Bcl-xL accumulation was normalized to Actin and quantified using Image J software. (C) Cell viability as measured by MTS assay after 48 hours of treatment with 20 µM cisplatin.

Depletion of CLPMT1L Results in Loss of Bcl-xL and Increased Cisplatin Sensitivity in Mouse Lung Tumor Cells:

We previously demonstrated that CLPTM1L expression confers resistance to apoptosis induced by genotoxic agents through regulation of Bcl-xL in human lung tumor cell lines (James et al., supra). This previous work demonstrated that the apoptotic regulators Bcl-2 and Bax are unaffected by CLPTM1L depletion in human lung tumor cells and that Bcl-xL regulation is required for modulation of cisplatin sensitivity (James et al., supra). In the current study, we sought to confirm this in mouse lung tumor cell lines with the intention of conducting transformation assays with mouse fibroblasts and tumorigenesis assays in a murine model. We utilized four retroviral shRNA constructs (see Table 2) in Spon8 mouse lung tumor cells. Spon8 cells are derived from spontaneous metastatic lung tumors from A/J mice. The sh2 construct demonstrated 80% knockdown of CLPTM1L (FIG. 2A). Bcl-xL expression was concurrently reduced upon CLPMT1L depletion. Expression of Bcl-xL correlated strongly with CLPTM1L accumulation ($r^2=0.85$) (FIG. 2B). Quantitative PCR analysis of transcript levels was used for these experiments because protein was undetectable by immunoblot in Spon8 lysates. We further tested whether cisplatin-induced killing of Spon8 cells was dependent on CLPTM1L. Spon8 cells with vector alone, sh1 or sh2 were treated with 20 µM cisplatin for 48 hours. Killing was measured using an MTS assay to measure viability 48 hours post treatment. Spon8 cells with CLPTM1L knockdown mediated by sh2 displayed increased sensitivity to cisplatin compared to vector and sh1, $p=9.6E^{-6}$ (FIG. 2C).

TABLE 2

Retroviral shRNAs for CLPTM1L depletion in
Spon8 mouse lung tumor cells

| shRNA | Construct name | Target sequence (5'-3') |
|---|---|---|
| sh1 | 974m | CAGTTTCTGGAAGAAAAAGAA (SEQ ID NO: 32) |
| sh2 | 168m | AACTGCATCCAGCCCTATCTG (SEQ ID NO: 33) |
| sh3 | 252m | AACAATGTGGACCTGATCTTG (SEQ ID NO: 34) |
| sh4 | 2050m | AAGTCGTTCTGTACGGACTCT (SEQ ID NO: 35) |

Figure 3:
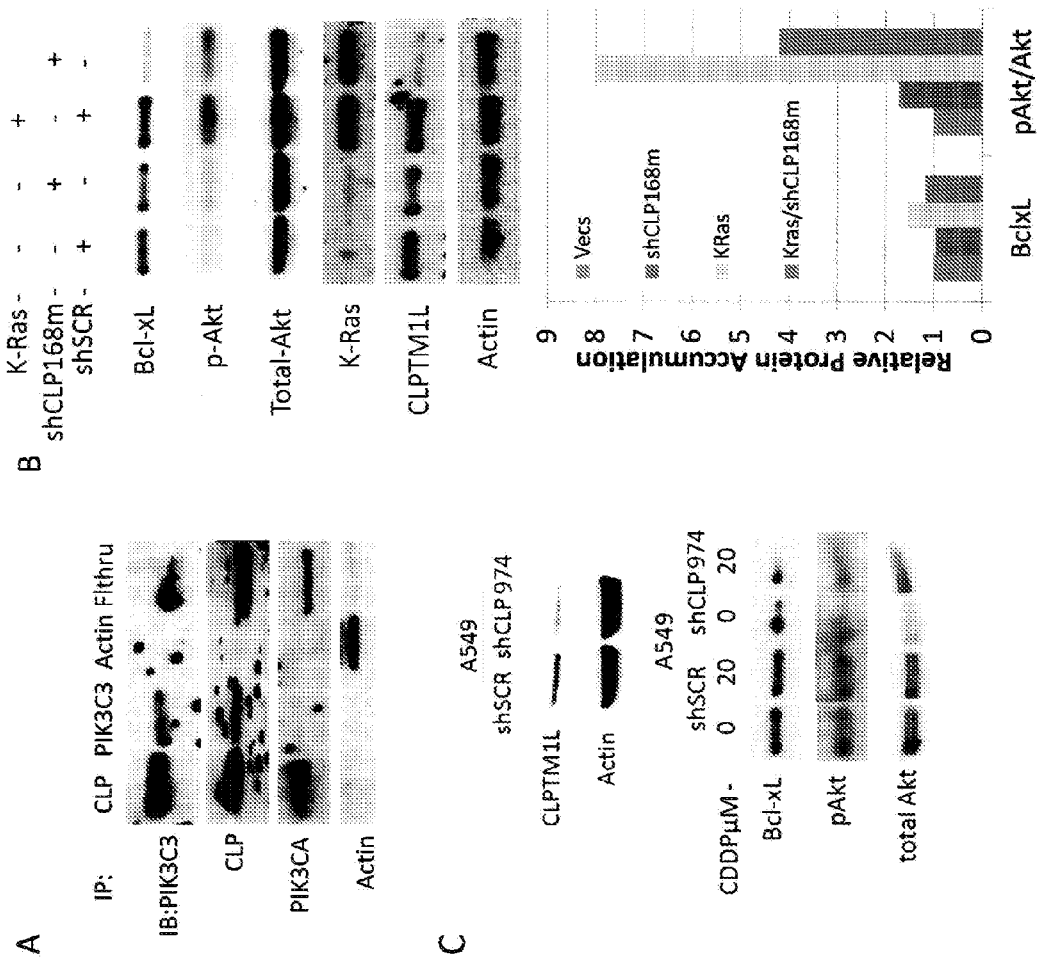
FIG. 3 is series of images and a bar graph illustrating regulation of the Akt pathway and Bcl-xL accumulation by CLPTM1L. (A) Co-Immunoprecipitation of PIK3C3 with CLPMT1L using each as bait or prey. Actin represents a non-specific control IP antibody. "No IP" column represents input. (B) Representative western blot for Akt pathway regulators of apoptosis, Bcl-xL, and CLPTM1L in NIH3T3 cells with K-Ras$^{V12}$ expression and/or shRNA CLPTM1L depletion. Graphic representation of relative protein levels normalized to actin (bottom panel). (C) Representative western blots for CLPTM1L depletion and for Akt pathway regulators of apoptosis/Bcl-xL in A549 human lung tumor cells with and without cisplatin treatment.

CLPTM1L Interacts with PI3K and is Required for Ras Induced Akt Activation and Bcl-xL Accumulation:

Given evidence that CLPTM1L may interact with catalytic subunits of PI3K (PIK3C3) (Behrends et al., Nature 466:68-76, 2010) and regulates survival of tumor cells (James et al., supra), we investigated the effect of CLPTM1L on Akt phosphorylation and its interaction with PI3K. Co-immunoprecipitation was performed on A549 human lung tumor cell lysates using PI3K, CLPTM1L, or Actin irrelevant control antibody immobilized covalently on a resin column. Immunoprecipitates and flow-through lysate from a column without antibody were immunoblotted for PI3K or CLPTM1L. CLPTM1L co-precipitated with PI3K but not with Actin control antibody, both when used as bait and prey, indicating an interaction between the two proteins (FIG. 3A). Survival signaling by PI3K in tumor cells is mediated by phosphorylation of Akt, reviewed in (Carnero et al., Curr. Pharm. Des. 16:34-44, 2010). To investigate the effect of CLPTM1L on Akt signaling, and with the goal of performing transformation and anchorage independence assays (discussed below), oncogenic K-Ras$^{V12}$ was co-expressed in NIH3T3 mouse fibroblasts along with shRNA targeting CLPTM1L. The sh2 construct presented in Table 1 was used and will hereafter be referred to as shCLP168m. Western blotting in these cells demonstrates a decrease in Bcl-xL expression with loss of CLPTM1L, as we previously demonstrated in mouse and human lung tumor cells (see FIG. 2; see also James et al., supra.) Expression of K-Ras$^{V12}$ increased levels of both Bcl-xL and phosphorylated (T308) Akt (FIG. 3B). However, when CLPTM1L was stably depleted with shRNA in K-Ras$^{V12}$ expressing cells, this elevation of both Bcl-xL and phospho-Akt was ablated. Likewise, in A549 lung tumor cells, depletion of CLPTM1L results in decreased Bcl-xL expression and pAkt levels (FIG. 3C). Interestingly, total Akt levels are also decreased in CLPTM1L depleted lung tumor cells. Cisplatin treatment does up-regulate Akt and pAkt. However, this elevation is not to the levels present in tumor cells with endogenous levels of CLPTM1L.

Figure 4:
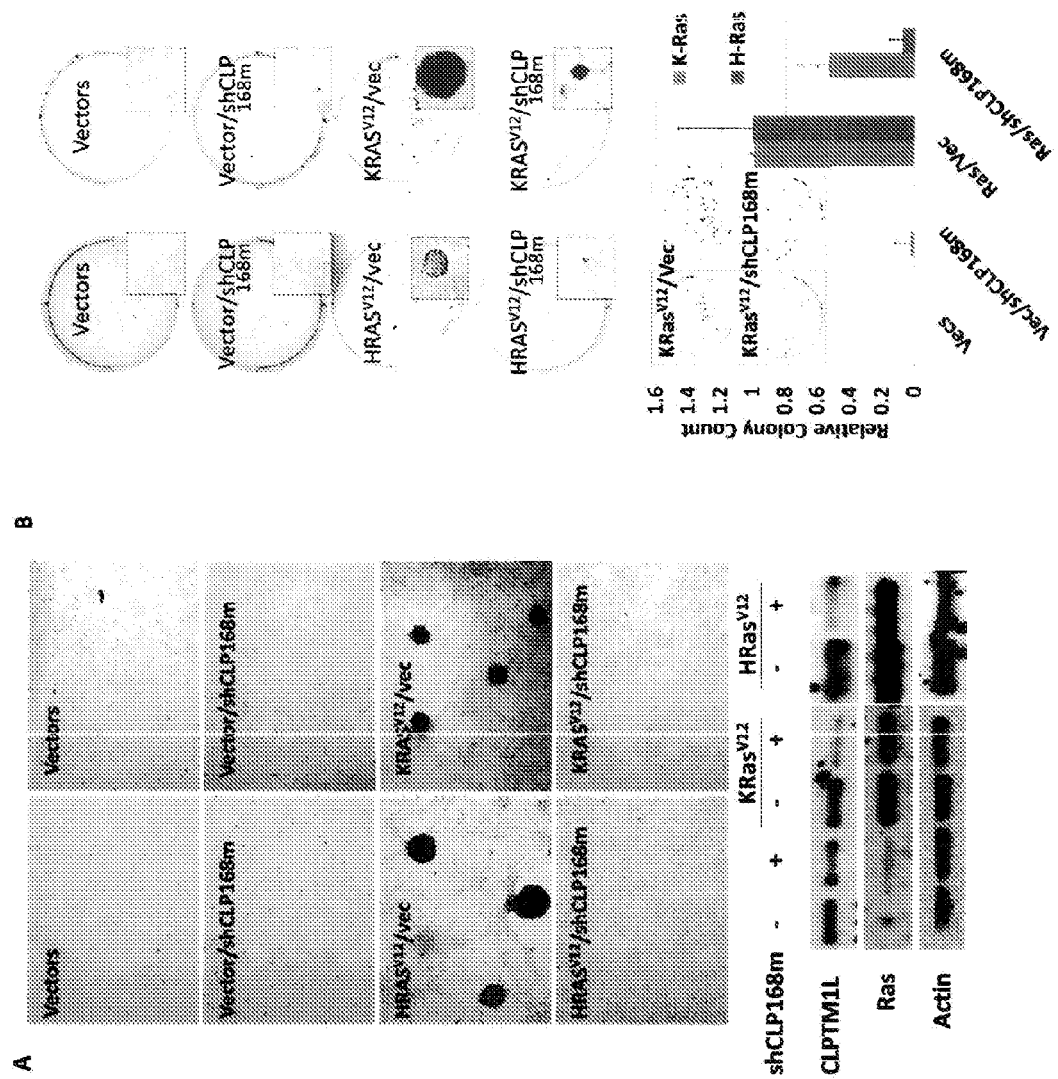
FIG. 4 presents images and a graph demonstrating that depletion of CLPTM1L by shRNA (shCLP168m) ablates Ras oncogenic transformation of mouse fibroblasts. (A) Micrographs of NIH3T3 cells stably transfected with oncogenic Ras isoforms or vector controls as well as shRNA CLPTM1L depletion or vector control. (B) Representative wells of soft agar anchorage independent growth assays in of NIH3T3 cells stably transfected with oncogenic Ras isoforms or vector controls as well as shRNA CLPTM1L depletion or vector control. Bottom panel: graphic representation of relative anchorage independent colony numbers as counted using Image J software. P-values obtained by two tailed Student's T-Test. (C) Anoikis assay on A549 human lung tumor cells with shRNA CLPTM1L depletion or vector control grown on either a conventional or non-adherent surface. P-value obtained by two tailed Student's T-Test. (D) Western blotting for CLPTM1L depletion and Ras expression.

CLPTM1L Dependent Akt Activity is Required for Ras Oncogenic Transformation:

To determine if CLPTM1L is required for oncogenic transformation by Ras, we co-transfected 3T3 mouse fibroblasts with a combination of vector controls, H-Ras$^{V12}$, or K-Ras$^{V12}$ and shRNA targeting CLPTM1L (shCLP168m) or both activated Ras and shCLP168m (as described above). Stable transfection of either H-Ras$^{V12}$ or K-Ras$^{V12}$ induced a transformed morphology microscopically (FIG. 4A). The transformed cells grew in crossing spindle patterns with foci growing into dense spheres of cells that sometimes detached and became free-floating. However, upon stable co-transfection of either H-Ras$^{V12}$ or K-Ras$^{V12}$ with shCLP168m, a nearly complete reversion of the phenotype occurred, as no transformed foci were observed. Cells with Ras$^{V12}$/shCLP displayed altered morphology compared to vector controls, but they did not form dense foci or grow in an anchorage independent manner. Cells with shCLP168m alone did not demonstrate morphological changes compared to vector controls. Exogenous overexpression of Ras$^{V12}$ and knockdown of CLPTM1L was confirmed by western blotting. To further determine the effect of CLPTM1L depletion on the ability of Ras transformed 3T3 cells to grow in an anchorage independent manner, soft agar tissue culture was employed. H-Ras$^{V12}$ transformed cells to anchorage independence, forming an average of 18 colonies per well in soft agar (FIG. 4B), whereas H-Ras$^{V12}$ expressing cells with CLPTM1L depletion formed an average of only one colony per well in soft agar (p<0.03). Similarly, K-Ras$^{V12}$ transfection transformed 3T3 cells. With twice as many cells plated as were plated for H-Ras$^{V12}$ soft agar assays, K-Ras$^{V12}$ transformed 3T3 cells formed 56 colonies per well, which was inhibited by 47% upon CLPMT1L depletion (p<0.02), demonstrating a requirement for CLPTM1L for oncogenic Ras induced anchorage independent growth. H-Ras$^{V12}$ transformed cells to anchorage independence, forming an average of 18 colonies per well in soft agar (FIG. 4B), whereas H-Ras$^{V12}$ expressing cells with CLPTM1L depletion formed an average of only one colony per well in soft agar (p<0.03). Similarly, K-Ras$^{V12}$ transfection transformed 3T3 cells. With twice as many cells plated as were plated for H-Ras$^{V12}$ soft agar assays, K-Ras$^{V12}$ transformed 3T3 cells formed 56 colonies per well, which was inhibited by 47% upon CLPMT1L depletion (p<0.02), demonstrating a requirement for CLPTM1L for oncogenic Ras induced anchorage independent growth. Expression of constitutively active myristoylated Akt rescued the transformed phenotype in 3T3 cells with K-Ras$^{V12}$ expression and CLPTM1L depletion, indicating that maintenance of Akt expression by CLPTM1L is necessary to maintain oncogenic K-Ras transformation (FIG. 4C). Expression of myrAkt did not alter Bcl-xL expression or its regulation by CLPTM1L, indicating that Bcl-xL is regulated by a separate mechanism and its regulation by CLPTM1L is not sufficient for the effect on oncogenic transformation (FIG. 4D), although it may still be required.

Figure 5:
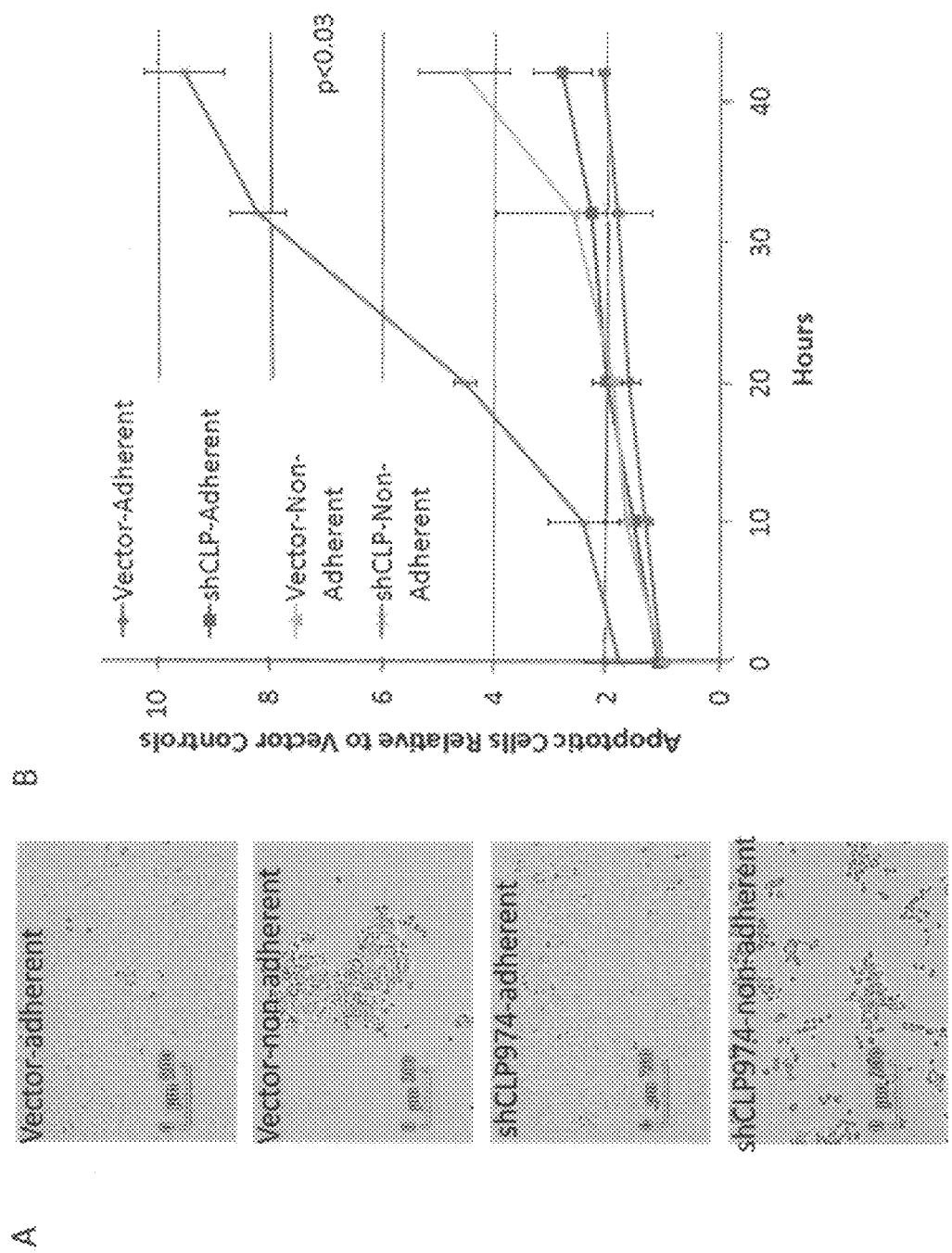
FIG. 5 presents a series of images and a line graph demonstrating that CLPTM1L regulates Akt signaling/Bcl-xL expression and is required for protection from anoikis in human lung tumor cells. (A) Representative micrographs of A549 cells cultured on poly-HEMA coated non-adherent plates or conventional treated plates. (B) Anoikis assay (real-time quantification of caspase3 positivity in live cells) on A549 cells with short-hairpin RNA (shRNA) depletion of CLPTM1L (shCLP974) or vector control; grown on either a conventional or non-adherent surface. P-value obtained by two tailed Student's T-Test.
Figure 7:
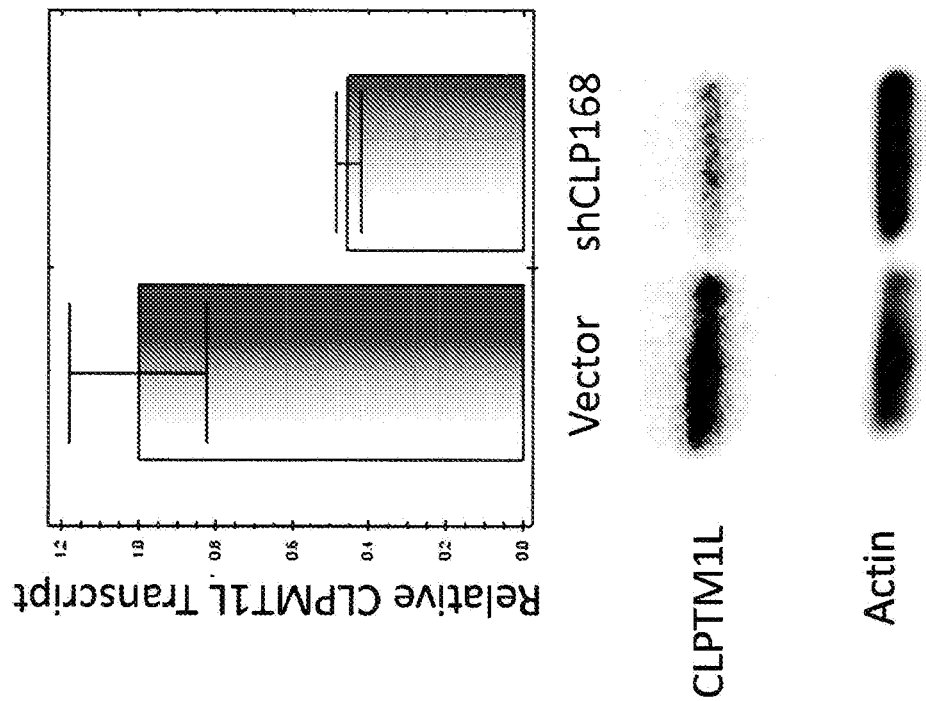
FIG. 7 presents a graph and an image to demonstrate CLPTM1L transcript levels in A549 human lung tumor cells with and without a short hairpin RNA construct (shCLP168m) to suppress CLPTM1L expression.

CLPTM1L Protects Human Lung Tumor Cells from Anoikis:

To determine if CLPTM1L was similarly necessary in lung tumor cells for survival of anchorage detachment, assays for anoikis were employed. A549 cells with CLPMT1L depletion (using short hairpin construct: shCLP974) or shRNA control vector were plated in triplicate on poly-HEMA coated plates to prevent attachment, as well as conventional coated tissue culture plates. Non-adherent cells with control vector grew in clusters of refractile cells (FIG. 5A). Non-adherent cells with CLPTM1L depletion (shCLP974) grew in clusters that generally appeared flat and dull. Apoptotic cell numbers were monitored in real time using a fluorescent caspase3 substrate and live cell imaging system over 44 hours in culture. Apoptosis was induced to a significant degree on a non-adherent surface only when CLPMT1L was depleted, demonstrating that CLPTM1L can protect lung tumor cells from anoikis (p<0.03) (FIG. 5B).

CLPTM1L is Required for Lung Tumorigenesis in a shRNA/K-Ras$^{LSL-G12D/+}$ Mouse Model:

A recently developed model of lung cancer in K-Ras$^{LSL-G12D/+}$ transgenic mice utilizes intratracheal delivery of lentivirus expressing CRE recombinase to activate oncogenic K-Ras expression. This model also permits simultaneous expression of short hairpin RNAs targeting a gene of interest, via the same viral vector (DuPage et al., *Nat Protoc.* 4:1064-72, 2009) and is thus particularly well suited to the investigation of potential modifiers of lung tumorigenesis. We utilized this model to induce oncogenic K-Ras driven lung tumors in a cellular environment that is depleted of CLPMT1L (FIG. 6A). We also evaluated depletion of TERT in this model to agnostically approach 5p susceptibility candidates and to serve as an additional control. Several lentiviral shRNA vectors targeting TERT or CLPTM1L were designed and evaluated for knockdown of their target transcripts in the Spon8 mouse lung tumor cell cells. Vectors shTERT1 and shCLP168m accomplished knockdown at the transcript level of 50% and 80% for TERT and CLPTM1L, respectively (FIG. 2A; see also FIG. 8), and were subsequently used in the mouse model studies. Virus particles were packaged, and titered by infection of 3TZ cells and quantification of the number of CRE dependent LacZ-inducing particles per milliliter. Mice were subsequently infected with $10^4$ functional particles (high dose group) or $10^3$ particles (low dose group) by intratracheal intubation. After 24 weeks, lungs were harvested and lung tumors were counted and sized for the high dose group. Most tumors were ≤1 mm in diameter with a few larger tumors. Mice in the high dose group with a nonspecific scrambled shRNA had an average of 115 tumors per mouse with an average tumor load of 13.2 $mm^3$ (FIGS. 6B and 6D), while mice with CLPTM1L depletion had an average of 46 tumors per mouse with an average tumor load of 3.4 $mm^3$. This equates to a 60% inhibition of tumor number (p=0.02) and a 74% inhibition of tumor load (p=0.03) in mice with CLPTM1L depletion. Mice with TERT depletion had an average of 122 tumors per mouse with an average tumor load of 10.2 $mm^3$ and were statistically similar to the control group (p=0.58). The low dose group was counted at 28 weeks post-infection. Scrambled control and shTERT mice had an average of 6 and 5 tumors, with average tumor loads of 0.50 and 0.41 $mm^3$ respectively (FIGS. 6C and 6D). Only one mouse with CLPTM1L depletion (n=7) had a single tumor for an average tumor number of 0.14 and load of 0.01 $mm^3$. This represents 98% inhibition of both tumor number and load (p<0.004 and p<0.002 respectively). There was no significant difference or trend in tumor number or load between scrambled shRNA mice and mice with TERT depletion.

Figure 14:
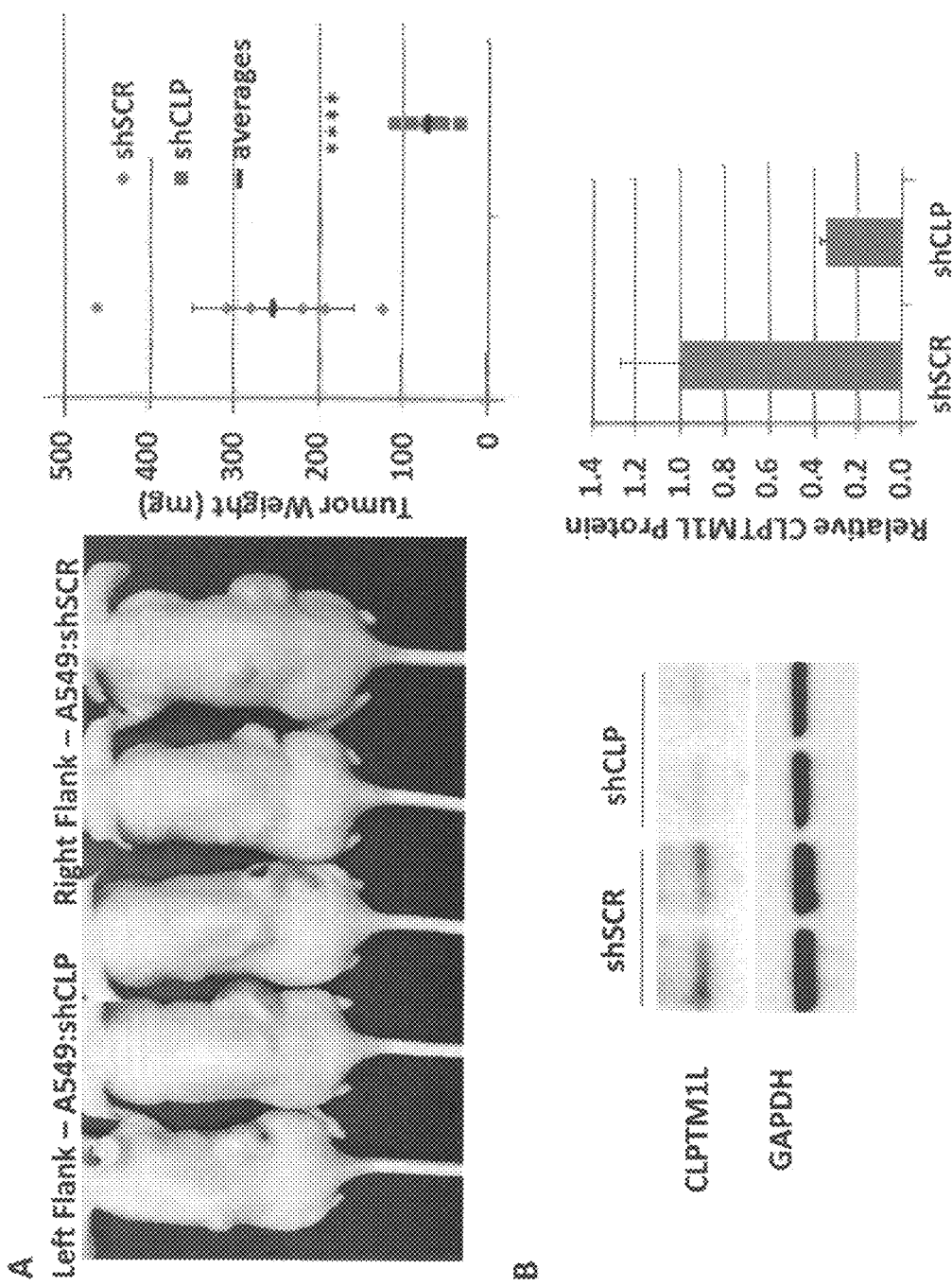
FIG. 14 presents data demonstrating that CLPTM1L is required for tumorigenesis in a human lung tumor xenograft model. (A) The image shows athymic nude mouse xenograft tumorigenesis assays in which the left flank was 5×10$^5$ A549 stably transduced with a short hairpin RNA construct (shCLP1850) (SEQ ID NO:14), and the right flank was 5×10$^5$ A549 stably transduced with scrambled shRNA control (shSCR) four weeks after implantation of tumor cells. The graph presents tumor weights four weeks after implantation of tumor cells. ****-p<0.00005. (B) Images of Western blotting results show CLPTM1L protein accumulation in tumor tissue stably transduced with shCLP1850 or scrambled shRNA control; GAPDH normalized relative CLPTM1L accumulation was quantified using Image J software and presented in graphical form.

FIG. 14 presents the results of additional in vivo assays in a mouse xenograft model of tumorigenesis using stable lung tumor cell lines of human origin having CLPTM1L depletion by shRNA (SEQ ID NO:14) or having control shRNA. For these assays, CLPTM1L depletion was established in cells of the stable lung tumor lines before implantation into the mice. A robust effect on the ability of these cells to form tumors in mice was observed. These data and those of FIGS. 3-6 and 9-11 are presented in James et al., *Cancer Res.* (2013) (Epub ahead of print; doi:10.1158/0008-5472.CAN-13-1617).

Discussion

The association of high CLPTM1L expression with disease SNPs at the 5p locus is highly suggestive that cis-regulation of CLPTM1L contributes to lung cancer risk. Our results agree with the study by Grundberg et al., supra, which showed cis-regulation of CLPTM1L in adipose tissue of 856 healthy female twins (FIG. 9). This study was able to separate heritable expression differences from those influenced by environment by using twins. By regulatory trait concordance (RTC) methodology, the authors showed perfect concordance of CLPTM1L regulatory SNPs with lung cancer risk SNPs suggesting that cis-regulation of this gene is likely involved in heritable risk. Results from the in vivo tumorigenesis experiments establish a tumorigenic role for CLPTM1L in lung cancer and provides further evidence that this gene contributes to the 5p association with susceptibility to lung cancer. This recently developed approach to the study of modifiers of tumorigenesis allows for the manipulation of expression of a gene of interest with shRNA concurrently and exclusively in cells that are K-Ras$^{G12D}$ induced (DuPage et al., supra). This study successfully demonstrates the use of this model to identify a modifier of lung tumorigenesis, which validates its utility in the investigation of other GWAS identified candidate genes. Tumors arising from this model are mostly small adenomas (≤1 mm) (DuPage et al., supra). The limited tumor progression in this model allows for the evaluation of modifiers of tumor initiation and tumor growth. Models involving rapid tumor growth and progression may not be as suitable for testing such modifiers due to strongly driven tumors that are impervious to less robust modifiers of growth. Being multifocal, this model is expected to have some heterogeneity due to cellular and microenvironmental differences. Thorough evaluation of CLPTM1L depletion in vivo and in vitro will include evaluation of RNAi-inducing construct efficacy and downstream effects, and histological characterization of any tumors, cancerous and pre-cancerous lesions, and cells suspected of or at risk of becoming neoplastic.

We did not see an effect on tumorigenesis with knockdown of TERT expression. This may indicate one or a combination of the following; (1) TERT expression does not immediately and directly affect lung tumorigenesis, (2) this model may miss indirect, long-term or trans-generational affects, potentially related to maintenance of telomere length, (3) longer telomere length in the mouse may mask the effect of TERT knockdown, and (4) inefficient knockdown of TERT in vivo. Mice with shTERT also served as an additional non-specific control for CLPTM1L knockdown mice. TERT is well studied for its role in telomere maintenance, bypass of replicative senescence and cellular immortalization. It is commonly overexpressed in tumor tissue. For review, see Chen et al., *J. Formos Med. Assoc.* 110:275-89 (2011). Overexpression of TERT allows cellular immortalization through telomere maintenance, which is the most likely mechanism by which TERT may contribute to the 5p association with cancer risk. A recent study suggests that 5p risk variants may be associated with hypermethylation in the TERT promoter (Scherf et al., *Oncogene* (2012) (published online ahead of print; doi: 10.1038/onc.2012.344), however existing data regarding association of 5p variants with TERT expression and telomere maintenance is conflicting at best (Mirabello et al., *Hum. Mutat.*, 2010; Pooley et al., *Cancer Epidemiol. Biomarkers Prev.*, 2010; Fehringer et al., *Cancer Epidemiol. Biomarkers Prev.*, 2012). In an analysis of SNPs in the 5p region, we have found that lung cancer associated SNPs are not associated with telomere length (FIG. 11), which is in agreement with two other studies (Mirabello et al., *Hum Mutat.*, 2010; Pooley et al., *Cancer Epidemiol Biomarkers Prev.*, 2010). In contrast, a study by Rafnar et al. showed an association (p=0.017 and 0.027, respectively) between 5p variants (rs401681 and rs2736098) and telomere length, although this effect was only seen in women older than 75 years with homozygous genotypes (Rafnar et al., *Nat Genet.* 41:221-7 (2009)). Indeed, an association of a particular genetic region with cancer may suggest that a gene within that region can be used as a biomarker of a cancer or risk of developing a cancer, but the association alone cannot identify any gene within the genetic locus as a specific target for cancer prevention or therapy. Regardless of the suggestion of association with cancer susceptibility of a gene, the utility of targeting a gene within the genetic locus by any mechanism to treat or prevent a cancer would not be obvious to a scientist having ordinary skill in the art.

Data demonstrating that stable depletion of CLPTM1L ablates morphologic transformation and anchorage independent growth of 3T3 cells by oncogenic H-Ras or K-Ras establish CLPTM1L as possessing an important pro-tumorigenic function relevant to not only cancer of the lung, but other cancers as well. It is known that H-Ras and K-Ras can prevent down-regulation of Bcl-xL upon detachment from the extracellular matrix, thereby avoiding anoikis, or apoptosis due to detachment (Rosen et al., *J. Cell Biol.* 149:447-56, 2000). Here we present evidence that CLPTM1L is necessary for the sustained Ras induced accumulation of Bcl-xL. Depletion of CLPTM1L and the resultant depletion survival signals are associated with a nearly complete reversion of morphological transformation by Ras. Interestingly, depletion of CLPTM1L ablated Ras induced Akt phosphorylation. The addiction of cancers to Ras can be reduced to PI3K/Akt signaling (Lim et al., *Cancer Cell* 8:381-92, 2005). NFκB signaling, which is downstream of Akt, has recently been shown to be required for lung tumorigenesis in a K-Ras driven model very similar to that used in this study (Meylan et al., *Nature* 462:104-7, 2009), although we did not see strong evidence that NF B dependent transcription was significantly affected by CLPTM1L (data not shown). Akt signaling is known to confer resistance to anoikis (Koci et al., *Cytokine* 55:34-9, 2011; Liu et al., *Mol. Cancer Res.* 9:390-402, 2011; Du et al., *Oncogene* 28:3714-22, 2009) and apoptosis induced by TRAIL (Koci et al., supra), etoposide chemotherapy (Mayo et al., *J. Biol. Chem.* 277:5484-9, 2002) and the p53 pathway (Mayo et al., supra; Mayo et al., *Trends Biochem. Sci.* 27:462-7, 2002). Together, these data suggest that the Akt pathway may be an important survival pathway regulated by CLPTM1L. However, Bcl-xL expression, modulation of which is required for the effect of CLPTM1L on genotoxic apoptosis in human lung tumor cells (James et al., supra), was unaffected by constitutively active Akt, suggesting that CLPTM1L may promote survival of tumor cells independently of Akt signaling. The effect of CLPTM1L appears to be upstream of both Akt signaling and Bcl-xL stabilization, both of which may independently play a role in the pro-tumorigenic effect of CLPTM1L. Abrogation of the effect of CLPTM1L depletion on K-Ras transformation by myrAkt mechanistically implicates this pathway in CLPTM1L dependent oncogenic transformation.

Since the effect of CLPTM1L is apparently through regulation of mitochondrial apoptosis, and since the CLPTM1L locus is associated with all lung cancer histologies (Timofeeva et al., *Human Molecular Genetics* 21(22):4980-95 (2012)), we hypothesize that its effect may not be exclusive to Ras mutant driven tumors, but may rather influence any tumors with aberrant growth signaling. In agreement with this premise, a majority of lung tumors we tested over-expressed CLPTM1L compared to adjacent normal tissue, a much higher number than would be expected to harbor K-Ras mutations. DNA was unavailable for mutational analysis in these patients and all available RNA was utilized. In support of this hypothesis, we did not observe higher CLPTM1L expression in lung tumor cell lines harboring oncogenic K-Ras mutations. Further investigation of the effect of CLPTM1L on transformation by mutant forms of EGFR is warranted.

It has been shown that depletion of Bcl-xL with siRNA can sensitize cisplatin resistant human lung adenocarcinoma cells (Lei et al., *Acta Biochim Biophys Sin* (Shanghai) 39:344-50, 2007). Our previous studies have shown that Bcl-xL, but not other apoptotic regulators Bcl-2 and Bax, is regulated by CLPTM1L and that this regulation is required for the effect on cisplatin sensitivity (James et al., supra). Protection from apoptosis upon DNA damage may lead to an accumulation of such damage and subsequent accumulation of mutations leading to cancer. In fact, the lung cancer associated SNP rs402710 within CLPTM1L, has recently been found to be associated with high levels of bulky aromatic and hydrophobic DNA adducts (Zienolddiny et al., *Carcinogenesis* 30:1368-71, 2009).

The in vivo effect of CLPTM1L depletion on lung tumorigenesis was quite striking; significantly inhibiting both tumor incidence and load by up to 98%. Together these results strongly implicate CLPTM1L-dependent protection from apoptosis through regulation of survival signaling as a mechanism necessary for Ras transformation and lung tumorigenesis. The current study demonstrates a clear tumorigenic role for CLPTM1L, which until now has only been functionally related to cisplatin resistance in ovarian tumor cells (Yamamoto et al., *Biochem. Biophys. Res. Commun.* 280:1148-54, 2001). CLPTM1L may represent an important biomarker for chemoresistance and tumor progression, and has high potential as a therapeutic target influencing anoikis, anchorage independent growth, and therefore the ability of tumor cells to progress and metastasize. These findings justify further investigation of the influence of CLPTM1L on cancer risk, its function, and its use as a target for cancer prevention, treatment, and sensitization to genotoxic therapy.

We claim:

1. An RNAi-inducing construct, the construct comprising a double stranded inhibitory ribonucleic acid (RNA) molecule comprising a sense strand and an antisense strand, wherein a nucleotide sequence of the sense strand is selected from the group consisting of SEQ ID NO:4 and SEQ ID NO:5.

2. The RNAi-inducing construct of claim 1, wherein the construct is a short-hairpin RNA (shRNA).

3. The RNAi-inducing construct of claim 2, wherein the shRNA comprises an inverted repeat of the nucleotide sequence and a loop region.

4. The RNAi-inducing construct of claim 3, wherein the loop region comprises between 3 and 24 nucleotides in length.

5. The RNAi-inducing construct of claim 2, wherein the shRNA is in the form of a vector expressed shRNA.

6. The RNAi-inducing construct of claim 5, wherein the vector expressed shRNA comprises an inverted repeat of the nucleotide sequence and a loop region.

7. The RNAi-inducing construct of claim 5, wherein the vector is an adenoviral vector.

8. The RNAi-inducing construct of claim 5, wherein the vector is a retroviral vector.

9. The RNAi-inducing construct of claim 8, wherein the retroviral vector is a lentiviral vector.

10. The RNAi-inducing construct of claim 9, wherein the lentiviral vector is packaged into an infectious particle.

11. A composition comprising the RNAi-inducing construct of claim 1 and a delivery agent.

12. The composition of claim 11, wherein the delivery agent is selected from the group consisting of a liposome, a cationic or non-cationic polymer, a lipid, a peptide molecular transporter, and a surfactant.

13. The composition of claim 11, further comprising a pharmaceutically acceptable diluent, excipient, or carrier.

14. The composition of claim 11, further comprising a plurality of RNAi-inducing constructs whose presence within a cell results in production of a plurality of different siRNAs or shRNAs targeting at least a portion of SEQ ID NO:1.

15. A method of suppressing expression of a nucleic acid sequence encoding CLPTM1L in a subject, the method comprising administering the composition of claim 11 to a subject.

16. The method of claim 15, wherein administering comprises introducing the composition into the subject intranasally, intravenously, or by inhalation.

17. The method of claim 16, wherein the composition is administered as an aerosol.

18. The method of claim 16, wherein introducing the composition into the subject intranasally, intravenously, or by inhalation suppresses expression of a nucleic acid sequence encoding CLPTM1L in cells of the subject's respiratory system.

19. A method of treating a disease or condition associated with over-expression or inappropriate expression of a nucleic acid sequence encoding CLPTM1L, the method comprising administering the composition of claim 11 to a cell, tissue, or organ of a subject diagnosed as having or exhibiting a symptom of the disease or condition, wherein the disease or condition is a cancer or a pre-cancerous lesion.

20. The method of claim 19, wherein the cancer or pre-cancerous lesion exhibits resistance to a chemotherapeutic agent.

21. The method of claim 20, wherein the chemotherapeutic agent is cisplatin.

22. The method of claim 19, wherein the cancer or pre-cancerous lesion is selected from the group consisting of lung cancer, pancreatic cancer, prostate cancer, skin cancer, bladder cancer, kidney cancer, ovarian cancer, colon cancer, colorectal cancer, breast cancer, cervical cancer, brain cancer, esophageal cancer, stomach cancer, lymphoma, chronic leukemia, and acute leukemia.

23. The method of claim 19, wherein the composition is administered as an aerosol.

24. The method of claim 19, wherein administering comprises introducing the composition into the subject by inhalation, by intubation, by intratumoral injection, or intranasally, intravenously, intraocularly, intraperitoneally, topically, orally, rectally, or vaginally.

25. The method of claim 24, wherein introducing the composition into the subject intranasally, intravenously, or by inhalation suppresses expression of a nucleic acid sequence encoding CLPTM1L in a cell or a tissue of the subject's respiratory system, whereby the disease or condition is treated or prevented.

26. An RNAi-inducing construct, the construct comprising a double stranded inhibitory ribonucleic acid (RNA) molecule comprising a sense strand and an antisense strand, wherein a nucleotide sequence of the sense strand is selected from the group consisting of SEQ ID NO:9 and SEQ ID NO:15.

* * * * *

```
SEQUENCE LISTING

<160> NUMBER OF SEQ ID NOS: 35

<210> SEQ ID NO 1
<211> LENGTH: 28557
<212> TYPE: DNA
<213> ORGANISM: Homo sapiens

<400> SEQUENCE: 1
ggctgcccga gggcctccca ctgacctccc ccggccgccc tccgagggc ctctgctgac      60 ctcgccgtgc tgggcacgct cggctttagc gggaagctgg gggtcaggtt caaggctgtg     120
aggagccact tcagcccggg aatctgaatt ttttcttcaa aagcgcctgt ccccacaatg     180
ggtttgtact ggggaaaaaa cccacacacg ggatgaggtg cccggcttct gtgagggttc     240
tgagcacttc gtttttcttc cctttagatt ctgacaactg tggactaaaa gggttgcagg     300
cccagtgccg gaattccagt atcaccttcc accaggctcc tcacacgtcg acatggcccc     360
```

```
cacttggtgg tctggcaggc gtcggcggtt ggggacggcg ccccggggac cccgcggccc    420
tagccttccc cggcgccccg cgaacgccct ccgcggcccc agcagctgag cgcctgggtc    480
cctgagaggc accccaggag ggcggcgcgg gcgggtaacg tcacacacgc gccgcatcct    540
ggatgcgcgt gcgcggcagc ggccgagact ccgtttccca gggagccgcg cggcgcgtcc    600
acttccggca ggcggcgggg cccggaagcg gcgcgcgggg ccggcgaatc ccgcggcgcc    660
aggtgggagc ggggccggag catgcggggc ggccggcggt ctgcggcgcg cggcgcattc    720 gttccccgc ggcggtggcg gtggcgcgcg gcggctctcc agtgagcggc ggagcccgga    780
gcggcgggct gggcgccggg cgggcgggc tcgcggctga gaggcgggcg ggccggggc    840 gccgggcgcg gggccgccat gtggagcggc cgcagctcct tcaccagctt ggtggtgggc    900
gtgttcgtgg tctacgtggt gcacacctgc tgggtcatgt acggcatcgt ctacacccgc    960
ccgtgctccg gcgacgccaa ctgcatccag ccctacctgg cgcggcggcc caagctgcag   1020
gtgagcgtcc gcggggccgg gggccgggcg ggttggggtg ggggcctctc ctccaggccc   1080
cagacgtcgc cttcccgtcc cagttcggag ctgtggccgc gcgagtcgag atggaacctt   1140
tcctggttcc ccagcggcca ggtcttccgc cctccagctg gccgtgggat ttgagtgcgt   1200
cctgccaggg cctggccgag ctgactctcg acgcccccte ctttccagct gagcgtgtac   1260
accacgacga ggtcccacct gggtgctgag aacaacatcg acctggtctt gaatgtggaa   1320
gactttgatg tggagtccaa atttgaaagg tatgggcgta ggacaaaatg ccagtgaaag   1380
ggaaaacatt actcatgttc agattgttta aagttagct ttctgtacat aacatgttta   1440
ttttagagaa ctagtcttac cgaatgtctt gaagtggtag aatatcctaa ctggaggcct   1500
atgcgtggcc tgtaaacatt cagcctggaa ggtgacaggt gatgaatgtc gtttaagaag   1560
tagttctcag cagagtgtga tggcagtggg atgtcctgga cggggaggct ccgaaggagc   1620
aggggccacg cttggtgaac cagtggagag cagacaactc tgcagtttca ctaccgggga   1680
ccaacttgtc ttttcctggt ggaagtagtt cgcttaagtt acttgtgagg gaaaagagat   1740
gaggatagag gaagcaattt tgtagaaaat cataaataag tgacatgtga cgttagaata   1800
gatcaatgtc caaatatgta gagtatctta aaaattacat ctgacatggc ctaatttttt   1860
ttaattgaat aagtatactt ttaaatatga tttgcttctc acaagtcaac catttccctt   1920
cattgcctgg gaggtatctg aggagagaat aatgaaagtt tgagactcat gctggactcc   1980
acgccctcta ggcagccagt ccctggggt agctggaggc gctggcaagc cggtttctgc   2040
ctggcctctt taggcctgtg acctcaagcc agttcctgcc ctctctctgc ctccatgaag   2100
gggaggccag aagtgctggt gaccaagctg cccgctcggt tgtagctgcc cacacctttc   2160
aaaaatgctc aggattcatc tgcactgggt ttaatttccc agacatgaat actgcctctt   2220
ccgtgccggg ccgtgtacca gttaccaagg acagctagtg aggttttcca tttgacctgg   2280
cacagtgtca gcctggagga agtgggggaga atgagcactc ttaacacagc tccgcctcaa   2340
gtgtctccaa gtgcacattc caccagaaat acacagccct gcaccctctg cctgaagaga   2400
gacacttaag atgtcctggt ggagacatac tctttcctgg gtagtgagga gccatagatg   2460
cctttgtgtt tttcattaca actttggccg taagattttt tttttttttt gagatagagt   2520
cttgctctgt tgccaggctg gagtgcagtg gcgtgatctc tgctcactgc aacctccggt   2580
tcccgggttc aagggattct cctgccttag cctccaaagt agctgagact acaggcaccc   2640
gccaccacgc ctggctaatt tttttatttt tagtagagac agggtttcac catgttggct   2700
```

```
gggctggtct gaaactcctg acctcgtgat ctgcccggct cggcctccca aggtgctggg    2760
attacaggcg tgagccgccg cacccggcca accgtaagat ttttaaggag aggccgggca    2820
cagtgactca tgcctataat cccagcagtt tgggaggcca aggcgggagg atcacttgag    2880
cccagcagtt caagaccagc ctaggcaatg tgacaaaacc ccatctctac aacagttttc    2940
aaagttagcc aggcatggtg gcacgcccac ctgtagtccc agctactcgg gagactgagg    3000
cgggaggtca cttgagctca ggaggttgag gatgcagtga gctgtgattg cacccctaca    3060 cttttcagcct ggtgacagcg agaccttgtc tcaaaaaaga acttttaaa gaggaagaag    3120 aactcatgta accgtaaaca ggtggaatgc gaggttttc catggggctg tagtatggac    3180
gtcgggccct ggtgtgcggg tgaagagcca ggcacctggt ccgaggccta cagttgtagc    3240
agctcgccgg gccttttcctc agctcgtgct ggatgccaca cagtcaggac tgacagcctt    3300
gaaagtcagt cctttgtggc tgatcatctt tttatcctta aaactacaac cccaaaaaa    3360 actacccaca ttaaatttct gaggttccag tagtgtgggc cgaggcacct ggagccctcg    3420
tggctgctgc ccttcccttc tgtcgcttcg gagttgggtg attcagtgtg tgtggtcagc    3480
tggtaccctg gccaggccca gaagctgctt ccatctggc tgcttcagcc ttgtggcctc    3540
aggtgggtta ttgacctctc agcctcctga gatggaggca ggaagtgcgg gccgttttgc    3600
tttcggctgt aggcgcccac acctgtgccg agttctcagg acgcgcacgc gtgcgcgtgc    3660
acacacacac acacacacac acacacacac gactcgtaaa gccctgggca ggtgggtttc    3720 attttttagta cttctgagct aaaattagtt tattgaagca gctttataaa ggtatttgaa    3780
taggttctag agaccagaa tataatatgt atgtagtgga aatgattgtt ctgtttcagg    3840
acagttaatg tttctgtacc aaagaaaacg agaaacaatg ggacgctgta tgcctacatc    3900
ttcctccatc acgctgggt cctgccgtgg cacgacggga agcaggtgca cctggtcagt    3960
cctctgacca cctacatggt ccccaagcca gaagaaatca acctgctcac cggggagtct    4020
gatacacagg tgagggtctt catgggttac tgataacagg ctgtgcctct ccgtcagaac    4080
ggacatgtct ttctccacac aggtgggcga tgtctagggc tccagtgact tgttgggag    4140 taaagccaaa agccattgga atgttactgg cgtgcatttc tgactttcag ctgaatcata    4200
tccatgagtt tgcagacaag ttttatctaa aattagggac agttgaagtg atcgctggca    4260
ttctcgatgc agagtccctc ggggaatggg ccctctcagt ctctggggc acctactgca    4320 cctggtggga tggagcgctg gtcctgcaga gctggcctgc agcttctcac caggagctct    4380
ggggatgaga gctgggctca ttctgcattc tgtgtaggac tgggctattc ctagatgttt    4440
attctaagaa tgtaattgga gatcatggaa aaggtagagg tacaagttgt agtttgtaca    4500
tctgtagaaa ggtgtatgcg caaataaaaa ctggaagtca cttaagtgat catgaataca    4560
ggccaaggat aaagcaaggg aattctgaca cccaccttg tgttgagtgg aaggtgagat    4620
aatttacaaa acaaggccgg gcgcagtggc tcatgcctgt aatcccagca ctttgggagg    4680
ctgaggcagg tggatcacct gcagtcagga gttcgagact agcctggcca acatggtgaa    4740
accccgtctc tactaaaaat acaaaaatta gctggatgtg gtggcacgcg cctgtaatcc    4800
cagctactca ggaggctgag ggaggagaat cgtttgaacc cgtgaggtga gatgatgcca    4860
ctgcattcca gcctgggcga cagagggaga ctctgcctca gaaaaattta caaacaaga    4920 aagatggcag cttttcagga agaggctgtg aaattgttcc agacagagag aaagagaggt    4980
ctctcggagt tgatgggggtt ttgaaagccc taccaacacc tgctcctgcc tctccccagt    5040
ttgcatctgt ctccttagga acatccctca cctgccctc tccgtgtccc ctcatctggg    5100
```

```
gcccccatcc ctcctctcca gtgtcctgaa aagtgggtgg ggtgatgggc atgtagcatg    5160
tagcgcagga agcctccctt gcaggtagca aatgtgagga ggtgtggaaa accgtttgta    5220
atgtaaatta tcgctaaact gcatctttag gtaggaaatg ggtgaggcga tagtgcttcc    5280
taggatgtat cagatctgag ccgagctaag atttccctgt cagtccatgt cctgtttaac    5340
ttcatgtaag agccgtgtgt aatcctcagt atgtctcctt taggcagccc cacatgcttg    5400
gttttagaag ctgactccct ctcagtctcc ttacagccac agggctgtgt gagccctgga    5460
cttgcacagt cttctgccaa ggtcaggggg ctctcaccct ctcaacttct gagaagtggg    5520
cccacttagt ttgaggacct caaaaaagga attggtgaag tccgtgacca catgttgcaa    5580
agcagcaccc cctggcttcc gtggagataa ggatgggggg ctgtttggcg agagtctggc    5640
ggaattggca gctgtggggc cgctgtgccc tctctgctgg gctctccccc ggttgtgcct    5700
gtgcgtggcc atctgttcac aggttagggt gccgaccctg ctgtccgggc gcggttttc    5760 catgtgcgtg gccatctgtt cacaggttag ggcgctgacc ctgctgtccc gggcacagtt    5820
tgcccgtctg tgtggccatc tgttcacagg ttagggcgct gaccctgctg tcccgagcac    5880
agtttgcccg tctgtgtggc cgttctcttc acaggttagg gtgctgaccc tgctgtccgg    5940
gcgcggtttt tccatgtgcg tggccatctg ttcacaggtt agggcgctga ctctgctgtc    6000
ccgggcacag tttgcccatc tgtgtggcca tctgttcaca ggttagggcg ctgaccctgc    6060
tgtcccgagc acagtttgcc cgtctgtgtg gccgttctct tcacaggtta gggtgccgac    6120
cctgctgtcc gggcgcggtt tttccatgtg cgtggccatc tgttcacagg ttagggcgct    6180
gaccctgctg tcccgggcac agtttgcccg tctgtgtggc catctgttca caggttaggg    6240
cgctgaccct gctgtccggg gcacagtttg cccgtctgtg tggccgttct cttcacaggt    6300
tagggtgctg accctgctgt ccgggtgcgg tttttccatg tgcgtggcca tctgttcaca    6360
ggttagggcg ctgaccctgc tgtcccgggc acagtttgcc agtctgtgtg gccatctgtt    6420
cacaggttag ggcactgacc ctgctgtccc gggcacagtt tgcccgtctg tgtggccgtt    6480
ctcttcacag gttagggtgc tgaccctgct gtcccgggca cagtttgccc gtctgtgtgg    6540
ccatctcttc acaggttagg gggctgaccc tgctgtcccg gcacagtttt gcctgtctgt    6600
gtggccgttc tgttcgcagg ttaggggget gaccctgctg tcctgggcat ggttttctgt    6660
cccagcattg gcctctgttt tcctcactta acagcagatc gaggcggaga agaagccgac    6720
gagtgccctg gatgagccag tgtcccactg gcgaccgcgg ctggcgctga acgtgatggc    6780
ggacaacttt gtctttgacg ggcctccct gcctgccgat gtgcatcggt acatgaagat    6840
gtaagtgggg ccccagagct ggagcgccgg ggggagggtg ctgggaccct ggctggccag    6900
aactcgccag caggtcactc ctgcaccgtg gagtcccctc tgtggggagg cacttgctgc    6960
ccgggcctcc cagctctttc ccacttcctc attgaggttg tgctgctacc acagggctgg    7020 aagggggag aaaggaattc aagctggagc atcctgccct ttgctcctgg ctggcgaagg    7080
cttccatgga gagaaacgg aaggcgctga tgggaacggg ttgcttgct ccccttgtga    7140 ttttttaact tggcttattt agatttactt aaaagttaat ctttagatta tttagtatca    7200
cttgccatca gttaaataca attattggaa ttcacgtgtt tggccacctg agctcacctc    7260
gtctctccca tgtgttgggg atccccccc caactcctgc gccacagctc cgcctcccag    7320
gtggctgcag gtgactcgcc cttccaagtg tagtggccac atcctgggat tgctccgtgt    7380
cagtgcatcc tgggattgct ccgtgtcagt gcgcagaggg ccctgggttc tgctgtacgg    7440
```

-continued

```
ccgtgtccct gtaattcccc cgctcctagt ggccgtggag gcattttccc acctgtggcc    7500
atcacttcct ggggagcggg tctcacaagc gtgcatatgt tgtcaggctc tctgcttccg    7560
tttggggagg ctgtgccctg ggtcattgt gactgagaag cagttgaggg tggtgctggg     7620
ggcacttctc tggggtaaac ccagtgtctg gatgtgttca ttcattgaaa ggtaaaagcc    7680
ttggtgctga ctttggaaag ttgtgctta atcccaggat ccagctgggg aaaaccgtgc     7740
attacctgcc catcctgttc atcgaccagc tcagcaaccg cgtgaaggac ctgatggtga    7800
gtgacacctc tgcccgctgg ttgtgcagct ggcgagacac tgaccccaag actggcccg     7860 cagcccctgc accctaatgg accgggccat tgctgacatt tgacacggtg cttttacccg    7920
tgctgggaag cactgccttc gagtgtgcga gggttgtgac aggggggccc tggtggtgtg    7980
ctgggtttgc cgttggctgg ctgcggggtc ctgctgagcc tctggactgt cactggtgaa    8040
aggcccctgg aagattgttt atgcagcgca tagagggcag cgcttagaga gcaggcacat    8100
gagcaccgtg tgaaacagcg tctgcgtgtg agctcctggt gtgccatgta gattaattca    8160
cagtatcctg agcaaactcc tgcttcccc accaggctg gtcctgcaca ggcggccaga      8220
ggagcgggtg acagcccttc ctcggagctg gagcccccgg ggtggcccct ggcaaggcgg    8280
aaggcctttg cgaatagaag tggctgctct ctgggtctg gcgccctgtg attacgggca     8340
gtgacagcgc ctgctctccc atagttgctt tgagaggaga tgaaatgtgg ccaacctttg    8400
gccagtattg agactcacag aagcagttaa tatttaatgt ctcttactgc acatgaggca    8460
ctgtgctaag cactttgtga atctttccgt aattgtggtg ctgggagctg tggcgttgtt    8520
tcacggatga ggttatttgg ggttcagagg tgaacgctca gctggggccc tgcaggatcg    8580
ctgccctgcc ctgcctccct gcaagccatc actgtcactc cggatcaccc actaggagcc    8640
ggccacttcc acttaaggct ctcggcacct ctgacctctg aggcgggccc tttcccttt     8700 tttgttgaag aggaaacagt cctggggaga gcagagggct tgctagcggg ggggtgcagc    8760
tgggaaacgg agaagcgagc acctggctgc tttgatctct gcccaggccc tgctgcctcc    8820
tcctgactgc ggctctcaga acagtccccc tgtactgctg ttccctcaga ccccttgcag    8880
tccctaacat actgcctcct tcacttctgg ggtcactgat tgctcctata caacctgcag    8940
gctgggggct gcacaggcag tggctggcga gcaggtctgg cgctgcagcc tatccctgag    9000
tagtttctct gtcggcccct gcaattccaa cctctttctc tgtttgctgg agtttgctgg    9060
tgtgctgctg acaaacctca ggacagcaag ttctgctaaa atgccccata cagagctgtg    9120
tgagctgtgg caccagctcg tggtcacctc ttgtgaagcc tcatgccgct gactccttgc    9180
aggcattcag gagatggtgg acaggggcag gcagctgcag aaggctgccc tgtgtgtctg    9240
tctgcagatc tgtcttgtta gaggcccggg gcaggctttg cggcgcagct gtgccagtgg    9300
tggcctgcgt tccagtggtt atggagacac gtgtgccgac agcagctttt ccccaaatc    9360 acagtctctc tcatgtgtcg ctgttgctgt gtctcacttg gggccagatt cgagaggtgc    9420
tgtcttgaga gaggaagcag gcagctggga tgcagcaggt gcaggaagtc ggcaccttct    9480
gtggctgggc ccagcactgc cagatggagg aggcagtgac acccttcgga cacgcttggc    9540
agctcgaggg gtgcctggag gccaccatcc atgtgcactg atgccacttg gctacgtggg    9600
gcgccctgac agccgctctc agggcaacct ggcacctgct ggttgtggct ctgattccac    9660
cacaccctga caccagcagt gcccgccata gcagagcagg tggattagag cacagccctc    9720 gctgatgtt ccagcacgtg gagggtgcg ggtcagggct tgaggcaggg caggtggatt      9780
agagcacagc cctcgctgga tgttccagaa cgtggagggt ggtgctcacc gggtgtggtc    9840
```

```
actgcccacg tgctgtaggg tgtgggctcg cgcttgtgaa cccgttcctc accctcctac   9900
ctcggcaccc tgggacctgg cccacagcct gtgtgcgtga ggccccggca ggctgcagga   9960
ctaagctcgt ggttctgaga cctacacatc caccctactg ccctgctag ctttgcgttc   10020 cagaagcttt ctgttgtccc cacggccacc ccctgctctg tgctttaggc cctgaggcac   10080
tttgcccatg tgctgcaggg ctgtgcttgt cccgtggtct ccaactctta ggacaggcca   10140
gggctctgca ggccaagctc agcgccgtat gctgcgccat ggagtcctag cagctgggtg   10200
gcaagcacca cctccggggc accaggactt gtgcggctta aaattgaagg gcacgtgca    10260 gcaaaacaga ccaggcactg ctagcgctgc tgagctcacg gggtcctggt gggggtggga   10320
acctccctgt gctggaacgc agcacgctgg ggcctgaggc ctgtggtgac agaaggaggg   10380
accgggggat gcttgctggg cccagtcatg gctgacctgg ggccacacag ggatgggaag   10440
ggggatggca gggttggcga gggctgccag gcagctgggt gcaagggtat gagggcaggg   10500
ccctcagtgt ggctttcttc atcaggtcat aaaccgctcc accaccgagc tgcccctcac   10560
cgtgtcctac gacaaggtct cactggggcg gctgcgcttc tggatccaca tgcaggacgc   10620
cgtgtactcc ctgcagcagt tcggtatgtg ccgcacacgg ccggcgcctg ggtgaggccg   10680
ccctggagcc cctcgggcat ccaagtgcga atcctgacac aggccggggc ctcctcgcct   10740
cctgctgcag atccttgcac agacgttgaa tcagaggcta gcagcgcctg cctcacttct   10800
ctccttggag atgacctggt tgattgtctg gaaattggct ttattaagaa cataatatgt   10860
gaaatgccat gagtttggtc aaatgaacct taactgttga tgagatttat ttttattgtt   10920
tgtttgtttg tttgtttgtt tgttttgaga cagagtctcg ctctgttgcc caggctggag   10980
tgcagtggca caatctctgg ttactgcagc ctccgccccc cggattcaag cgattctcgt   11040
tcctcagtcc ccccagtagc taggattaca ggcgcgtgcc cccacgccca gctaattttt   11100
gtatttttag tagagatgga gtttcaccat gtttaccagg ctggtcttga actcctgact   11160
tcaagtgatc tgcctgcctg agattcccaa agtgctgggt ttacaggcat gagccactgc   11220
gcccggccta aattttata ttgaaaactg tatttgtaat gttaggtaag attgacattg    11280
cctgttttat attgtatgtt ttttttttcct tgacagggtt ttcagagaaa gatgctgatg   11340
aggtgaaagg aattttttgta gataccaact tatacttcct ggcgctgacc ttctttgtcg   11400
cagcgttcca tgtgagtcat ccaccggggg gcttgccgca ggcacttggg gggctccctg   11460
ggccccgggc ctcctgcagg ggtcctggac ctggggtttg tgggcgccgt ccagccctgt   11520
ggccctcaag tgtccactcc catcactcag cagccagcac gcctgacacc aggcgaccat   11580
tgtcccagtg ggcggtttct cccagttctg aaaagggagg gaccataaag ctccgtccac   11640
agccttggcg acttgggctg tgctggcttt ggggcggtt ttgaaaagga tccagggtac    11700
tctgagcagt gtccacacca atgagatgaa taggtgcagg catctcactc tcccctgccc   11760
aggccccgac cccatgcaga gccaggggcg gagctgggca gcctctagca gaaagtagtt   11820
ctcttgtata aattctaaca cactgatttt taaatgtaaa aagtcagtcc tgtgtgtata   11880
cagtagttcc cccttacccg atgtgtatac agtagtcccc ccttatcctc atccggtgtg   11940
tatacagtag tccccccctta tcctcatccg gtgtgtatac agtagtcccc ccttatcctc   12000
ttgcggtgtg tctacagtag tccccccctta tcctcagccg gtgtgtatac agtagtcccc   12060
cttatcctca tctggtgtgt atacaatagt ccctcatcct catcccgtgt gtatacagta   12120 gtctccccctt atcctcatcc ggtgtgtata cagtagtccc cccttatcct catctggtgt   12180
```

```
gtatacagta gtcccccctt atcctcatct ggtgtgtata caatagtccc cccttatcct    12240
catccaatgt gtatacagta gtcccccctt atcctcatcc cgtgtgtgta tacagtagtc    12300
cccccttatc ctcatctggt gtgtatacag tagtcccccc ttatcctcat gtggtgtgta    12360
tacaatagtc cctcatcctc atcccgtgtg tatacagtag tctcccctta tcctcatctg    12420
gtgtgtatac agtagtcccc ccttatctgg tgtgtataca gtagtcccccc cttatccggt    12480 gtgtctacag tagtcccccc ttatcctcat ccggtgtgta tacagtagtc cccccttatc    12540
ctcatccggt gtgtatacag tagtcccccc ttatccggtg tgtctacagt agtccccccct   12600 tatcctcatc cggtgtgtat acagtagtcc cccttatcc tcatccggtg tgtatacagt     12660
agtcccccct tatccggtgt gtctacagta ttcccccctt atcctcatcc cgtgtgtata    12720
cagtagtccc cccttgttct catccagtgt atatacagta gtccgcccct tatcctcatc    12780
tggtgttata cagtagtccc tcatcctcag ggggtgtgtt caaagaccct cattggatgt    12840
ctgaatatgt gtatcaaata acgtaatgaa tgaatatatg tattatgtaa tggttttgat    12900
aaagttcaat ttataagtta agcacagtaa gagattaccc acaataactg gtaacagaaa    12960
caggacagga cagtgtgata aagttacgtg ggtgtggtct cactctcaga atatctgtct    13020
catcgcactg ctccgtgcta accgaaacca tggacagtaa accatgggta aagcaaggct    13080
gctgtgctct tactgttgtt cgtggagctg agctgctagg gagagccatc cttgtggctg    13140
ttaggctggc ctgtggttag gcggcaccca ggagtgcggc cggcactggt tctgagtgcc    13200
tgggagtttg gctgccagtc aagctaaaac tttccaaagc cgtactagag aattaaacga    13260 ttttattaa aaggtcagtg tctctaagga tgagatcatg catggttagg tttttttaag     13320
ttttttttgg agacaggtct cagtacgttg cccaggctgg tctcaaaccc ctgggcttag    13380
gtggtccttt ggccttggcc ttgcagtagc tgggatcaca ggcatgggcc accatgccca    13440
gcccttgcgt ttttagcaca gttgagagat gaggctgccc tgagtgggca acccgaga     13500 gcaggggtgc ccagccaggc ccatgatcca ggggaatcca gagcctccaa ttgcctgggg   13560
gcctttccag cagttcaagt caaaggtacg tattatttca gaagtgcccc tgcaaagccc    13620
gcctgggcac tctaggttct gacatggcag gccaggcgcg tagaggcatg ggtcccgagt    13680
gtagacactt atcctgatgc atcctgaggc tgagtacacc tgcagtctca cggtcacaca    13740
cgaagcctct atctctgtct cacaggagat ggaaacagca ggagatgtga gttgctgtcg    13800
tgtgtgttct ctctagcttc tctttgattt cctggccttt aaaaatgaca tcagtttctg    13860
gaagaagaag aagagcatga tcggcatgtc caccaaggca ggtaggcccc ccgagcgtgg    13920
ccctgctcag atactctgcc ccagggagct cactggagcc tgcggtagag ggctgcctgc   13980
ctcactgctg gctgcagaca cagcccgggg tgtgtgcttg gctcttgaga agcctctgag    14040
accaggcacc gtaaagccca gggagccgtt gcggcaattg tggtgggacc atcagaggct    14100
gcacggctca gggcctccag cggctgcaca gctcagggcc tggctgcgga ctctggcgtg    14160 catgggtct gggtctgggc tgtggagagt gagatgcatg gacctctcga gccttcccgg     14220
ctgctcatgg gcgctgagca gggctggggc ctcacatccc ctgtcttggt tccctcgccc    14280
cgtcctcccg ccggtgttcc ttccccgacc agcgcaggcc tgggcgtgtg gggcctgcca    14340
ggtgatggca gttaataggc ccgtggtgct gtgcccagca gtgacaggca gtgtgcagct    14400
gttaggtagg gcagtcaggg acccctgagg ccaggcagcc caggcaggag gcctgccaag    14460
atctgggacc agtgttcctg gccaagggtg cctgccgtgg tttaaggggc caagtgagt    14520 gagggtcct cctgaccttg caggggtgga ggttgtcaca gtggggtggg gagcggcggt     14580
```

```
ctggacaggg gcgagtggtt gatgggtgtg aggacgagga gtgggtgtgt cctgttggtt    14640
aggagtgagg agcatttggc tccagtatca gacccgaaca agttgttttt ctcgcatgga    14700
aaagacgccc aagcaggtgg ccctggctgc ctgggggccg tgccgtgttc tgcgttgttg    14760
tctcctaacc ctaatgcctt tcctggcgtc ctgggttgga gtggccagca gacagtggct    14820
gtggccttga ccactgtttg tcctgtggct ccatggatct gcttcccctg cttgccctca    14880
gggcttgcag gaggaggaag acgtgttgaa taagctggag tggttcttaa ggtacagctg    14940
gggaggaaac aaatccagac ttgaaaagcc acgcacttat cacagaactg cataagaca     15000 cgcccggaag caaagctgtg ctggccccgt catccgacct ctgcccacgt tccatgctca    15060
tttgcaagtg tggctcagac acgtgtttgt ggagctggtg tggggccagc tgttcagttc    15120
agcagccttc caaacacttt cctagctgct gaatgcttca ttgttctttt taaacggggt    15180
gacgtggact ggggagtacc tgaagcttct tgggcgtggt gggttgggat ggggggactgg   15240 gggtatgtgt gtgacttggg gaacacaggt ggggtctgcc ctgcaccccc tcccagcccg    15300
accatcctgt ccccagtgct ctggcgctgc ttcagcaccg tggtcatctt tctgttcctg    15360
ctggacgagc agacgagcct gctggtgctg gtcccggcgg tgttggagc cgccattgag      15420 gtgagttccg ggcagtgacc tgaactgtct gaggtccatg tgcctccacg cactcaggaa    15480
aggctttcag ccccgggacc tgagaccttc tgtggaagcc tgtgtgcttg ttcccgatgg    15540
cctcagtgtt ctggaagctg taggatggca ggcagtgggt gtaaaggctt tgaacaagtg    15600
gagagcaagg aaatgcgtgt tcgggtggta tcagctcatg aggctctgtc caccaagcag    15660
tggtgagtcc tgaggccctg tccaccaagc agatagtcct gaggctctgt ccaccaagca    15720
gtggtgagtc ctgaggccct gtccaccaag cagagagtcc tgaggccctg tccaccaagc    15780
agagagtcct gaggctctgt ccaccaagca gagagtcctg aggctctgtc caccaagcag    15840
agagtcctga ggccctgtcc accaagcaga gagtcctgag gccctgtcca ccaagcagag    15900
agtcctgagg ctctgtccac caggcagaga gtcctgaggc cctgtccacc aggcagagag    15960
tcctgaggct ctgtccacca gcagagagt cctgaggccc tgtccaccag gcagagagtc      16020 ctgaggcccct gtccaccagg cagagagtcc tgaggccctg tccaccaggc agagagtcct    16080
gaggccctgt ccaccaggca gagagtcctg aggccctgtc caccaagcag agagtcctga    16140
ggccctgtcc accaagcaga gagtcctgag gctctgtcca ccaagcagag agtcctgagg    16200
ctctgtccac caagcagaga gtcctgaggc cctgtccacc aagcagtggt gagtcctgag    16260
gccctgtcca ccaagcagag gcctgaggcc ctgtccacca aacagagtgt tttcatgtgc    16320
ttgagaaatc ccaccatgtg caaagcagag gtgtaaaccg tggggccttg agaggctcgt    16380
gctgtggctg gagatctgag cacagcgcc aggtaggcac tgacggaaat cactcggtgc     16440
cctgtggtcc agccttggtt gttccggagc tcagaaaagc cggccaaaag ggagcctcgt    16500
ggggcaagac cagctcagga gcaaacccctt gaggggggcg atggccttca gggtgagagg   16560
gcccaggctt aagcctagct cctcactgag ctctgtgcca caccggcagg agccggagtc    16620
tgaggtctct gcagttggtg gcccaccctgt gggtggggggc ctctgcggcc gtcatgcctg   16680
tagaggagga gctggatgca atgtctctgt agaggaggag ctgtatgaaa tgtgtctgta    16740
gaggaggagc tggatggaat gtccctgtag aggaggagct ggatgaaatg tgtctgtaga    16800
ggaggagctg gatggaatgt gtctgtagag gaggagctgg atgaaatgtg tctgtagagg    16860
aggagctgga tgcaatgtgt ctgtagagca ggagctggat gaaatgtgtc tgtagaggag    16920
```

```
gatctggatg gagtgtccct gtagaggagg agctggatga aatgtgtctg tagaggagga    16980
gctggatgga atgtgtctat agaggaggag ctggatgaaa tgtgtctgta gacaaggagc    17040
tggaagaaaa ctgtctgtag aggaggagct ggatgaagtg tgtctgtaga ggaggagctg    17100
gatgaaatct gtctgtagag gaggagctgg atgaaatgtg tccgtagagg aggagctgga    17160
tgaaatgtgt ctgcagagga ggagctggat gaaatgtgtc tgtagaggag gagctggatg    17220
gaatgtgtct gcagaggagg agctggatga aatgtgtctg tagaggagga gctggatgga    17280
atgtgtctgt agaggaggag ctggaagaaa tgtccctgta gaggaggagc tggatgaaat    17340
gtgtccgtag aggaggagct ggatgaaatg tgtccgtaga ggagtagctg gatgaaatgt    17400
atcctgtaga ggaggagctg gatggaatgt atcctgtaga ggaggagctg gatggaatgt    17460
gtctgcagag gaggagctgg atgaaatgtg tctgtagagg aggagctgga tggaatgtgt    17520
ctgtagagga ggagctggat ggaatgtgtc tgtagaggag gagctggatg gaatgtgtct    17580
gtagaggagg agctggatgg aatgtgtctg tagaggagga ctggatgga atgtgtctgt    17640 agaggaggag ctggatggaa tgtgtctgta gaggaggagc tggatggaat gtgtccgtag    17700
aggaggagct ggatgaaatg tgtctgtaga ggaggagctg gatggaatgt gtctgtcgag    17760
gaggagctgg atgaaatgtg tctgtagagg aggagctgga tggaatgtcc ctgtagagga    17820
ggagctggat gaaatgtgtc tgtagaggag gagctggatg gaatgtgtct gtagaggagg    17880
agctggatgg aatgtgtctg tagaggagga ctgggtgga atgtccctgt agaggaggag    17940
ctgggtggaa tgtccctgta gaggaggagc tggatgaaat gtccctgtag aggaggagca    18000
ggatgaaatg tgtctgtaga ggaggagctg gatgaaatgt gtctgtagag gaggagctgg    18060
gtggaatgtg tctgtagagg aggagctgga tgaaatgtgt ctgtagagga ggagctggat    18120
ggaatgtccc tgtagagcag gagctggatg gaatgtccct gtagaggagg agctggatgg    18180
aatgtccctg tagaggagga gctggatgaa atgtccctgt agaggaggag ctggatggaa    18240
tgtccctgta gaggaggagc tggatgaaat atgtctgtag aggaggagct ggatggaatg    18300
tgcctgtaga ggaggagctg gatggaatgt gcctgtagag gaggagctgg atggaatgtg    18360
tctgtagagg aggagctgga tggaatgtgt ctgtagagga ggagctggat gaaatgtccc    18420
tgtagaggag gagctggatg gaatgtgtct gtcgaggagg agctggatga aatgtgtctg    18480
tagaggagga gctggatgga atgtgtctgt agaggaggag ctggatggaa tgtgcctgta    18540
gaggaggagc tggatgaaat gtgtctgtag aggaggagct ggatgaaatg tgtctgtcga    18600
ggaggagctg ggtggaatgt ccctgtcgag gaggagctgg gtggaatgtc cctgtagagg    18660
aggagctggg tggaatgtcc ctgtagagga ggagctggat gaaatgtccc tgtggaggag    18720
gagctggatg gaatgtgtcc gtagaggagg agctggatga aatgtgtccg tagaggagga    18780
gctggatgaa atgtgtccgt agaggaggag ctggatgaaa tgtgtctgtc gaggaggagc    18840
tggatgaaat gtgtctgtcg aggaggagct ggatgaaatg tccctgtagg ggaggagctg    18900
gatgaaatgt ccctgtagag gaggagctgg atggattgtc cctgtagagg aggagctgga    18960
tgaaatgtcc ccgtagagga ggagctggat ggaatgtccc cgtagaggag gagctggatg    19020
gaatgtcccc gtagaggagg agctggatga aatgtgtctg tagaggagga gctggatgaa    19080
atgtgtctgt agaggaggag ctggatgaaa tgtgtctgta gaggaggagc tggatggaat    19140
gtgtctagag gaggagctgg atgaaatgtg tcggtagagg aggagctgga tggaatgtcc    19200
ctgtagagga ggagctggat gaaatgtgtc tgtggaggag gagctggatg aaatgaaatg    19260
tgtctgtcga ggaggagctg gatgaaatgt gtctgtagag gaggagctgg atgaaatgtg    19320
```

```
tctgtagagg aggagctgca tggaatgtgt ctgtagagga ggagctggat ggaatgtccc   19380
tgtagaggag gagctggatg aaatgacgct ggagctccac aggcagggtc cctccatagg   19440
tacgagtcac agtgccgtgc ccggctctgg cacccgtcct gagctccgtg ggtgatgcct   19500
tccaagcatt tagccatgag gtggcggctc tcagagcggc cccaaaactg gctccagggc   19560
tgcccgagtg gcaggcagaa gtaggtgggg gcttatttgg gtgcaggcag agtggcgtaa   19620
agaactgccc tcacatgctg tttttgttgt ccgctgggcg gtggctgtgc agcccacctg   19680
accaggtacg cctgccgtgt gtgggttaga ggcccaggtc cagcctccag cgctctggcc   19740
tgagctgtgg gagggacagg aagaggacag tgggctgcgc ggggccatgg gcagcaggtc   19800
ctacccgtta ctgtctgggt cgttcattcg tggctcctgg ccttcgaata ttaaaggaac   19860
tatttcctga tttctcccct cagctgtgga aagtgaagaa ggcattgaag atgactattt   19920
tttggagagg cctgatgccc gaatttcagg taggatttag ttgtaatggc tgaaccccaa   19980
gcctctctga agagtgtgat tttgccccct gtgcaaagag taagatggcc atctgcagat   20040
gagtcactgc gggcctctgt caggggagcc tccgtggtgg aggcagcact ggtttctgat   20100
cgcagccact ctcttcgcct gaggattccc cggtcatata cctagttctg accgtcttca   20160
gtgcagacgg cagcacttct gggcctgagc cggcctctgg gaggaaggat gctggctggc   20220
cagcacgtgt gcttcgtttt ggcacccttgt ccagaggcgc tcccgaggct ggtgctgact   20280
ggggtccgta cagtcctggc agtcctgaag tgagtgagcc cctgccctga gctggtggct   20340
gccccagtgc ctgggcgccc ataaggcccc taggcagatg agggctgggg cagagctgga   20400
gttgaatctc agtgcccacg gatggacctt gattgaggcg gggccctcag cagtcacagg   20460
ctgagatttt ccatgctgtg ggcagggggg tcaggaagcc cagcacacgc agcgcagcca   20520
ctgtgttcca ccttgcccca tggctcccgg ccggctggtt cggagcagtg ttggctgtgc   20580
ctgtgtgctc tgcagtgttc tcactgaagc ggtggcactg aaaactgagc cacctgagca   20640
aggaacagca gtgaggccgc gttgccccca tcaggcttgt gggacccagg gccagggtga   20700
ggcgggaagg atccatgcgg atccccgtcc tctgggtcct ctcctcgcct ggtagggacc   20760
tgagcgccct ctgtagtgag gcctgggtca gctctgcagc catatgtgac gcccccttagt   20820 cacagctcag ctgtgctcag atcctccctg agtctattaa tatcactgtg ttgaatttca   20880
caacagtttg gcacttacag cgaatctgag aggaaaaccg aggagtacga tactcaggta   20940
agtcacttgt gattcagggc acgtgcatgc caggcaaatc caacaccctc aaagacgggt   21000
cttttactgt cattgctcag tgcggaagtc tccttggagt acgggtcagc ccgccttgag   21060
cagggatccc aagagtgaac acataaaacc caaatttctt actgggaagg gcggggctc   21120 gcagagactc atttcccagt ccttacaggc acagcctgcc tgtgtcaccg tatagtaggg   21180
atattttcat cgtttgtaag tcacattcgc caggcagctg acgcaggcca tggtgtctgc   21240
tgtggttgct gggaacgcac ttgccgtcac caaggccata atggccgcgg ccgcacagtg   21300
gcctggagga atggcccag cagcacaggg cgtcaccttt ccccattgct gttggggag   21360 ctggaattct cagttccagt taatagaaca tttctgcaca gatgattta gtttggttta   21420 atcttcacca gcttatatcc aacttgcatg gcgttgtaaa gctgaaatca gaatggatac   21480
agctggcgat gtaactacat tacttagtag gcagtttttt ccggtttctt tccattatgt   21540
ttattgatct gttgtggggtt ggttggtttt gaccaaccag aattgatcta ttattgttaa   21600
ctagcgcctg tagttacacc cgggctctgg cgtgtgcggt gcctcctggg gctgtggcga   21660
```

```
gtgtgcgatg ccctgcctgt gccctcacg ccgccccctg cagagcagcc ctgccaccct   21720
gagcgctgta gctcgttctg tctgtccctg tcggggtgag ctccatgcag tgtgtttaca   21780
gaggcttggc gtttgggcct ctaactggaa gccatctttg ttccctgcag gccatgaagt   21840
acttgtcata cctgctgtac cctctctgtg tcggggtgc tgtctattca ctcctgaata    21900
tcaaatataa gaggtaggag gccgcacacg cttcccctgc tgcgtctttc ccctgagaaa   21960
gccatttgga tgactgagcc agagcggggt gcgactggag ggcaaactcg gggccggggc   22020
acttgggcca gcgcctggga ggggtcctgc ccctgcagct gcacacggtg ggctctgggc   22080
ctcagtgtcc ccctggtaag gtgtagctga gaggactgac tccagccacc aggcttcatg   22140
ggaggcttgg gcctgagctg agaggggtcc tggagcccct ggcctctgct gcccgtgtgg   22200
ggtgctggcc ctgagctgag agggttcccg gagccccgg cctctgctgc ctgggtgggg    22260
tgttggccct gagccgagag gggtcctgga gcctccagcc tctgctgccc gggtggggtg   22320
ctggccctga gccaagaggg atcccggagc cccagcctc tgttgcccag gtgggctgct    22380
ggccctgagc caagagggat cccggagcct ccagcctctg ctgcccaggt ggggtgctgg   22440
ccctgagctg aggggttcct ggagtgcccg gcctctgctg cccggcagg tgctggccc     22500 tgagctgaga ggggtcctgg agcccctggc ctctgctgcc caggtggggt gctggccctg   22560
agctgagggg ttcctggagt gcccggcctc tgctgcccgg ccggggtgc tcagcgctat    22620 ctccagcttg agaaccaggc tcagcactgc tgctcttggc tgccgagctg ccgtgagagc   22680
atctgggtat tttcagagga ttttaatga aagaattatt ttcatcaat ttaatacaga     22740 tattaagcta tgcgagaaat aggacttctc ctttttttc cgtttcagct ggtactcctg    22800
gttaatcaac agcttcgtca acggtgagtc catgtgcttc cctgcttcag tactagtgtt   22860
tccagcaggc agcgatttaa ttgttcttgc attgaaaccc agtgtggcaa gccccctgt    22920 gatttgaggc taatccctcc ccaccctgtt ctggcacatg tgcggtgccc agggctcccc   22980
ccaggctgtg agcagataaa gccctgcgtg gcttcacaac agtgactggt tctgagaaac   23040
aggtccttgt acaagcgaca gggagtgctc acaccagatg tggcagcccc tccacgccag   23100
gctgtgtggt gcagccgcct ggtatatgtg tccatcgctg atgaaaacag cattgtgtgg   23160
tgcatgactg ttgtctgttt tcttcatgga aacaaggaaa cctaagcatt aaaacaacac   23220
catccacgtc tggttcctta gagcaaatgg aagcaccagg ctctggtgca cggcgcgccc   23280
cctcctgcag atgcagtgtg gggaccctgc agggccctgt gctcggggcc acatgtcctg   23340
ggaggcccgc ctgccccagg tggcaccttc agctgcatgg gctgctgtgt ccatccccca   23400
gccccaccag accagccctg atcgcagctt tgtggtctct ttgggaagtg gtcccgtgag   23460
cattaagggc gagggcctgt ctggtgcaga gcaggtgggt cccgcactgc cgtcctccct   23520
ggtaggagtc ccacacctga ccctggggc aggaccttgt gggtcaggag gccgtgtcct    23580
catagcccca gggtgctcca gtgctctcac tgacttgacc ccgtgggcag cagttacact   23640
gattaataaa tagaagagct ttgctctcca aagttgtcgt agactcttga taaacttacc   23700
agccagaaag ctgcttcaca ccatgatgga ctctgaagtt gtctggatag cagaccttgt   23760
tttctgccca ctatgcatag acgtggcagc tcggccctcc acacctcgtg agtgccgtct   23820
gtgcgtagat gtggcagccc ggccctccgc acctcgtgag tgctgtctgt ctttctgcag   23880
gggtctatgc ctttggtttc ctcttcatgc tgccccagct ctttgtgaac tacaaggtaa   23940
ggcggtgtgt gctgccgcg gccccggcccc cgtctcctgt gctgcccaca gctgacctgg    24000
gcctgtctct cctgtttcag ttgaagtcag tggcacatct gccctggaag gccttcacct   24060
```

```
acaaggtgag tgtgacagcc ggtgaggaat cccttctcac tgagcagagc gtgagcaagg    24120
gcgtcttcca gccaacagca ttactggggc catctctgcc cagagtgcat ctgcacctgt    24180 cccttcatt gaagaatatt gaggaggctc ctttaaaaaa aaaagcgaag agctatagag    24240
taacttcaga ccctgaaaga ctggggtggt tctctcactt gtcacagatt tggttttctt    24300 tttcttttt agtgtttatg tttcttctta gcacatgtgt caagacacag acccctgtg    24360 gctcagtaac cggtgcctgg ggacaacgga ttcaggcctc ccaggcagga atggaagccc    24420
ccatgggccg tggccattcc ccgctggcag agctgtggag gcccccttgg ctccgtgtgg    24480
gattagaagt gcctcggcat tgcaggcgga gctgagttaa tgggacatga tttgcactttt    24540 tctgaagtca attacaagct cccagaggaa agggcaatgc tcaggtggct ctgcccttgg    24600
ctctcccctt ggctgtggtc tcgggcggct ctaaccttgg ctctggtctc aggtggctct    24660
gcccttggct ctgtctcggg cggctccagc cttggctctg gtttcaggcc attctctttg    24720
ggttccccga tgtgggagcc tgggcaagac ccgcagtgtg tcgggtgcca gcagctgtgg    24780
ggagcccatg agggaacaga gctccgtatc tccacttgcc ggctttctgc tcttttttgtt    24840 gttgctgtga ggagttccag ttagttccaa gcatctgcca aaagccgttg gcttggttag    24900
gttaccaaaa acagtaggat tccagcccca gcaactgggg ttcaccctcc tcccgtctgg    24960
ccctgcaggc tttcaacacc ttcattgatg acgtcttttgc cttcatcatc accatgccca    25020
cgtctcaccg gctggcctgc ttccgggacg acgtggtgtt tctggtctac ctgtaccagc    25080
ggtggtgagt gcggctgcgt atgctcggcc gttgctccgt ctcagcggcg tggctgctgc    25140
tgaacggaat gacggctttc accgcaccct gcgcctgttt atccatttga gggaaaagat    25200
aatttgcagg tggtggtttt tcctgtcttg cctaaacttg ggttccagtt gcccatgata    25260
tgtcctggca agaaactgtt ccagctctgt ctcctcactg tgctttagaa atgctcgttt    25320
ctatgtgaat tattgatgag ccactgaaag caaatgtctc tccttaagcg atttattac    25380 ctattcacag tcattgctat tgagcagaac agagaccgta gcatggctaa tccatacttg    25440
gcgctagcct cgaagtgtcc agccagcagt gtggacctgc agggcacaat gtcactgggg    25500
agctcactca cctcagcatt ggccgcaccc cttaaaccag ccaccagggc ctctgaagac    25560
tgcattgcgt ggacctctca gcttggcctt caggttgaag gctgacggct gaggaaaagg    25620 cttttgtggaa ttttctaaag gcagaggttc aggcccacc ccgggcctcg gaattttcca    25680
aatgcagagg ctcaggcccc accctgggcc tcccgcttcc ctccagggct gacatctgcc    25740
ctctcagtca gcaaaacctc cctccagctc tgctgtgcca gggtaggagc cagggatctg    25800 ggctcccct cgggagggtt gcatctggac cactgcaagc actgccctca cctccagtgc    25860 cggcccagg gccttgtcca ggggtcgaag gagtgtgtgt cacccccaag acctgctgcc    25920
aagtgtctca gagcctcctg gctgtgtcct ttctctggcc ctcaaggtcc ctttccccat    25980
ctccctcccc cgaccaggag gccacctcac acaccacggc tgtgacactt ccctgtgccc    26040
ttccctcagg gcctggggcc atcctactag tgcaggagag ggatcctctt cccccaggcc    26100
gtcctggcgg gtcctgccta ggtcggggt gccggcccct ggggagcgca gtgctcccgt    26160
ccccgccctg tctccacact caacctcgcc aggtgttcag agcctctgtc ccagccagca    26220
tgaggctggc atggttctgc ctggtttaac tctttgttcg ggtgcagttg gcacatccac    26280
acagtggctc atgccgcc ttgcccagct ctccaggcct ggccgccggc tgccccccc    26340 caccctgttg ctgtctcgtg cagcccctgc acgggagctc cagcttgtgt cagcgggaag    26400
```

| | | | | |
|---|---|---|---|---|
| ggctatttca | ccataagcaa | cactcacact | cacacggggc | ttggttcctg tcccccgttc | 26460 |
| accattctca | gatccccag | ctggccgcct | gccccctgca | gagcctgagg ttgtccaagc | 26520 |
| cacggagccc | cggacgctgc | tgcgcctggt | gtggttgtct | caactgtgag cccttcaagt | 26580 |
| ggctcccaag | tcctcgcagg | tggcccgggg | cgtgcctgaa | actgtgctgt actcaggctc | 26640 |
| tgtgttaatg | gctccagacc | tgcaaacggt | gtttggccag | gatcacaggg cccttggtgg | 26700 |
| gcagcaggtc | tgttttttaag | ctgaaaccct | gtacttctgt | tcgcggccgt gtagagctgc | 26760 |
| cccttatgcc | acagcttcct | catccatacg | tagggggtgat | gttggcaagg cctccggggc | 26820 |
| gctcaggatc | aaaggcggcg | gcagtgtcct | gccaagtgtt | cacagctgat gagacgtggt | 26880 |
| ccctgaacac | agcggttcct | gttctgatca | ctcgagtctc | cgtgatgcca ccgttcccag | 26940 |
| aaggcagccc | gtgcagcctc | cgggtccccc | cttcagccat | ggcagcccgt gcagcctccg | 27000 |
| ggtcgtccct | tcggccaagc | ttcccttcc | ttgagagcag | cacgctggcc tggccatgca | 27060 |
| gaacaaaaca | caactcagaa | atccctcctc | agccctcggc | agtaaaactt ctgaggattc | 27120 |
| gactttttag | ttaatttgct | cactgtgca | gctcactgga | aaataaatcg aggatgccaa | 27180 |
| gtcctcctct | tagaaaaata | gcccctgcag | tggggttttgc | tgatgtgctc atttgtgtca | 27240 |
| ttgcaggctt | tatcctgtgg | ataaacgcag | agtgaacgag | tttggggagt cctacgagga | 27300 |
| gaaggccacg | cgggcgcccc | acacggactg | aaggccgccc | gggctgccgc cagccaagtg | 27360 |
| caacttgaat | tgtcaatgag | tattttttgga | agcatttggga | ggaattccta gacattgcgt | 27420 |
| tttctgtgtt | gccaaaatcc | cttcggacat | ttctcagaca | tctcccaagt tcccatcacg | 27480 |
| tcagatttgg | agctggtagc | gcttacgatg | ccccccacgtg | tgaacatctg tcttggtcac | 27540 |
| agagctgggt | gctgccggtc | accttgagct | gtggtggctc | ccggcacacg agtgtccggg | 27600 |
| gttcggccat | gtcctcacgc | gggcaggggt | gggagccctc | acaggcaagg gggctgttgg | 27660 |
| atttccattt | caggtggttt | tctaagtgct | ccttatgtga | atttcaaaca cgtatggaat | 27720 |
| tcattccgca | tggactctgg | gatcaaaggc | tcttttcctct | tttgtttgag agttggttgt | 27780 |
| tttaaagctt | aatgtatgtt | tctattttaa | aataaattttt | tctggctgtg gcattttttct | 27840 |
| tgacctggta | taatgaaagt | atttcggata | tttgagtttta | acccttttcc agaaagtaat | 27900 |
| acatgatatg | gatttatttta | tgcattaaaaa | gagcaaattt | aaagagccct ttgcaagcct | 27960 |
| ttgagtcatg | agtgttctta | gatacgtagc | atcttagttg | tttaagacta aactattgta | 28020 |
| cagagccatg | acccatcagg | tcaagcttat | cttgccctag | gttgaggcag agagagagaa | 28080 |
| atggaataga | aagatgggtg | gagaactgct | ggactcggtg | tgtagtgaag tttaatgttt | 28140 |
| gttgaagtta | gttttttgtgg | ggtttgttgt | tctcagctca | cagcagcctc cacctcccat | 28200 |
| gttcacacaa | tcttcttgcc | tcagcctcct | gagtagctgc | gactacaagt gtgcaccacc | 28260 |
| acatccagct | tttttgtatt | aatatttttta | gtagagatgt | ggttttgcca tgttgtccag | 28320 |
| gctggtctcg | aactcctgat | ctcaagtgat | cacccgcctt | ggccttttga agtgctggga | 28380 |
| gtacaggcat | gagccaccac | acctggcctc | taaatatata | atctttttttt attcctggtc | 28440 |
| atttccttgc | tctaagtctc | ctttgccaat | aacagctttc | atcctcttgt gtttctggaa | 28500 |
| caggctcccc | tctcatgggc | ctggcttcct | tgcagctgag | gggctttggg agccctc | 28557 |

<210> SEQ ID NO 2
<211> LENGTH: 538
<212> TYPE: PRT
<213> ORGANISM: Homo sapiens

<400> SEQUENCE: 2

```
Met Trp Ser Gly Arg Ser Ser Phe Thr Ser Leu Val Gly Val Phe
1               5                   10                  15

Val Val Tyr Val Val His Thr Cys Trp Val Met Tyr Gly Ile Val Tyr
                20                  25                  30

Thr Arg Pro Cys Ser Gly Asp Ala Asn Cys Ile Gln Pro Tyr Leu Ala
            35                  40                  45

Arg Arg Pro Lys Leu Gln Leu Ser Val Tyr Thr Thr Thr Arg Ser His
    50                  55                  60

Leu Gly Ala Glu Asn Asn Ile Asp Leu Val Leu Asn Val Glu Asp Phe
65                  70                  75                  80

Asp Val Glu Ser Lys Phe Glu Arg Thr Val Asn Val Ser Val Pro Lys
                85                  90                  95

Lys Thr Arg Asn Asn Gly Thr Leu Tyr Ala Tyr Ile Phe Leu His His
                100                 105                 110

Ala Gly Val Leu Pro Trp His Asp Gly Lys Gln Val His Leu Val Ser
            115                 120                 125

Pro Leu Thr Thr Tyr Met Val Pro Lys Pro Glu Glu Ile Asn Leu Leu
            130                 135                 140

Thr Gly Glu Ser Asp Thr Gln Gln Ile Glu Ala Glu Lys Lys Pro Thr
145                 150                 155                 160

Ser Ala Leu Asp Glu Pro Val Ser His Trp Arg Pro Arg Leu Ala Leu
                165                 170                 175

Asn Val Met Ala Asp Asn Phe Val Phe Asp Gly Ser Ser Leu Pro Ala
                180                 185                 190

Asp Val His Arg Tyr Met Lys Met Ile Gln Leu Gly Lys Thr Val His
                195                 200                 205

Tyr Leu Pro Ile Leu Phe Ile Asp Gln Leu Ser Asn Arg Val Lys Asp
            210                 215                 220

Leu Met Val Ile Asn Arg Ser Thr Thr Glu Leu Pro Leu Thr Val Ser
225                 230                 235                 240

Tyr Asp Lys Val Ser Leu Gly Arg Leu Arg Phe Trp Ile His Met Gln
                245                 250                 255

Asp Ala Val Tyr Ser Leu Gln Gln Phe Gly Phe Ser Glu Lys Asp Ala
                260                 265                 270

Asp Glu Val Lys Gly Ile Phe Val Asp Thr Asn Leu Tyr Phe Leu Ala
                275                 280                 285

Leu Thr Phe Phe Val Ala Ala Phe His Leu Leu Phe Asp Phe Leu Ala
            290                 295                 300

Phe Lys Asn Asp Ile Ser Phe Trp Lys Lys Lys Ser Met Ile Gly
305                 310                 315                 320

Met Ser Thr Lys Ala Val Leu Trp Arg Cys Phe Ser Thr Val Val Ile
                325                 330                 335

Phe Leu Phe Leu Leu Asp Glu Gln Thr Ser Leu Leu Val Leu Val Pro
            340                 345                 350

Ala Gly Val Gly Ala Ala Ile Glu Leu Trp Lys Val Lys Lys Ala Leu
            355                 360                 365

Lys Met Thr Ile Phe Trp Arg Gly Leu Met Pro Glu Phe Gln Phe Gly
            370                 375                 380

Thr Tyr Ser Glu Ser Glu Arg Lys Thr Glu Glu Tyr Asp Thr Gln Ala
385                 390                 395                 400

Met Lys Tyr Leu Ser Tyr Leu Leu Tyr Pro Leu Cys Val Gly Gly Ala
                405                 410                 415
```

```
Val Tyr Ser Leu Leu Asn Ile Lys Tyr Lys Ser Trp Tyr Ser Trp Leu
            420                 425                 430

Ile Asn Ser Phe Val Asn Gly Val Tyr Ala Phe Gly Phe Leu Phe Met
        435                 440                 445

Leu Pro Gln Leu Phe Val Asn Tyr Lys Leu Lys Ser Val Ala His Leu
    450                 455                 460

Pro Trp Lys Ala Phe Thr Tyr Lys Ala Phe Asn Thr Phe Ile Asp Asp
465                 470                 475                 480

Val Phe Ala Phe Ile Ile Thr Met Pro Thr Ser His Arg Leu Ala Cys
                485                 490                 495

Phe Arg Asp Asp Val Val Phe Leu Val Tyr Leu Tyr Gln Arg Trp Leu
            500                 505                 510

Tyr Pro Val Asp Lys Arg Val Asn Glu Phe Gly Glu Ser Tyr Glu
            515                 520                 525

Glu Lys Ala Thr Arg Ala Pro His Thr Asp
    530                 535
```

```
<210> SEQ ID NO 3
<211> LENGTH: 1759
<212> TYPE: DNA
<213> ORGANISM: Homo sapiens

<400> SEQUENCE: 3
ctctgaccac ctacatggtc cccaagccag aagaaatcaa cctgctcacc ggggagtctg      60
atacacagca gatcgaggcg gagaagaagc cgacgagtgc cctggatgag ccagtgtccc     120
actggcgacc gcggctggcg ctgaacgtga tggcggacaa cttttgtcttt gacgggtcct    180 ccctgcctgc cgatgtgcat cggtacatga agatgatcca gctggggaaa accgtgcatt     240
acctgcccat cctgttcatc gaccagctca gcaaccgcgt gaaggacctg atggtcataa     300
accgctccac caccgagctg cccctcaccg tgtcctacga caaggtctca ctggggcggc     360
tgcgcttctg gatccacatg caggacgccg tgtactccct gcagcagttc gggttttcag     420
agaaagatgc tgatgaggtg aaaggaattt ttgtagatac caacttatac ttcctggcgc     480
tgaccttctt tgtcgcagcg ttccatcttc tctttgattt cctggccttt aaaaatgaca     540
tcagtttctg gaagaagaag aagagcatga tcggcatgtc caccaagctg tggaaagtga     600
agaaggcatt gaagatgact atttttttgga gaggcctgat gcccgaattt cagtttggca     660
cttacagcga atctgagagg aaaaccgagg agtacgatac tcaggccatg aagtacttgt     720
catacctgct gtaccctctc tgtgtcgggg gtgctgtcta ttcactcctg aatatcaaat     780
ataagagctg gtactcctgg ttaatcaaca gcttcgtcaa cggggtctat gcctttggtt     840
tcctcttcat gctgcccag ctctttgtga actacaagtt gaagtcagtg gcacatctgc     900
cctggaaggc cttcacctac aaggctttca acaccttcat tgatgacgtc tttgccttca     960
tcatcaccat gcccacgtct caccggctgg cctgcttccg ggacgacgtg gtgtttctgg    1020
tctacctgta ccagcggtgg ctttatcctg tggataaacg cagagtgaac gagtttgggg    1080
agtcctacga ggagaaggcc acgcgggcgc cccacacgga ctgaaggccg cccgggctgc    1140
cgccagccaa gtcaacttg aattgtcaat gagtattttt ggaagcattt ggaggaattc     1200
ctagacattg cgtttttctgt gttgccaaaa tcccttcgga catttctcag acatctccca    1260
agttcccatc acgtcagatt tggagctggt agcgcttacg atgccccac gtgtgaacat     1320 ctgtcttggt cacagagctg ggtgctgccg gtcaccttga ctgtggtgg ctcccggcac    1380 acgagtgtcc gggggttcggc catgtcctca cgcgggcagg ggtgggagcc ctcacaggca    1440
```

-continued

```
aggggggctgt tggatttcca tttcaggtgg ttttctaagt gctccttatg tgaatttcaa   1500
acacgtatgg aattcattcc gcatggactc tgggatcaaa ggctctttcc tcttttgttt   1560
gagagttggt tgttttaaag cttaatgtat gtttctattt taaataaat ttttctggct    1620 gtggcatttt tcttgacctg gtataatgaa agtatttcag atatttgagt ttaacccttt   1680
tccagaaagt aatacatgat atggatttat ttatgcatta aaagagcaaa tttaaagagc   1740
aaaaaaaaaa aaaaaaaaa                                                 1759
```

<210> SEQ ID NO 4
<211> LENGTH: 21
<212> TYPE: DNA
<213> ORGANISM: Artificial Sequence
<220> FEATURE:
<223> OTHER INFORMATION: short-hairpin RNAi-inducing construct of novel
      design

<400> SEQUENCE: 4
aactgcatcc agccctatct g                                              21

<210> SEQ ID NO 5
<211> LENGTH: 21
<212> TYPE: DNA
<213> ORGANISM: Artificial Sequence
<220> FEATURE:
<223> OTHER INFORMATION: short-hairpin RNAi-inducing construct of novel
      design

<400> SEQUENCE: 5
aacaatgtgg acctgatctt g                                              21

<210> SEQ ID NO 6
<211> LENGTH: 21
<212> TYPE: DNA
<213> ORGANISM: Artificial Sequence
<220> FEATURE:
<223> OTHER INFORMATION: short hairpin RNA

<400> SEQUENCE: 6
gggacgctgt atgcatatat t                                              21

<210> SEQ ID NO 7
<211> LENGTH: 21
<212> TYPE: DNA
<213> ORGANISM: Artificial Sequence
<220> FEATURE:
<223> OTHER INFORMATION: short hairpin RNA

<400> SEQUENCE: 7
tttcgtagac accaacttat a                                              21

<210> SEQ ID NO 8
<211> LENGTH: 21
<212> TYPE: DNA
<213> ORGANISM: Artificial Sequence
<220> FEATURE:
<223> OTHER INFORMATION: short hairpin RNA

<400> SEQUENCE: 8
cgttccatct tctctttgat t                                              21

<210> SEQ ID NO 9
<211> LENGTH: 21
<212> TYPE: DNA

```
<213> ORGANISM: Artificial Sequence
<220> FEATURE:
<223> OTHER INFORMATION: short-hairpin RNAi-inducing construct of novel
      design

<400> SEQUENCE: 9
cagtttctgg aagaagaaga a                                            21

<210> SEQ ID NO 10
<211> LENGTH: 21
<212> TYPE: DNA
<213> ORGANISM: Artificial Sequence
<220> FEATURE:
<223> OTHER INFORMATION: short hairpin RNAi-inducing construct

<400> SEQUENCE: 10
cagtttctgg aagaaaaaga a                                            21

<210> SEQ ID NO 11
<211> LENGTH: 21
<212> TYPE: DNA
<213> ORGANISM: Artificial Sequence
<220> FEATURE:
<223> OTHER INFORMATION: short hairpin RNAi-inducing construct

<400> SEQUENCE: 11
gtacgatact caggccatga a                                            21

<210> SEQ ID NO 12
<211> LENGTH: 20
<212> TYPE: DNA
<213> ORGANISM: Artificial Sequence
<220> FEATURE:
<223> OTHER INFORMATION: short hairpin RNAi-inducing construct

<400> SEQUENCE: 12
cactcctaaa tatcaagtat                                              20

<210> SEQ ID NO 13
<211> LENGTH: 22
<212> TYPE: DNA
<213> ORGANISM: Artificial Sequence
<220> FEATURE:
<223> OTHER INFORMATION: short hairpin RNAi-inducing construct

<400> SEQUENCE: 13
gcaccctctc ttctcgtgtt tc                                           22

<210> SEQ ID NO 14
<211> LENGTH: 21
<212> TYPE: DNA
<213> ORGANISM: Artificial Sequence
<220> FEATURE:
<223> OTHER INFORMATION: short hairpin RNAi-inducing construct

<400> SEQUENCE: 14
cgtgtgaaca tctgtcttgg t                                            21

<210> SEQ ID NO 15
<211> LENGTH: 21
<212> TYPE: DNA
<213> ORGANISM: Artificial Sequence
<220> FEATURE:
<223> OTHER INFORMATION: short-hairpin RNAi-inducing construct of novel
      design

<400> SEQUENCE: 15
```

```
aattcattcc gcatggactc t                                              21
```

<210> SEQ ID NO 16
<211> LENGTH: 21
<212> TYPE: DNA
<213> ORGANISM: Homo sapiens

<400> SEQUENCE: 16

```
aactgcatcc agccctacct g                                              21
```

<210> SEQ ID NO 17
<211> LENGTH: 21
<212> TYPE: DNA
<213> ORGANISM: Homo sapiens

<400> SEQUENCE: 17

```
aacaatgtgg acctgatctt g                                              21
```

<210> SEQ ID NO 18
<211> LENGTH: 21
<212> TYPE: DNA
<213> ORGANISM: Homo sapiens

<400> SEQUENCE: 18

```
gggacgctgt atgcctacat c                                              21
```

<210> SEQ ID NO 19
<211> LENGTH: 21
<212> TYPE: DNA
<213> ORGANISM: Homo sapiens

<400> SEQUENCE: 19

```
ttttgtagat accaacttat a                                              21
```

<210> SEQ ID NO 20
<211> LENGTH: 21
<212> TYPE: DNA
<213> ORGANISM: Homo sapiens

<400> SEQUENCE: 20

```
cgttccatct tctctttgat t                                              21
```

<210> SEQ ID NO 21
<211> LENGTH: 21
<212> TYPE: DNA
<213> ORGANISM: Homo sapiens

<400> SEQUENCE: 21

```
cagtttctgg aagaagaaga a                                              21
```

<210> SEQ ID NO 22
<211> LENGTH: 21
<212> TYPE: DNA
<213> ORGANISM: Homo sapiens

<400> SEQUENCE: 22

```
cagtttctgg aagaagaaga a                                              21
```

<210> SEQ ID NO 23
<211> LENGTH: 21
<212> TYPE: DNA
<213> ORGANISM: Homo sapiens

```
<400> SEQUENCE: 23
gtacgatact caggccatga a                                              21

<210> SEQ ID NO 24
<211> LENGTH: 20
<212> TYPE: DNA
<213> ORGANISM: Homo sapiens

<400> SEQUENCE: 24
cactcctgaa tatcaaatat                                                20

<210> SEQ ID NO 25
<211> LENGTH: 21
<212> TYPE: DNA
<213> ORGANISM: Homo sapiens

<400> SEQUENCE: 25
gttcccatca cgtcagattt g                                              21

<210> SEQ ID NO 26
<211> LENGTH: 21
<212> TYPE: DNA
<213> ORGANISM: Homo sapiens

<400> SEQUENCE: 26
cgtgtgaaca tctgtcttgg t                                              21

<210> SEQ ID NO 27
<211> LENGTH: 21
<212> TYPE: DNA
<213> ORGANISM: Homo sapiens

<400> SEQUENCE: 27
aattcattcc gcatggactc t                                              21

<210> SEQ ID NO 28
<211> LENGTH: 57
<212> TYPE: DNA
<213> ORGANISM: Artificial Sequence
<220> FEATURE:
<223> OTHER INFORMATION: shTERT1-F

<400> SEQUENCE: 28
ccggaagtct gccgttgccc aagagctcga gctcttgggc aacggcagac tttttt        57

<210> SEQ ID NO 29
<211> LENGTH: 57
<212> TYPE: DNA
<213> ORGANISM: Artificial Sequence
<220> FEATURE:
<223> OTHER INFORMATION: shTERT1-R

<400> SEQUENCE: 29
aattaaaaaa actgcatcca gccctatctg ctcgagcaga tagggctgga tgcagtt       57

<210> SEQ ID NO 30
<211> LENGTH: 57
<212> TYPE: DNA
<213> ORGANISM: Artificial Sequence
<220> FEATURE:
<223> OTHER INFORMATION: shCLP2-F

<400> SEQUENCE: 30
ccggaactgc atccagccct atctgctcga gcagataggg ctggatgcag tttttt        57
```

```
<210> SEQ ID NO 31
<211> LENGTH: 57
<212> TYPE: DNA
<213> ORGANISM: Artificial Sequence
<220> FEATURE:
<223> OTHER INFORMATION: shCLP2-R

<400> SEQUENCE: 31
aattaaaaaa actgcatcca gccctatctg ctcgagcaga tagggctgga tgcagtt        57

<210> SEQ ID NO 32
<211> LENGTH: 21
<212> TYPE: DNA
<213> ORGANISM: Artificial Sequence
<220> FEATURE:
<223> OTHER INFORMATION: sh1 974m

<400> SEQUENCE: 32
cagtttctgg aagaaaaga a                                                21

<210> SEQ ID NO 33
<211> LENGTH: 21
<212> TYPE: DNA
<213> ORGANISM: Artificial Sequence
<220> FEATURE:
<223> OTHER INFORMATION: sh2 168m

<400> SEQUENCE: 33
aactgcatcc agccctatct g                                               21

<210> SEQ ID NO 34
<211> LENGTH: 21
<212> TYPE: DNA
<213> ORGANISM: Artificial Sequence
<220> FEATURE:
<223> OTHER INFORMATION: sh3 252m

<400> SEQUENCE: 34
aacaatgtgg acctgatctt g                                               21

<210> SEQ ID NO 35
<211> LENGTH: 21
<212> TYPE: DNA
<213> ORGANISM: Artificial Sequence
<220> FEATURE:
<223> OTHER INFORMATION: sh4 2050m

<400> SEQUENCE: 35
aagtcgttct gtacggactc t                                               21
```